US007781393B2

(12) United States Patent
Kung et al.

(10) Patent No.: US 7,781,393 B2
(45) Date of Patent: Aug. 24, 2010

(54) METHODS FOR INHIBITING TUMOR CELL GROWTH

(75) Inventors: Andrew Kung, Walpole, MA (US); Constantine S. Mitsiades, Boston, MA (US); Nicholas Mitsiades, W. Roxbury, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 132 days.

(21) Appl. No.: 10/590,672

(22) PCT Filed: Feb. 25, 2005

(86) PCT No.: PCT/US2005/005922

§ 371 (c)(1),
(2), (4) Date: Oct. 23, 2007

(87) PCT Pub. No.: WO2005/082415

PCT Pub. Date: Sep. 9, 2005

(65) Prior Publication Data

US 2008/0193462 A1 Aug. 14, 2008

Related U.S. Application Data

(60) Provisional application No. 60/547,516, filed on Feb. 25, 2004.

(51) Int. Cl.
*A01N 61/00* (2006.01)
*A61K 39/00* (2006.01)
*A61K 35/12* (2006.01)

(52) U.S. Cl. ...................... 514/1; 424/184.1; 424/277.1

(58) Field of Classification Search ...................... None
See application file for complete search history.

(56) References Cited

U.S. PATENT DOCUMENTS

| 4,987,071 A | 1/1991 | Cech et al. ...................... 435/91 |
| 5,116,742 A | 5/1992 | Cech et al. ...................... 435/91 |
| 6,337,338 B1 * | 1/2002 | Kozlowski et al. ........... 514/311 |
| 6,692,742 B1 * | 2/2004 | Nakamura et al. ........ 424/145.1 |
| 2004/0044203 A1 * | 3/2004 | Wittman et al. ................ 544/55 |
| 2004/0072760 A1 * | 4/2004 | Carboni et al. ................. 514/17 |
| 2005/0075358 A1 * | 4/2005 | Carboni et al. ............... 514/269 |

FOREIGN PATENT DOCUMENTS

| WO | WO 95/20960 | 8/1995 |
| WO | WO 98/06391 | 2/1998 |
| WO | WO 99/32619 | 7/1999 |
| WO | WO 00/44895 | 8/2000 |
| WO | WO 01/29058 A1 | 4/2001 |
| WO | WO 01/75164 A2 | 10/2001 |
| WO | WO 01/87307 A2 | 11/2001 |
| WO | WO 01/89304 A1 | 11/2001 |
| WO | WO 01/92513 A1 | 12/2001 |
| WO | WO 02/16620 A2 | 2/2002 |
| WO | WO 02/17904 A1 | 3/2002 |
| WO | WO 02/29858 A2 | 4/2002 |
| WO | WO 02/080987 A1 | 10/2002 |
| WO | WO02/092599 | * 11/2002 |
| WO | WO 02/092599 A1 | 11/2002 |
| WO | WO 02/102804 A1 | 12/2002 |
| WO | WO 03/027246 A2 | 4/2003 |
| WO | WO 2004/030627 A2 | 4/2004 |

OTHER PUBLICATIONS

Doxorubicin Proposed PI Update, FDA document for final approved label. May 2003.*
Anderson et al., "Role of Cytokines in Multiple Myeloma", *Semin. Hematol.*, 36(1, Suppl. 3):14-20 (1999).
Bartel et al., "Isolation of New Ribozymes from a Large Pool of Random Sequences", *Science*, 261:1411-1418 (1993).
Beech et al., "Insulin-like growth factor-I receptor antagonism results in increased cytotoxicity of breast cancer cells to doxorubicin and taxol", *Oncol. Rep.*, 8(2):325-329 (2001).
Benini et al., "Inhibition of insulin-like growth factor I receptor increases the antitumor activity of doxorubicin and vincristine against Ewing's sarcoma cells", *Clin .Cancer Res.*, Abstract only, 7(6):1790-1797 (2001).
Blum et al., "Substrate Competitive Inhibitors of IGF-1 Receptor Kinase", *Biochem.*, 39:15705-15712 (2000).
Database CA 'Online, Chemical Abstracts Service, Columbus, Ohio, US: May 22,2002, Wen et al., "Tyrphostin AG 1024 modulates radiosensitivity in human breast cancer cells", XP002977524, retrieved from STN Database accession No. 2002:141503, Abstract & *Brit. J. Cancer*, 85(12):2017-2021 (2001).
Fukuda et al., "Insulin-like growth factor 1 induces hypoxia-inducible factor 1-mediated vascular endothelial growth factor expression, which is dependent on MAP kinase and phosphatidylinositor 3-kinase signaling in colon cancer cells", *J. Biol. Chem.*, 277(41):38205-38211 (2002).
GenBank Accession No. AF064078, Aug. 10, 2000.
GenBank Accession No. AH002704, Nov. 8, 1994.
GenBank Accession No. AY260957, Apr. 3, 2003.
GenBank Accession No. AY790940, Nov. 2, 2004.
GenBank Accession No. CR541861, Oct. 16, 2008.
GenBank Accession No. EO2872, Nov. 4, 2005.
GenBank Accession No. M22373, Nov. 8, 1994.
GenBank Accession No. NM000875, Apr. 10, 2009.
GenBank Accession No. NM00876, Apr. 19, 2009.
GenBank Accession No. NM004215, Jan. 25, 2009.
GenBank Accession No. S62621, Aug. 25, 1993.
GenBank Accession No. T27620, Sep. 6, 1995.
GenBank Accession No. T29467, Sep. 6, 1995.
GenBank Accession No. X05113, Apr. 4, 1997.

(Continued)

*Primary Examiner*—Larry R. Helms
*Assistant Examiner*—Lei Yao
(74) *Attorney, Agent, or Firm*—Mintz, Levin, Cohn, Ferris, Glovsky and Popeo, P.C.; Ivor R. Elrifi; Cynthia A. Kozakiewicz

(57) ABSTRACT

The invention methods using a insulin-like growth factor receptor inhibitor to inhibit tumor cell growth in a subject in need thereof.

14 Claims, 30 Drawing Sheets

OTHER PUBLICATIONS

GenBank Accession No. L15440, Jan. 6, 1995.
GenBank Accession No. M22372, Nov. 8, 1994.
Hallek et al., "Multiple myeloma: increasing evidence for a multistep transformation process", *Blood*, 91:3-21 (1998).
Haselhoff et al., "Simple RNA enzymes with new and highly specific endoribonuclease activities", *Nature*, 334(6183):585-591 (1988).
Helene et al., "Control of Gene Expression by Triple Helix-Forming Oligonucleotides. The Antigene Strategy", *Ann. N. Y. Acad. Sci.*, 660:27-36 (1992).
Helene, C., "The anti-gene strategy: control of gene expression by triplex-forming-oligonucleotides", *Anti-cancer Drug Des.*, 6(6):569-584 (1991).
Lei et al., "Enhancement of chemosensitivity and programmed cell death by tyrosine kinase inhibitors correlates with EGFR expression in non-small cell lung cancer cells", *Anticancer Res.*, 19(1A):221-228 (1989).
Maher, III, J.L, "DNA Triple-Helix Formation: An Approach to Artificial Gene Repressors?" *Bioassays*, 14(12):807-815 (1992).
Mitsiades et al., "Apoptotic signaling induced by immunomodulatory thalidomide analogs in human multiple myeloma cells: therapeutic implications", *Blood*, 99(12):4525-4530 (2002).
Mitsiades et al., "Biologic sequelae of nuclear factor-κB blockade in multiple myeloma: therapeutic applications", 99(11):4079-4086 (2002).
Mitsiades et al., "Inhibition of the insulin-like growth factor receptor-1 tyrosine kinase activity as a therapeutic strategy for multiple myeloma, other hematologic malignancies, and solid tumors", *Cancer Cell*, 5:221-230 (2004).
Mitsiades et al., "Molecular sequelae of proteasome inhibition in human multiple myeloma cells" *Proc. Natl. Sci. USA*, 99(22):14374-14379 (2002).
Mitsiades et al., "Proteomic Analyses in Waldenstrom's Macroglobulinemia and Other Plasma Cell Dyscrasias", *Semin. Oncol.*, 30(2):156-160 (2003).
Mitsiades et al., "The proteasome inhibitor PS-341 potentiates sensitivity of multiple myeloma cells to converntional chemotherapeutic agents: therapeutic applications", *Blood*, 101(6):2377-2380 (2003).
Nakashima et al., "Serum Interleukin 6 as a Prognostic Factor in Patients with Prostate Cancer", *Clin. Cancer Res.*, 6:2702-2706 (2000).
Arcaro, A., et al: "Potent inhibition of human atypical teratoid/rhabdoid tumor growth by the novel insulin-like growth factor receptor inhibitor NVP-AEW541", Mol Mind (Feb. 17, 19, 2005 Zurich), abst. P004.
Capraro, H-G, et al: "Synthesis and SAR of 5,7-disubstituted pyrrolo[2,3-d]pyrimidine derivatives, a class of highly potent and selective Insulin-like Growth Factor 1 Receptor (IGF-1R) Inhibitors", Drugs Fut, 29(Suppl. A), P111(2004) Abstract Only.
Ferreira Brandao Guerreiro, A.S., et al: "Targeting IGF-IR in human neuroblastoma: Potent antitumor activity of the novel inhibitor NVP-AEW541", Mol Mind (Feb. 17-19, 2005 Zurich), P039 Abstract Only.
Garcia-Echeverria, C.: "Targeted anti-cancer drugs—dream or reality?", CNIO Symposium: Molecular Taxonomy of Cancer (Feb. 3-6, 2004 Madrid), Abstract Only.
Garcia-Echeverria, C., et al: "The discovery of potent and selective insulin-like growth factor I receptor kinase inhibitors", 29th Natl Med Chem Syp (Jun. 27-Jul. 1, 2004 Madison), Abst 58.
Garcia-Echeverria, C., et al: "In vivo antitumor activity of NVP-AEW541—A novel, potent, and selective inhibitor of the IGF-IR kinase", Cancer Cell, 5(3): 231-239 (2004).
Garcia-Echeverria, C., et al: "NVP-AEW541—a novel, potent and selective inhibitor of the IGF-1R kinase", MMRF Res Roundtable: Novel Target Ther Treat Multiple Myeloma (Apr. 20-21, 2004 Torino) Abstract Only.
Krystal, G., et al: "Small molecule receptor tyrosine kinase inhibitors delineate a spectrum of dependence of SCLC cell lines on IGF-1 and SCF signaling", 15th AACR-NCI-EORTC Int Conf Mol Targets Cancer Ther (Nov. 17-21, 2003 Boston), Abst B159.
Krystal, G.W., et al: "The IGF-1R kinase inhibitor NVP-ADW742 sensitizes small cell lung cancer cell lines to the effects of chemotherapy", Proc Am Assoc Cancer Res (AACR) 2005, 46: Abst 5040.
Mitsiades, C. et al: "IGF-1 receptor inhibition: A novel therapeutic strategy for multiple myeloma", MMRF Res Roundtable: Novel Target Ther Treat Multiple Myeloma (Apr. 20-21, 2004 Torino), Abst.
Mitsiades, C., et al: "Characterization of selective small molecule kinase inhibitors of IGF-IR and their in vitro and in vivo activity against multiple myeloma, other hematologic malignancies and solid tumors", 15th AACR-NCI-EORTC Int Conf Mol Targets Cancer Ther (Nov. 17-21, 2003 Boston), Abst A280.
Mitsiades, C.S., et al, "The IGF/IGF-1R system is a major therapeutic target for multiple myeloma, other hematologic malignancies and solid tumors", Proc Am Assoc Cancer Res (AACR) 2003, 44(2nd ed): Abst 4005.
Mitsiades, N., et al: "NVP-AEW541: A selective small molecule IGF-1R tyrosine kinase inhibitor is active against multiple myeloma and other hematologic neoplasias and solid tumors", Blood 2004, 104(11, Part 1): Abst 766.
O'Reilly, K., et al: "The abrogation of rapamycin-induced AKT activity by the small molecule IGF-IR inhibitor, AEW541, and the enhanced antitumor activity of combined mTOR and IGF-IR inhibition", Eur J Cancer Suppl 2004, 2 (8): Abst 388.
Schnell, C., et al: "Characterization of the effects of a small molecular weight inhibitor on IGF-I induced angiogenesis", Proc Am Assoc Cancer Res (AACR) 2005, 46: Abst 1529.
Scotlandi, K., et al: "Effectiveness of a novel, selective inhibitor of the IGF-IR kinase against musculoskeletal tumors", Eur J Cancer Suppl 2004, 2(8): Abst 340.
Warshamana-Greene, G.S., et al: "The insulin-like growth factor-I receptor kinase inhibitor, NVP-ADW742, sensitizes small cell lung cancer cell lines to the effects of chemotherapy", Clin Cancer Res, 11(4): 1563-1571 (2005).
Warshamana-Green, G.S., et al: "The novel IGF-1R kinase inhibitor NVP-ADW742 acts synergistically with STI571 and etoposide to block PI3K-Akt activity, inhibit growth and promote apoptosis in SCLC", Proc Am Assoc Cancer Res (AACR) 2004, 45: Abst 3685.
Warshamana-Green, G.S., et al: "The insulin-like growth factor-I (IGF-I) receptor kinase inhibitor NVP-ADW742, in combination with STI571, delineates a spectrum of dependence of small cell lung cancer on IGF-I and stem cell factor signaling", Mol. Cancer Ther., 3(5): 527-535 (2004).
Zhao Y., et al: "IGF-I receptor kinase inhibitor NVP-AEW541-NX-7 abolishes MCF-7 breast cancer cell responsivity to estradiol", Eur J Cancer Suppl 2004, 2(8): Abst 357.
"Inhibitors of signal transduction pathways", 373522, Drug Data Report 2004, 26(10), p. 966-967.

* cited by examiner

Figure 2
a
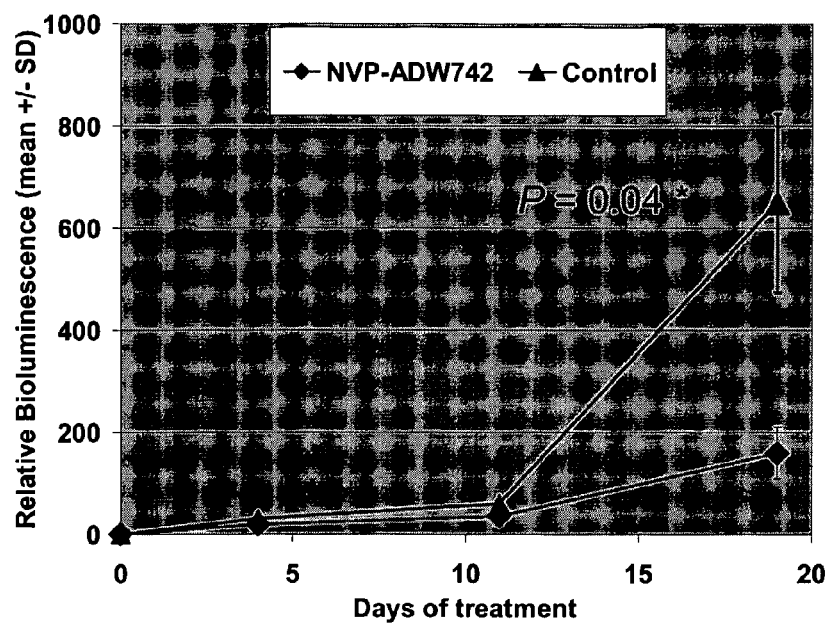
b
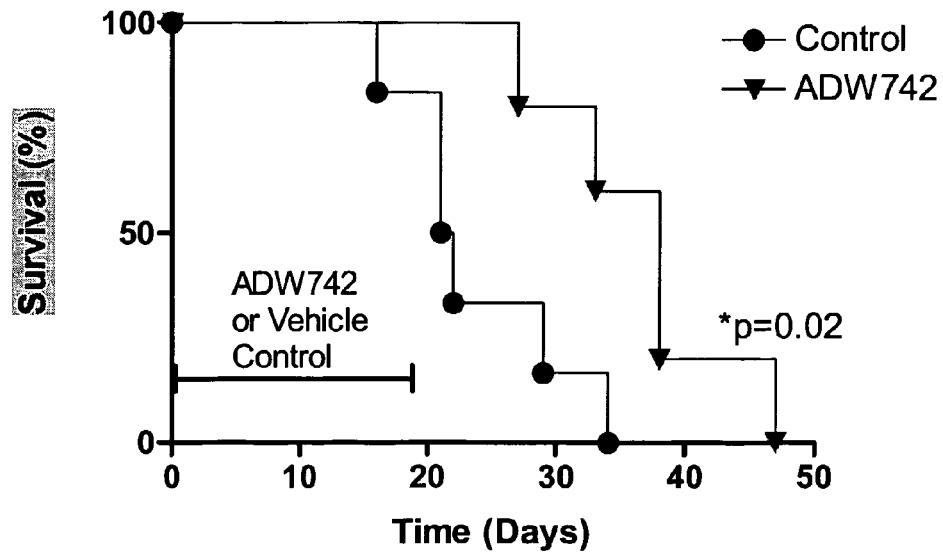
c

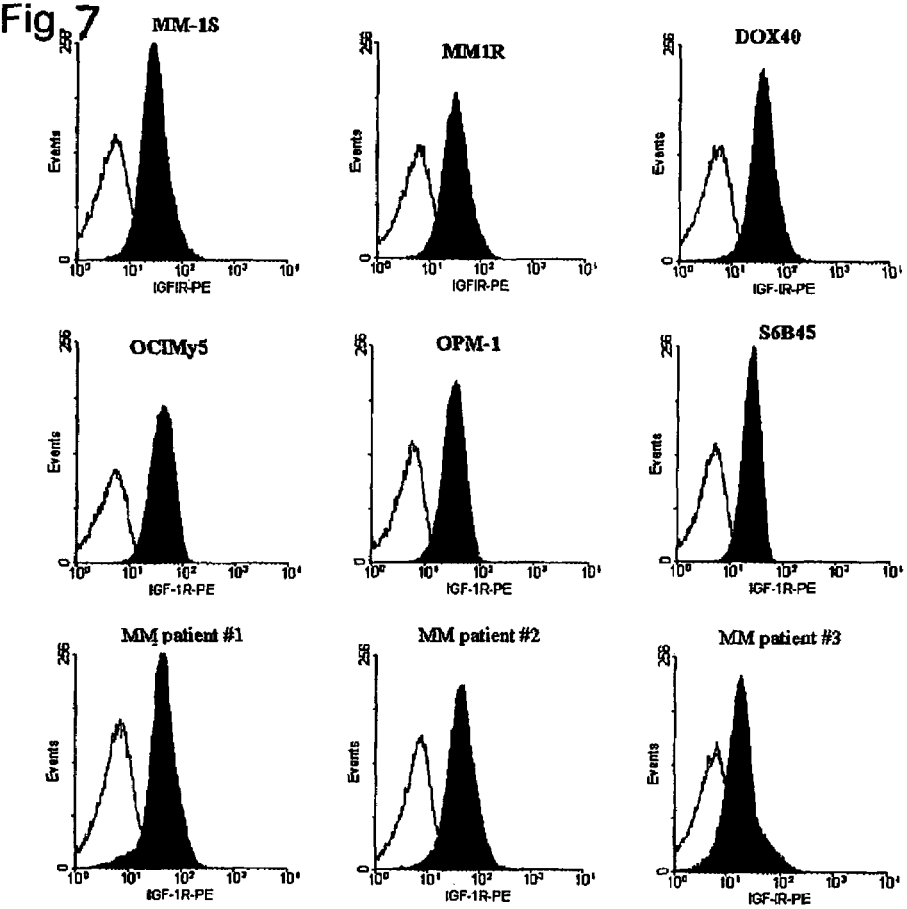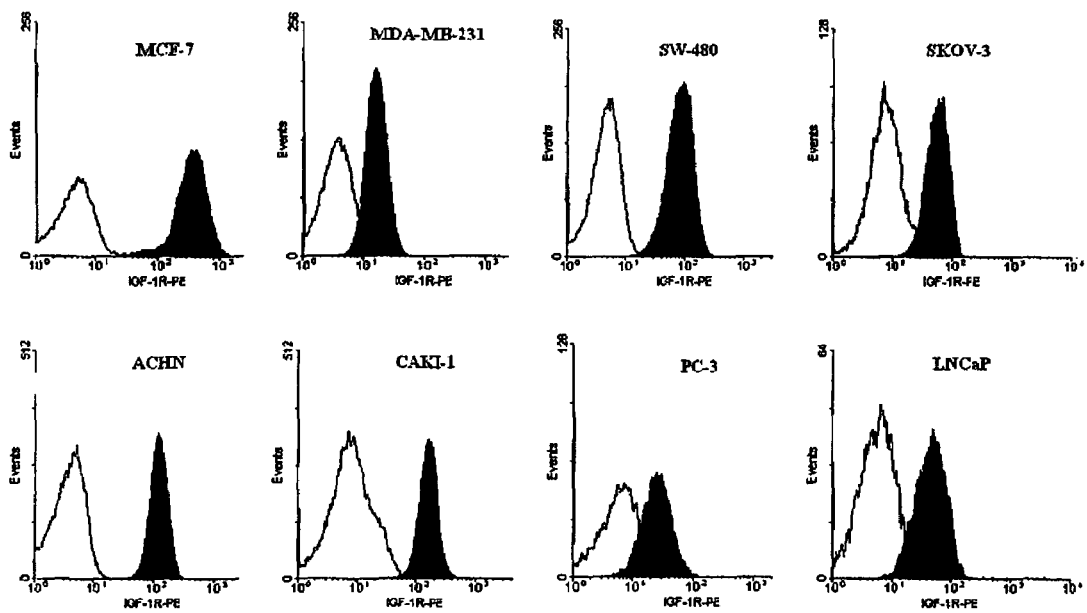
Fig. 7

Figure 8
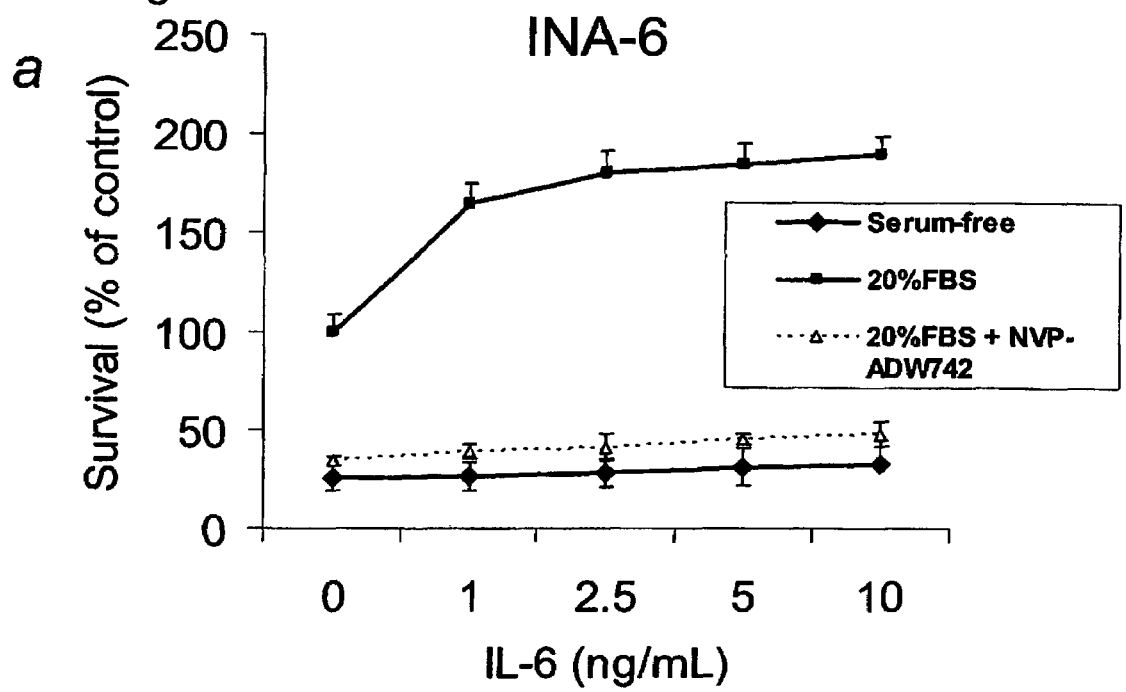
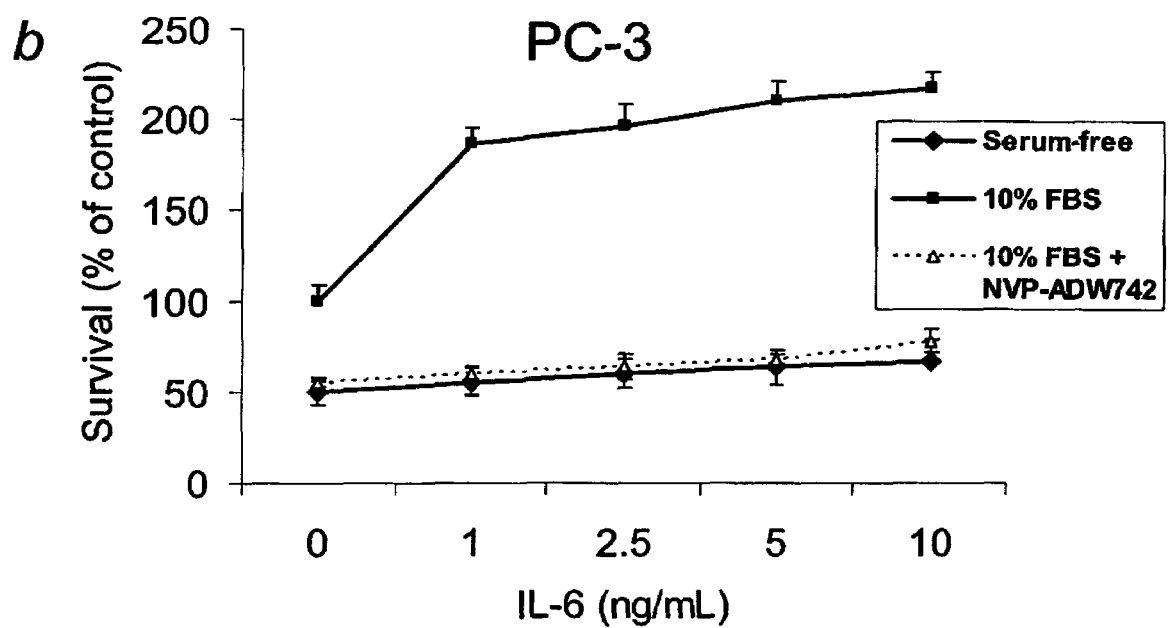

Figure 10

Transcriptional signature of IGF-1 stimulation

| | Upregulated | Downregulated |
|---|---|---|
| Cell signaling | CK-1 and -2, chemokine-like factor 1, CXCR-4, Aurora-1, Aurora-2, SAK, SGK, PP2A, some PP1 subunits, PP4, GADD-α and –β, PTEN, CD71 | FLIP, c-raf1 (but upregulated at protein level), Gas6, IGF-1, IGF-1R, IGF-2R, IFN-a, b, omega receptor, IL-2Rγ, gp130, RAR-α, RAR-γ, BCMA, TNF-a-induced protein |
| Apoptosis regulation | Survivin, Bad, PCD5, PCD8, PCD10, VDAC3 | Bcl-2 (no effect on protein level on short- to mid-term stimulation), Mcl-1 (stable protein levels), TOSO |
| Cell cycle control | Ki-67, CDC -2,-5, -6, -7, -20, -23, -25, -28, -45, cyclins A2, B1, B2, E1, F, G1, (D1, D2, D3), CDK2, CDK4, PCNA, replication factor C (multiple subunits), replication proteins A1, A2, and A3, ASK, CHK1, G2-S-expressed 1, stathmin/oncoprotein 1, Wee1+ | |
| Microenvironmental interactions | RHAMM, Integrin αE, ADAM-8, -22, -28 | Integrin α8, αL, β1, β5 |
| Wnt signaling pathway | | Frizzled-related protein, WNT10B, WNT5B |
| Transcriptional/translational control | ATF-1, ATF-3, E2F-3, eIF-1, -2, -3, -4 and -5, multiple ribosomal proteins, DP-1, c-myb, XBP-1 | c-myc |
| DNA synthesis/repair enzymes | BUB1, BUB3, DNA-PK, deoxycytidine kinase, deoxythymidylate kinase, DHFR, dyskerin, dUTP pyrophosphatase, MCM 2, 3, 4, 5, 6, 7, MSH-2, -3, -6, RAD51, guanine monophosphate synthase, RRM1, RRM2, TOPOIIA, XRCC | |
| Histone regulation | HDAC1, HAT1 | |
| Oncogenes | DEK, liposarcoma fusion gene t(12;16), SET translocation | |
| Heat shock proteins / Chaperones | Hsp90, -70, 105, 27, 110, 14-3-3, chaperonin TCP1 | |
| Immune system interactions | | MHC class IE and II (less extensive changes in comparison to IL-6 or co-Cx) |
| Nucleocytoplasmic transport and other carrier proteins | Exportin, nucleoporins 50, 54, 62, 88, 98, 155, karyopherins b1, b3, a1, a2, a3, a4, kinesin-like 1, 2, 4, 5, 6, 7 (multiple Rab, Ran proteins), transportins | |
| Metabolism | F0F1 ATPase mitochondrial, ornithine decarboxylase, HMG-CoA reductase, calmodulin-1 and -2 | |
| Ubiquitin/Proteasome pathway | POH, Multiple 26S subunit genes (26S subunits α1, α2, α3, α5, α7, β1, β2, β3, β5, β6, β7, β8, ATPase 1,2, 3, 4, 5, 6, non-ATPase 1, 2, 4, 7, 8, 11, 12, 13), UCEs, USPs | Some USPs (-9, -11) |

ADW742

5-(3-Benzyloxy-phenyl)-7-(3-pyrrolidin-1-ylmethyl-cyclobutyl)-7H-pyrrolo[2,3-d]pyrimidin-4-ylamine

AEW541

7-(3-Azetidin-1-ylmethyl-cyclobutyl)-5-(3-benzyloxy-phenyl)-7H-pyrrolo[2,3-d]pyrimidin-4-ylamine

METHODS FOR INHIBITING TUMOR CELL GROWTH

RELATED APPLICATIONS

This application is a national stage application, filed under 35 U.S.C. §371, of International Application No. PCT/US05/005922, filed on Feb. 25, 2005, which claims the benefit of U.S. Ser. No. 60/547,516, filed Feb. 25, 2004.

FIELD OF THE INVENTION

The invention relates to inhibition of tumor cell growth.

BACKGROUND OF THE INVENTION

Insulin-like growth factors-1 (IGF-1) and -2 (IGF-2) have been implicated in the pathophysiology of a wide range of human neoplasias due to the mitogenic and anti-apoptotic properties mediated by their type I receptor (IGF-1R or CD221). Expression of functional IGF-1R is required for neoplastic transformation in diverse tumorigenesis models. However, the art has not applied the inhibition of the IGF-1R pathway as a major anti-cancer therapeutic strategy, due, in part, to the lack of clinically-applicable small molecule inhibitors of IGF-1R function, and in part to the uncertainty of the clinical impact of inhibiting the IGF/IGF-1R pathway in tumor cell proliferation and survival. Moreover, widespread expression of IGF-1R in normal tissues raises concerns regarding the specificity and the toxicity of IGF/IGF-1R pathway inhibition.

SUMMARY OF THE INVENTION

The invention is based in part on the discovery of multiple strategies for specific inhibition of IGF-1R function, which have potent anti-tumor effects across a broad range of tumor types.

In various aspects the invention provides methods of inhibiting tumor cell growth by administering to a subject or contacting a tissue with a cytotoxic agent or a chemotherapeutic agent and a composition containing an insulin-like growth factor receptor-1 (IGF-1R) inhibitor.

The IGF-1R inhibitor is administered concomitantly with the cytotoxic agent or chemotherapeutic agent. Alternatively the IGF-1R inhibitor is administered after the cytotoxic agent or chemotherapeutic agent. For example, the IGF-1R inhibitor is administered 1, 2, 3, 6, 12, 24, or 48 hours or more after the cytotoxic agent or chemotherapeutic agent. The IGF-1R inhibitor is administered as a single dose or in multiples doses over a preselected period of time. For example, the IGF-1R inhibitor is administered over 1-2 days. The dose is sub-therapeutic. Optimally, the IGF-1R inhibitor is given at a dose sufficient to cause aberrant glucose homeostasis. For example, the IGF-1R inhibitor is given at dose to cause hyperglycemia, ketosis or glucosuria in the subject.

A cytotoxic agent is any agent capable of causing cell death such as radiation therapy or a chemotherapeutic agent. The chemotherapeutic agent is any agent typically used to treat cancer. Exemplary chemotherapeutic agents are doxorubicin, melphalan or dexamethasone.

In another aspect tumor cell growth is inhibited by administering to a subject a first composition containing a compound which lowers the concentration (e.g., serum concentration or tumor microenvironment concentration) of insulin-like growth factors (e.g., IGF-1 or IGF-2) and a second composition comprising an insulin-like growth factor receptor-1 (IGF-1R) inhibitor. The IGFs (e.g. IGF-1) are produced by the liver. Alternatively, IGFs are produced by the tumor and/or tumor-associated stromal cells. Compounds that lower the concentration of IGF-1 are known in the art and include somatostatin or analogues thereof. The second composition is administered concomitantly with the first composition. Alternatively, the second composition is administered after the first composition (e.g. 1, 2, 3, 6, 12, 24, 48 hours or more)

In a further aspect, the invention provides methods of inhibiting tumor cell growth by administering to a subject a composition including an insulin-like growth factor receptor-1 (IGF-1R) inhibitor and an anti-diabetic agent. The anti-diabetic agent is an insulin polypeptide, an insulin sensitivity enhancer (e.g., thiazolidineodione or a biguanide), and an insulin secretion enhancer (e.g., glucosidase inhibitor).

In yet a further aspect, the invention provides a method of inhibiting tumor cell growth by administering to a subject a composition including a compound that decreases the expression (e.g., cell surface expression) or activity of an IGF-1R. Optionally, the method further includes administering to the subject a composition containing an IGF-1R inhibitor.

Compounds that decrease the expression or activity of an IGF-1R include for example a siRNA or an IGF-1R anti-sense nucleic acid. Additional compounds include those compounds that inhibit intracellular trafficking of the IGF-1R; inhibit post-translational modification of the IGF-1R; enhance degradation or ubiquitination of the IGF-1R; or disrupt the proper 3-dimensional conformation of the IGF-1R.

The invention further provides methods of reducing angiogenesis in a tissue, e.g. tumor tissue or inducing apoptosis in a cell, by contacting the cell or tissue with an insulin-like growth factor receptor-1 (IGF-1R) inhibitor.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 2a is a photographic image demonstrating the representative results of whole-body bioluminescence imaging of SCID/NOD mice injected i.v. with $5 \times 10^6$ MM-1S-Luc$^+$ human MM cells. Imaging 3 weeks after injection of cells reveals lesions in the spine, skull, and pelvis, with eventual progression to diffuse disease.

FIG. 2b is a line graph demonstrating the quantification of total tumor burden in mice receiving ADW-742 (10 mg/kg i.p. twice daily for 19 days) vs. vehicle-treated mice. Data represented as mean ±SD, n=6 per group.

FIG. 2c is a line graph demonstrating the Kaplan-Meier survival curve of ADW-742-treated vs. control SCID/NOD mice. Mice were treated for 19 days at the doses indicated in FIG. 2b. Mice treated with ADW-742 had longer median overall survival than control mice (38 days vs. 21 days, respectively, P=0.02, log-rank test).

FIG. 7a is a collection of tracings showing flow cytometric analyses of cell surface IGF-1R (shaded curves) in drug-sensitive and drug-resistant MM cell lines (MM-IS, MM-1R, RPMI-8226/S, RPMI-8226/Dox40, OCI-My5, OPM-1, S6B45), primary MM tumor cells from patients resistant to conventional or investigational drugs (MM patient #1, #2, #3). Results are representative of the entire panel of tumor samples tested and of analyses with 2 different anti-IGF-1R-specific mab's. Unshaded curves correspond to isotype-matched controls.

FIG. 7b is a collection of tracings showing flow cytometric analyses of cell surface IGF-1R (shaded curves) in solid tumor cell lines (ACHN and CAKI-1 renal cell carcinoma, MCF-7 and MDA-MB-231 breast carcinoma, PC-3 and LNCaP prostate carcinoma, SW-480 colorectal carcinoma and SKOV-3 ovarian cancer). Results are representative of the entire panel of tumor samples tested and of analyses with 2 different anti-IGF-1R-specific mAb's. Unshaded curves correspond to isotype-matched controls.

FIG. 8a is a line graph demonstrating that in the presence of serum, the INA-6 MM cells are responsive to IL-6 at the indicated concentration as shown by MTT assays after 72 hours of incubation. However, this responsiveness is abrogated in the absence of serum or upon co-treatment with ADW-742 (500 nM).

FIG. 8b is a line graph demonstrating that in the presence of serum, the PC-3 prostate cancer cells are responsive to IL-6 at the indicated concentration as shown by MTT assays after 72 hours of incubation. However, this responsiveness is abrogated in the absence of serum or upon co-treatment with ADW-742 (500 nM).

Figure 9:
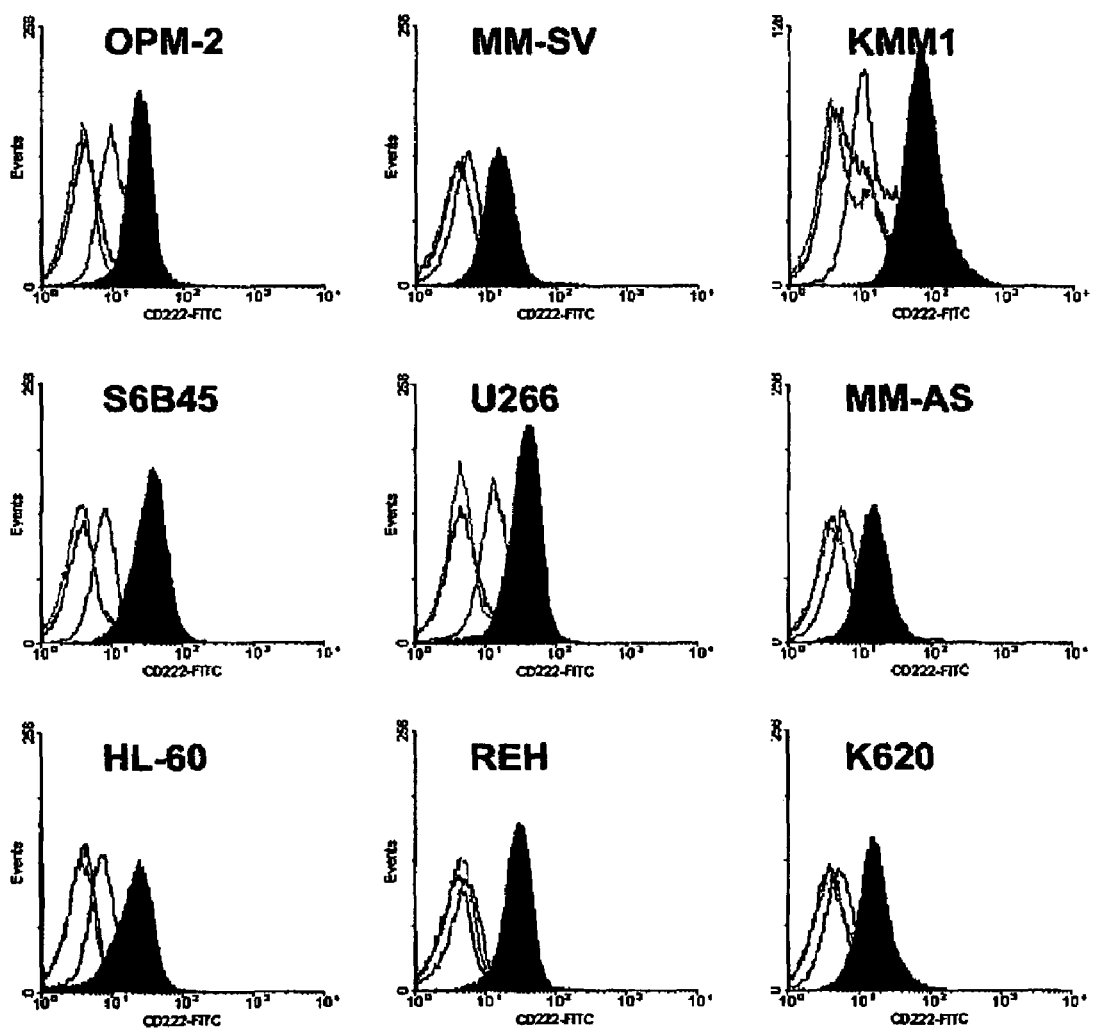

FIG. 9 is a collection of tracings demonstrating the cell surface and intracellular IGF-2R expression in malignant cells. Representative flow cytometric analyses of cell surface (medium gray line curves) and intracellular (shaded curves) IGF-2R in multiple myeloma (OPM-2, MM-SV, MM-AS, KMM1, S6B45, U266, K620) and leukemic cells (HL-60, REH). (The black and light-gray curves correspond to isotype-matched controls for cell surface and intracellular IGF-2R analyses, respectively).

FIG. 10 is an illustration of a table showing the transcriptional signature of IGF-1 stimulation.

Figure 11:
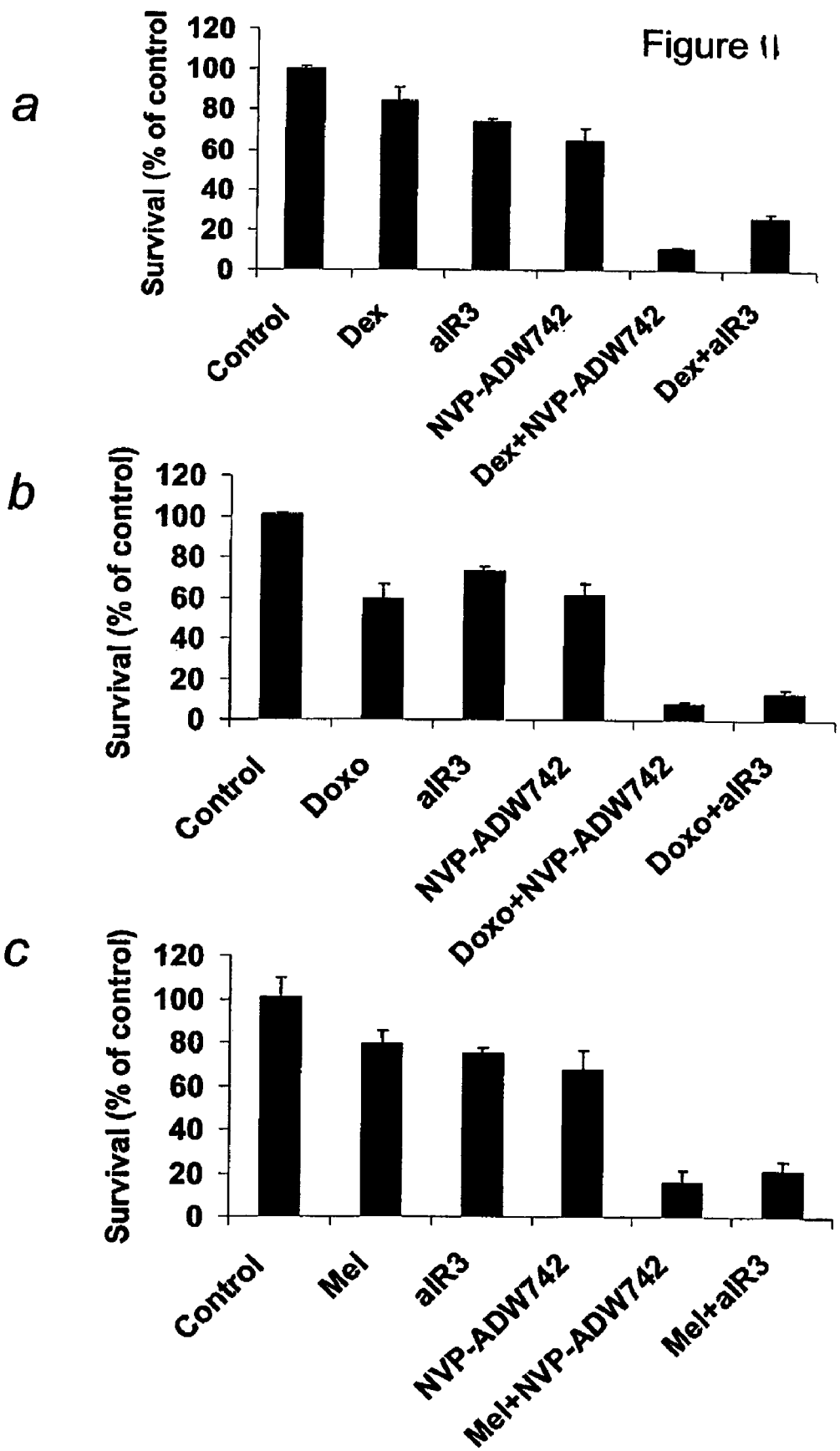

FIG. 11a is a bar chart indicating that ADW-742 (750 nM for the final 24 hours of incubation) and α-IR3 (2 µg/ml for the final 24 hours of incubation) enhances the sensitivity of MM-1S cells to dexamethasone (0.1 µM for 72 hrs).

FIG. 11b is a bar chart indicating that ADW-742 (750 nM for the final 24 hours of incubation) and α-IR3 (2 µg/ml for the final 24 hours of incubation) enhance the sensitivity of MM-1S cells to doxorubicin (50 ng/mL for 48 hrs).

FIG. 11c is a bar chart indicating that ADW-742 (750 nM for the final 24 hours of incubation) and α-IR3 (2 µg/ml for the final 24 hours of incubation) enhance the sensitivity of MM-1S cells to melphalan (1 µM for 48 hrs).

Figure 12:
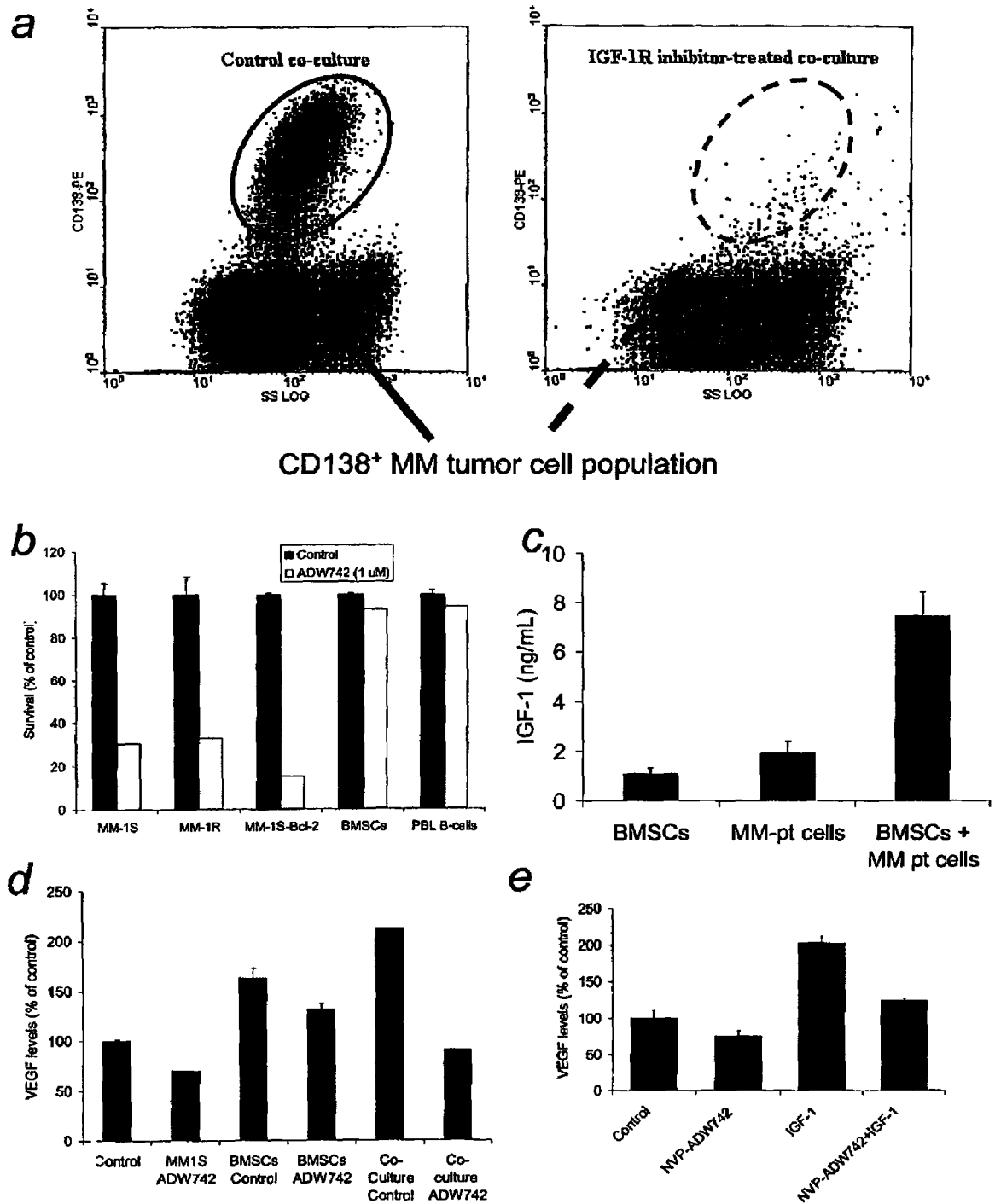

FIG. 12a is a scatter plot showing the results of flow cytometric analysis of unpurified bone marrow (BM) mononuclear cells from BM aspirate of MM patient (which contain CD138$^+$ MM cells and CD138$^-$ normal cells of the bone microenvironment, such as stromal cells) after culture in 20% serum, with or without ADW-742 for 72 hours. ADW-742 treatment (500 nM) leads to significant suppression of the CD138$^+$ population of malignant cells, but not BM stromal cells.

FIG. 12b is a bar chart indicating that ADW-742 (500 nM for 72 hrs) does not significantly affect the viability of BM stromal cells (BMSCs), as assessed by MTT calorimetric survival assay.

FIG. 12c is a bar chart demonstrating that co-culture of MM cells with BMSCs for 24 hrs triggers an increase in IGF-1 levels in the co-culture supernatant IGF-1 levels in the supernatant were assessed by enzyme-linked immunosorbent assay (ELISA).

FIG. 12d is a bar chart indicating that IGF-1R inhibition by ADW-742 (500 nM for 24 hrs) suppresses the constitutive and co-culture-induced secretion of VEGF by myeloma cells and BMSCs.

FIG. 12e is a bar chart indicating that ADW-742 (750 nM) suppresses the IGF-1 (200 ng/mL in serum-free medium)-induced secretion of VEGF by the SW579 papillary thyroid carcinoma cells.

Figure 13:
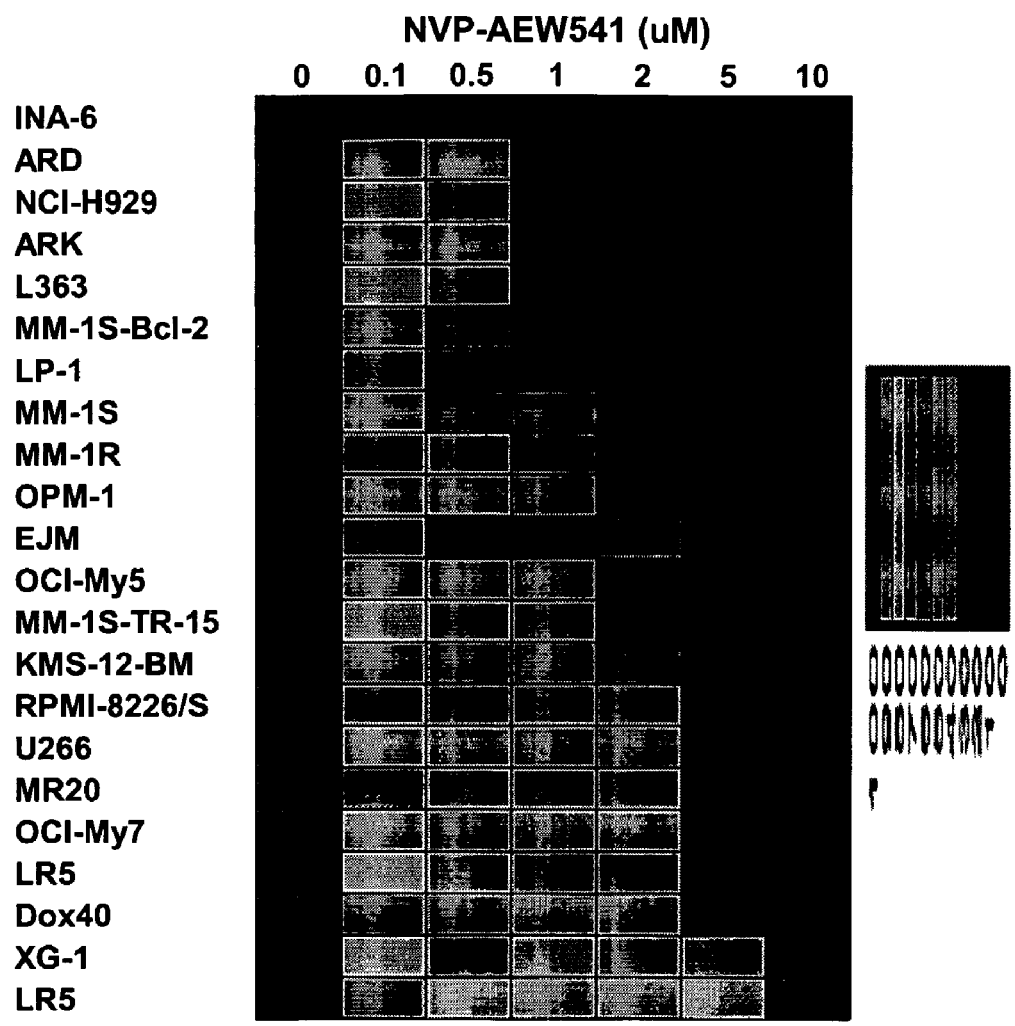

FIG. 13 is a schematic showing the comparative results of the effect of NVP-AEW541 for 72 hours on a panel of drug-sensitive and resistant MM cell lines. Results are presented as the % suppression of serum-induced increased in total population of viable tumor cells.

Figure 14:
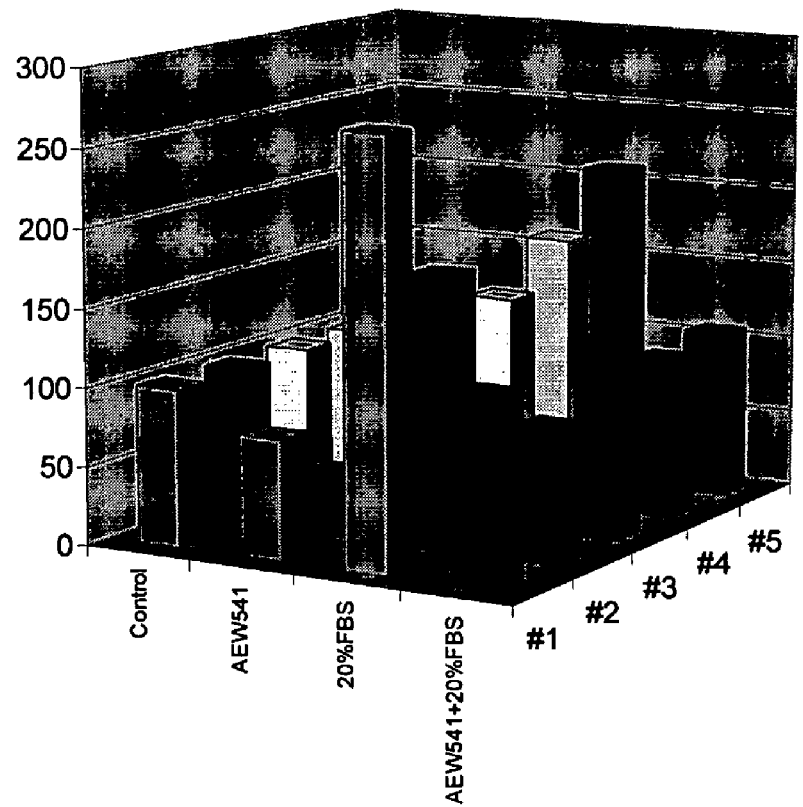

FIG. 14 is a bar chart showing in vitro activity of NVP-AEW541 against a panel of primary MM tumor cells isolated from patients resistant to conventional and investigational therapies.

Figure 15:
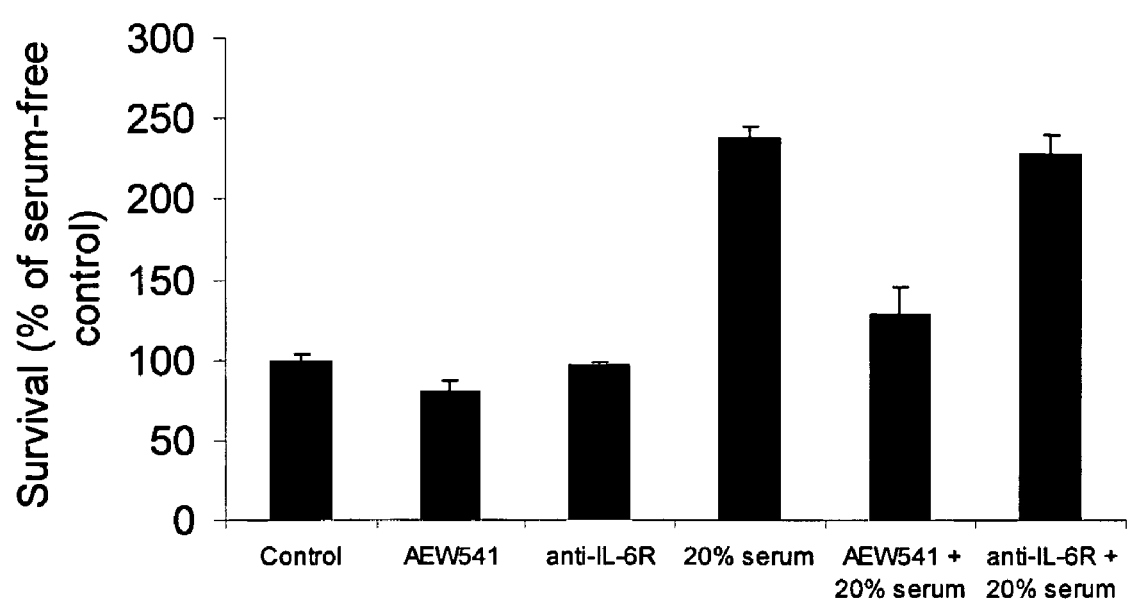

FIG. 15 is a bar chart showing in vitro activity of NVP-AEW541 (0.5 µM), and anti-IL-6R against primary MM tumor cells isolated from a patient resistant to cytotoxic chemotherapy, thalidomide, CC-5013, and PS-341.

Figure 16:
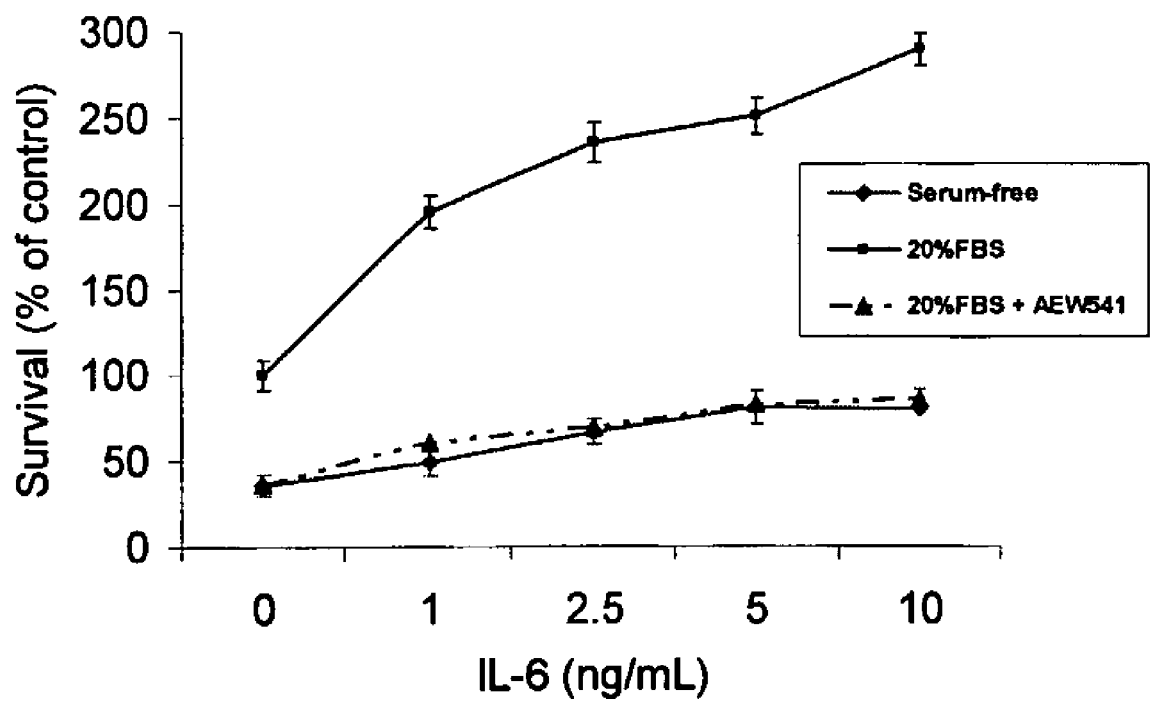

FIG. 16 is a line graph showing that IGF-1R inhibition abrogates the responsiveness of tumor cells to IL-6. In the presence of serum, primary MM cells are responsive to IL-6 at the indicated concentration as shown by MTT assays after 72 hours of incubation. However, this responsiveness is abrogated in the absence of serum or upon co-treatment with NVP-AEW541 (0.5 µM).

Figure 17:
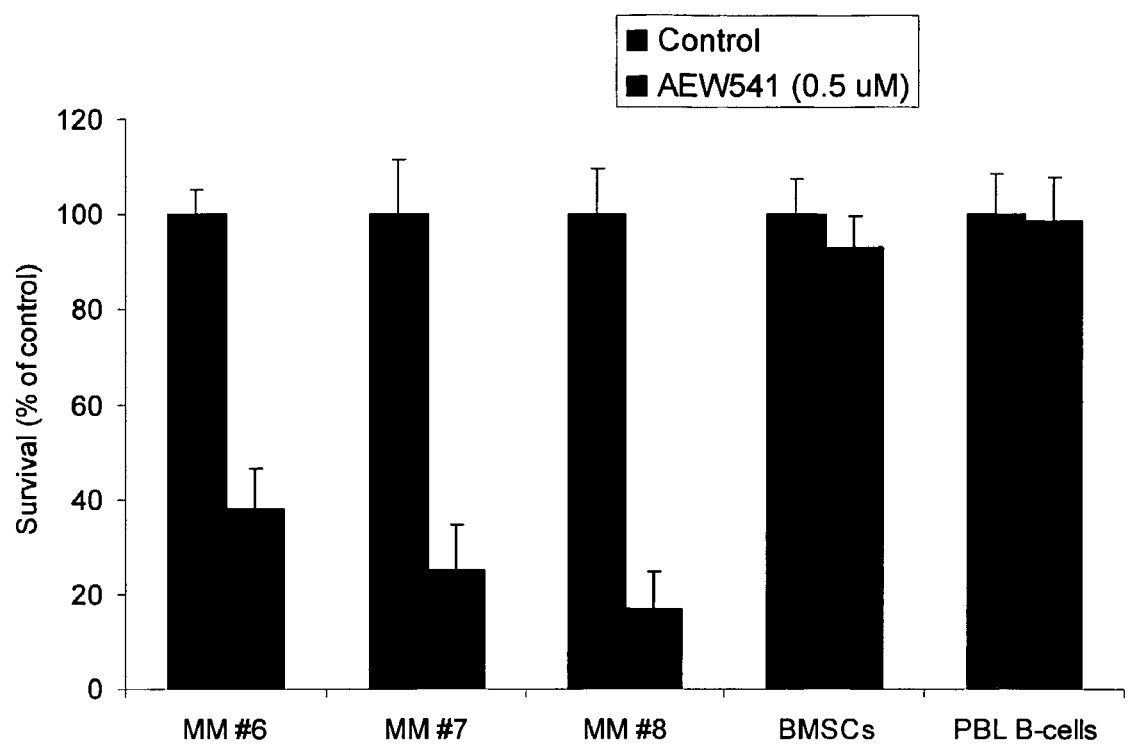

FIG. 17 is a bar chart showing the survival of primary MM cells, bone marrow stromal cells and peripheral B cells upon exposure to NVP-AEW541 (0.5 µM).

Figure 18:
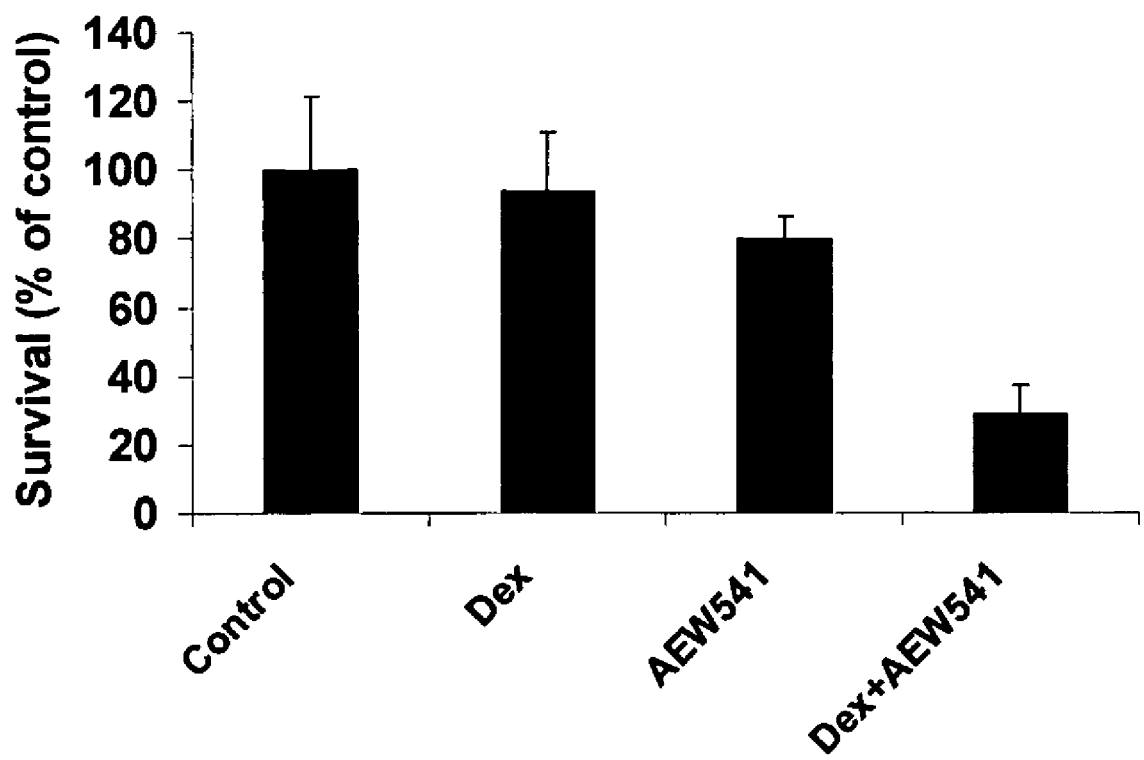

FIG. 18 is a bar chart showing MM cell survival rate in the presence of Dexamethasone (0.1 µM) or NVP-AEW541 (250 nM), alone or in combination.

Figure 19:
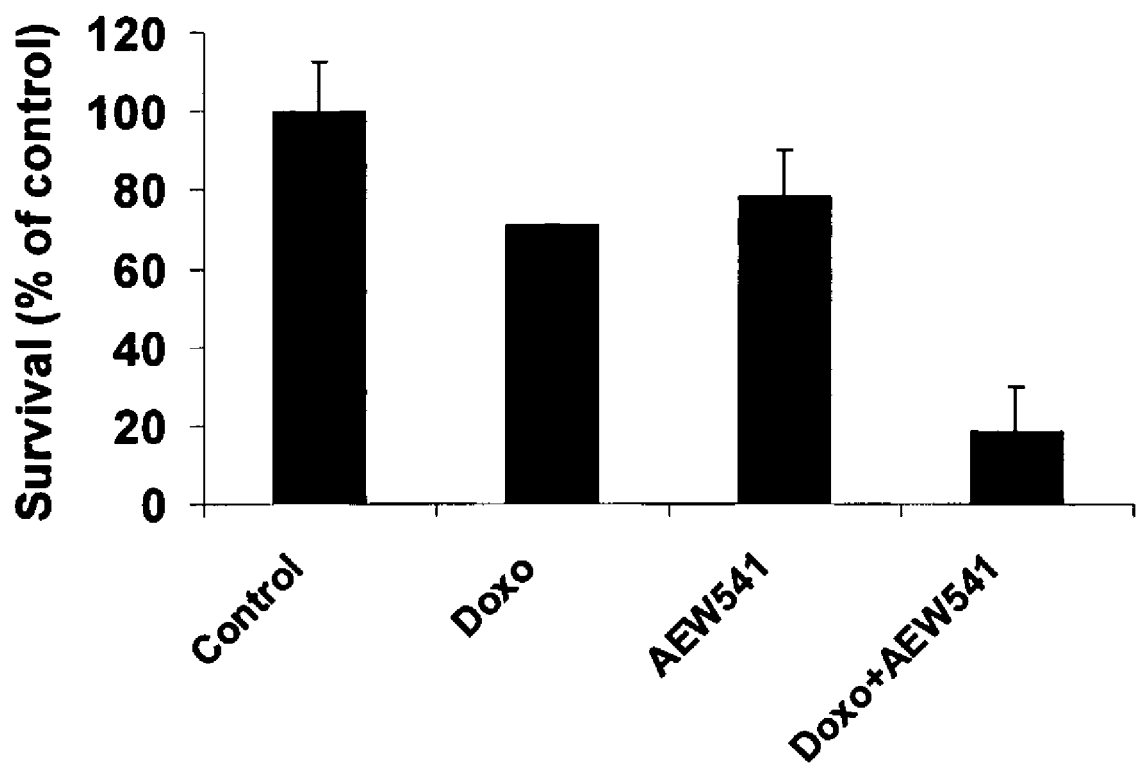

FIG. 19 is a bar chart showing MM cell survival rate in the presence of Doxorubicine at 50 ng/mL or NVP-AEW541 (250 nM) alone or in combination.

Figure 20:
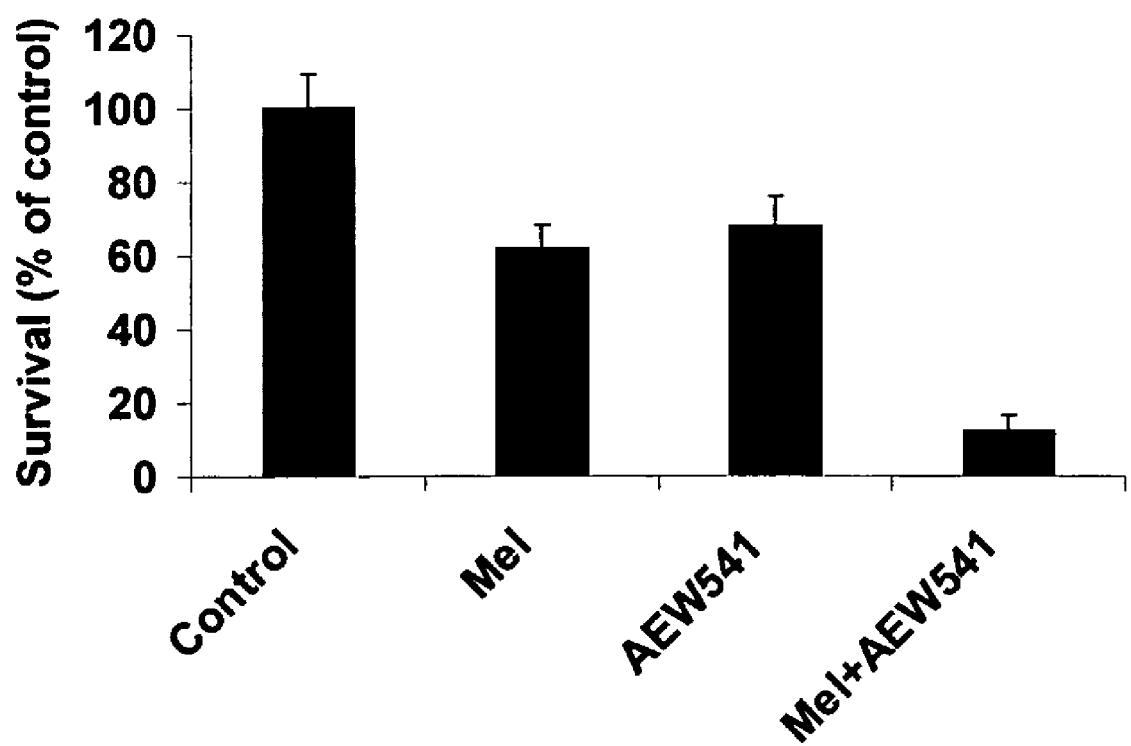

FIG. 20 is bar chart showing MM survival rate in the presence of Melphalan at (1 µM) or NVP-AEW541 (250 nM) alone or in combination.

Figure 21:
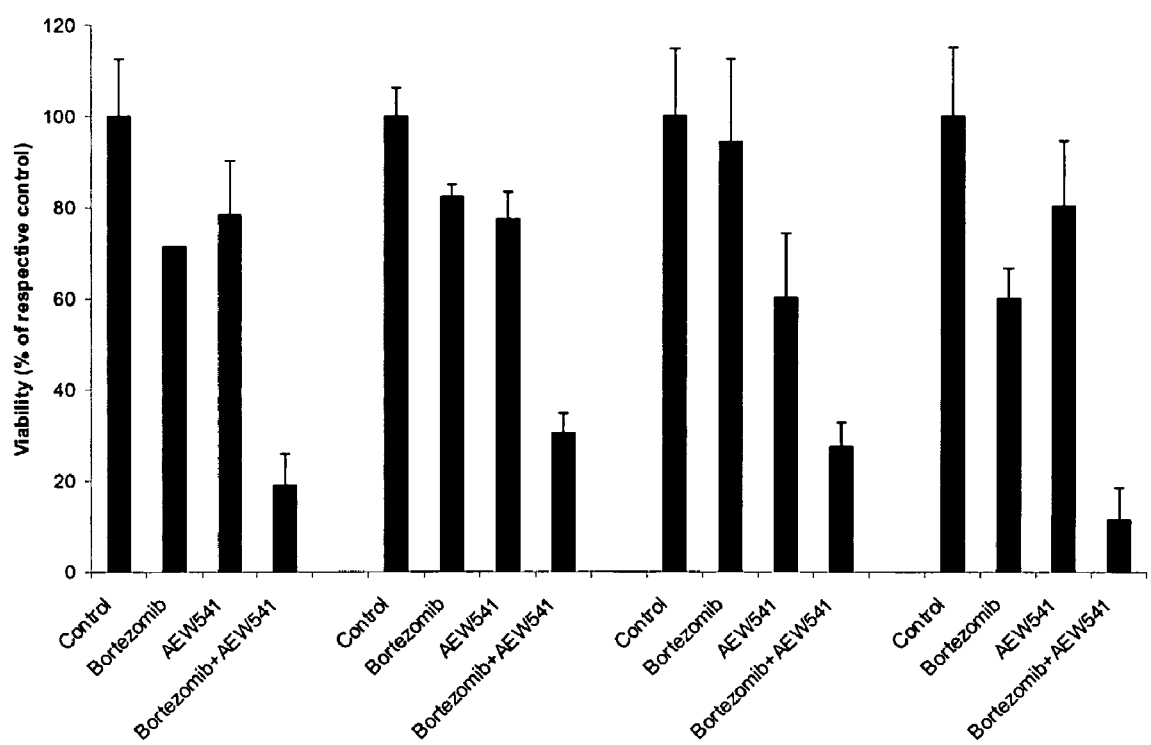

FIG. 21 is a bar chart showing the viability of MM cells in the presence of Bortezomib (5 nM) or NVP-AEW541 (250) nM alone or in combination.

Figure 22:
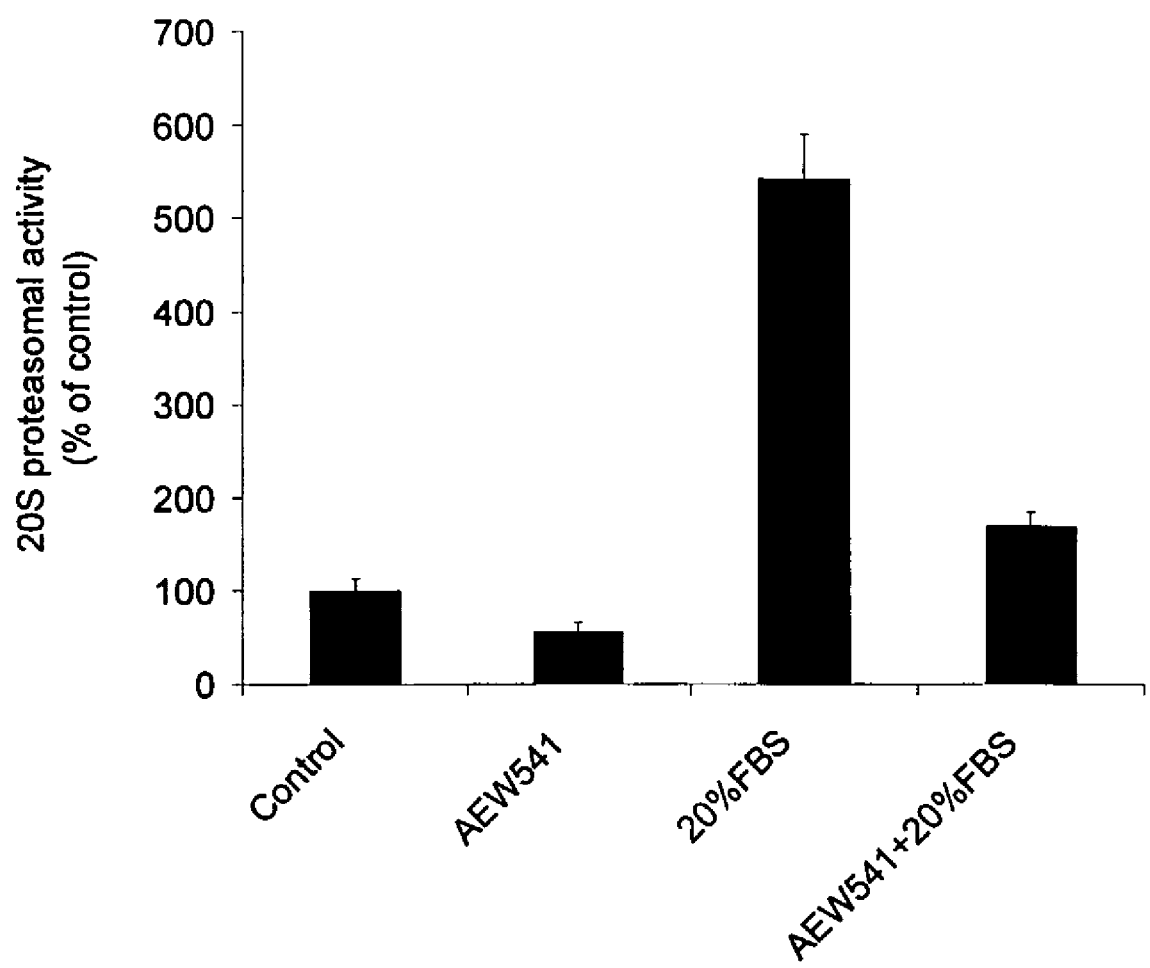

FIG. 22 is a bar chart showing the effect of NVP-AEW541 (0.5 µM) on the chemotryptic activity of the proteasome in the presence or absence of serum.

Figure 23:
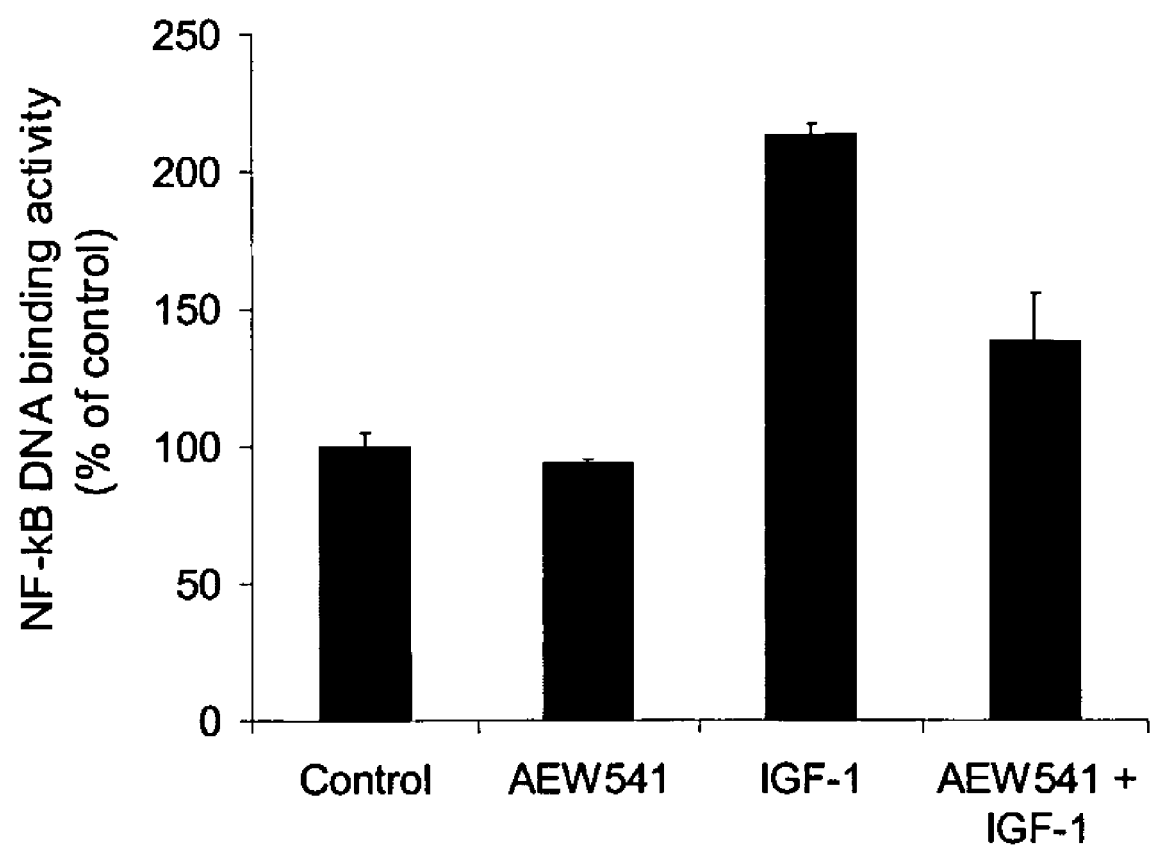

FIG. 23 is a bar chart showing the effect of NVP-AEW541 (0.5 µM) on NFkB DNA binding activity in the presence or absence of IGF-I.

Figure 24:
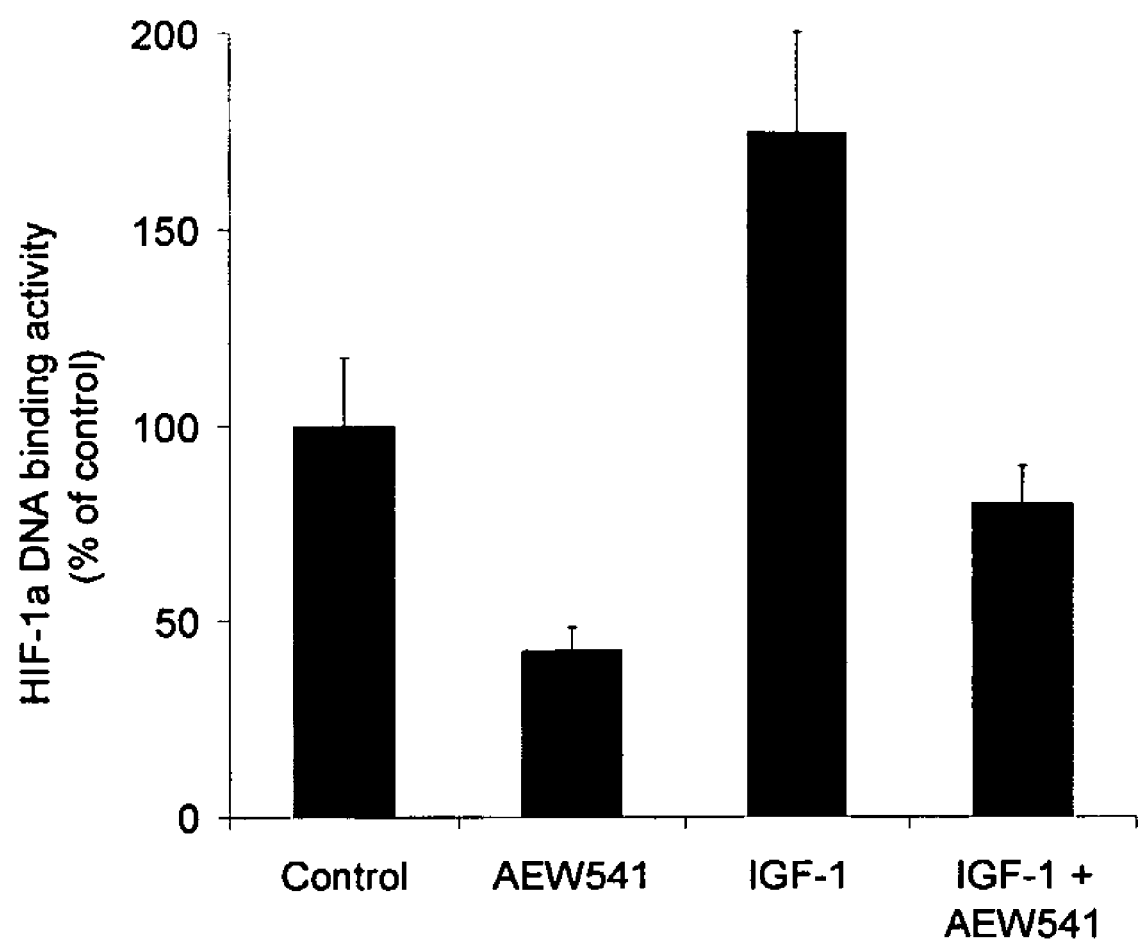

FIG. 24 is a bar chart showing the effect of NVP-AEW541 (0.5 µM) on HIF-1αDNA binding activity in the presence or absence of IGF-I.

Figure 25:
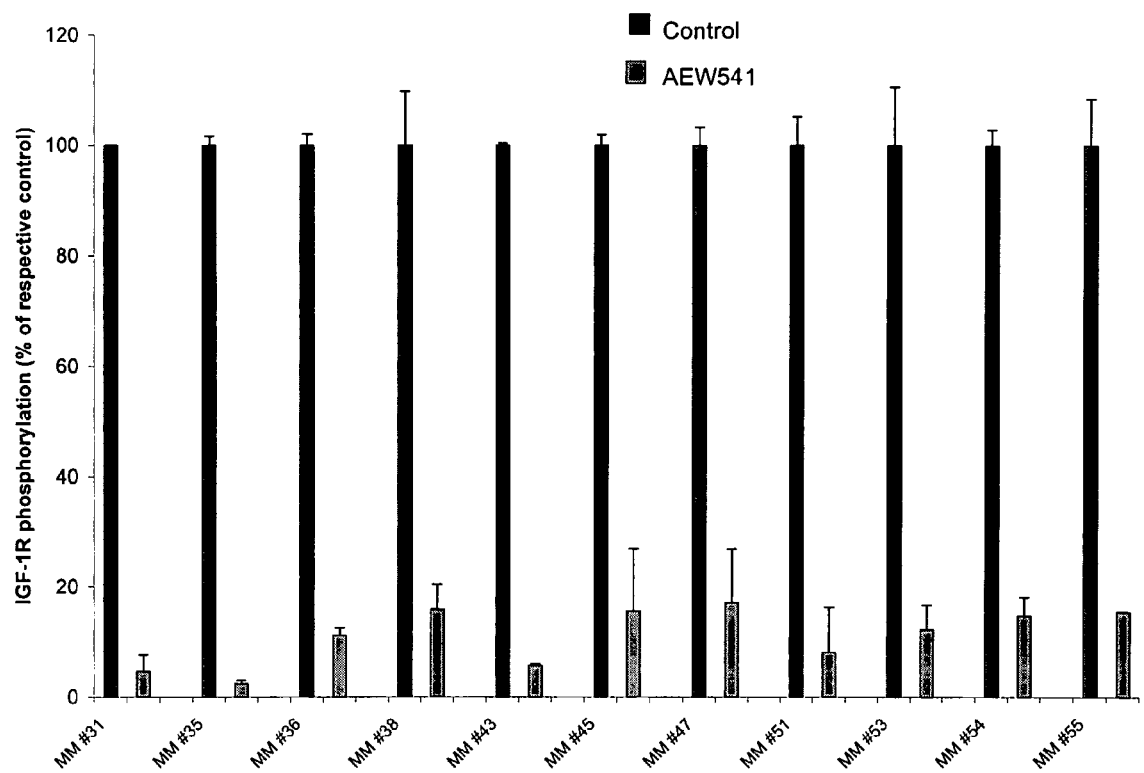

FIG. 25 is a bar chart showing inhibition of IGF-1R phosphorylation in MM cells by NVP-AEW541.

Figure 26:
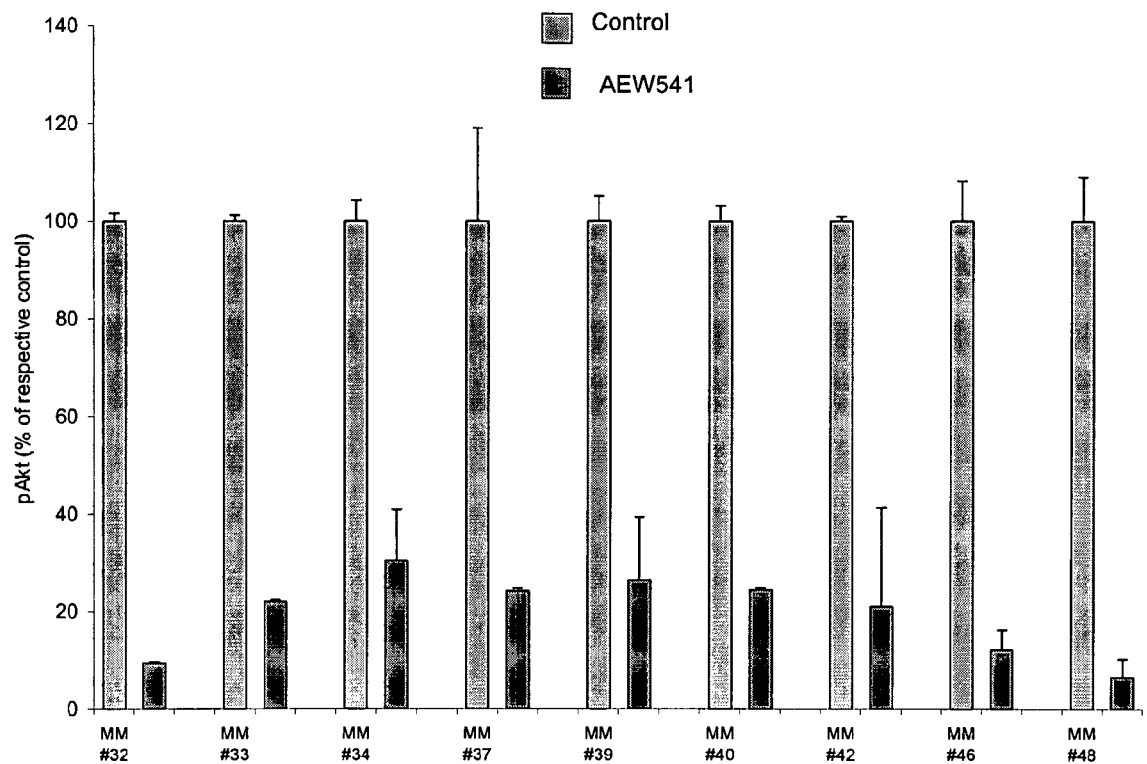

FIG. 26 is a bar chart showing inhibition of Akt phosphorylation in MM cells by NVP-AEW541.

Figure 27:
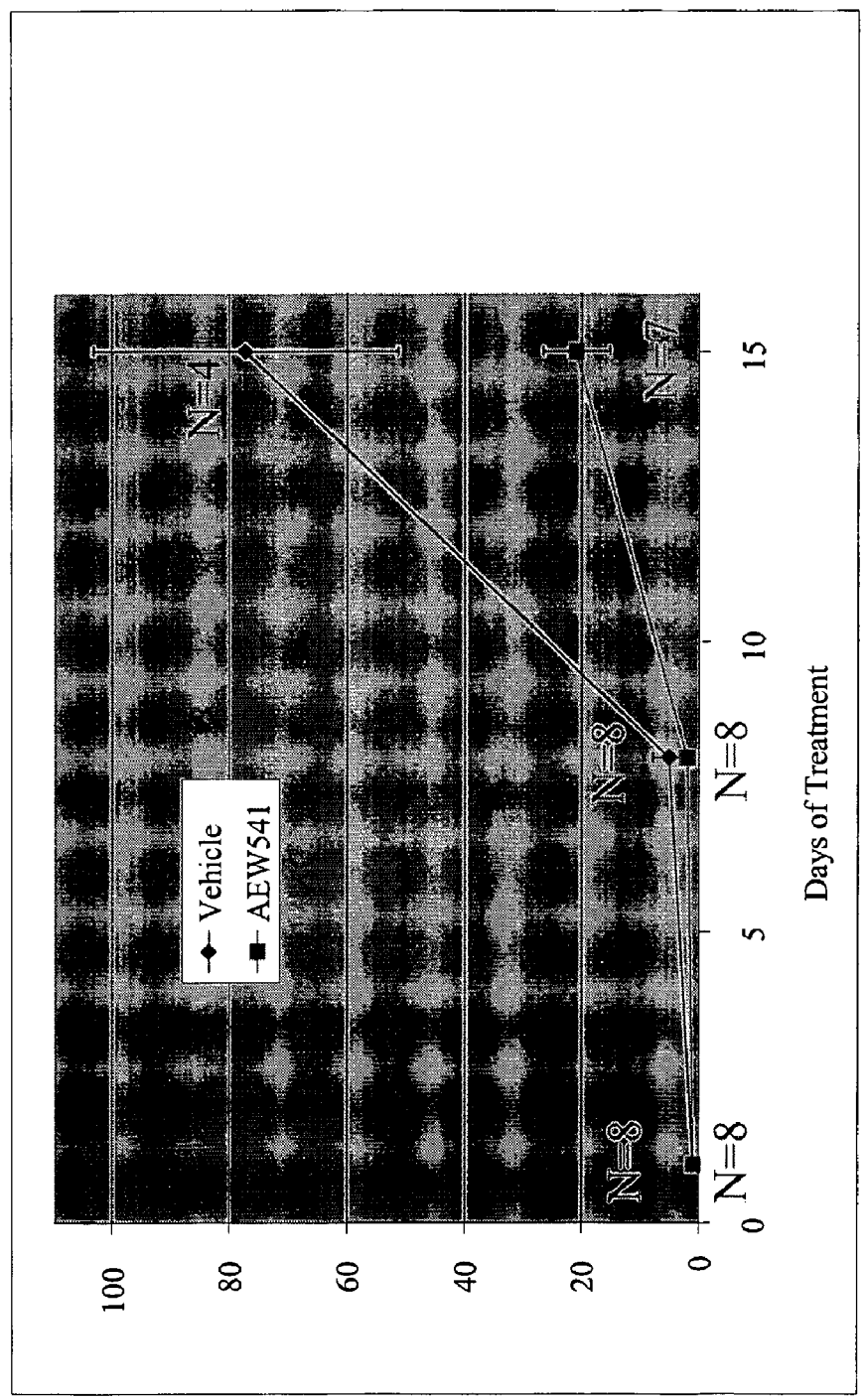

FIG. 27 is a line graph showing the effect of NVP-AEW541 in an orthotopic model of multiple myeloma. Mice with established MM1S-LucNeo disease in the bones were divided into treatment groups (n=8 per group) which received either NVP-AEW541 at 50 mg/kg PO BID, or vehicle control. Tumor burden was assessed by weekly in vivo imaging. For each animal, tumor burden is expressed relative to the baseline (day 1 of treatment), and data are expressed as mean ±SD. After 15 days of treatment, p=0.04 by student t-test.

Figure 28:
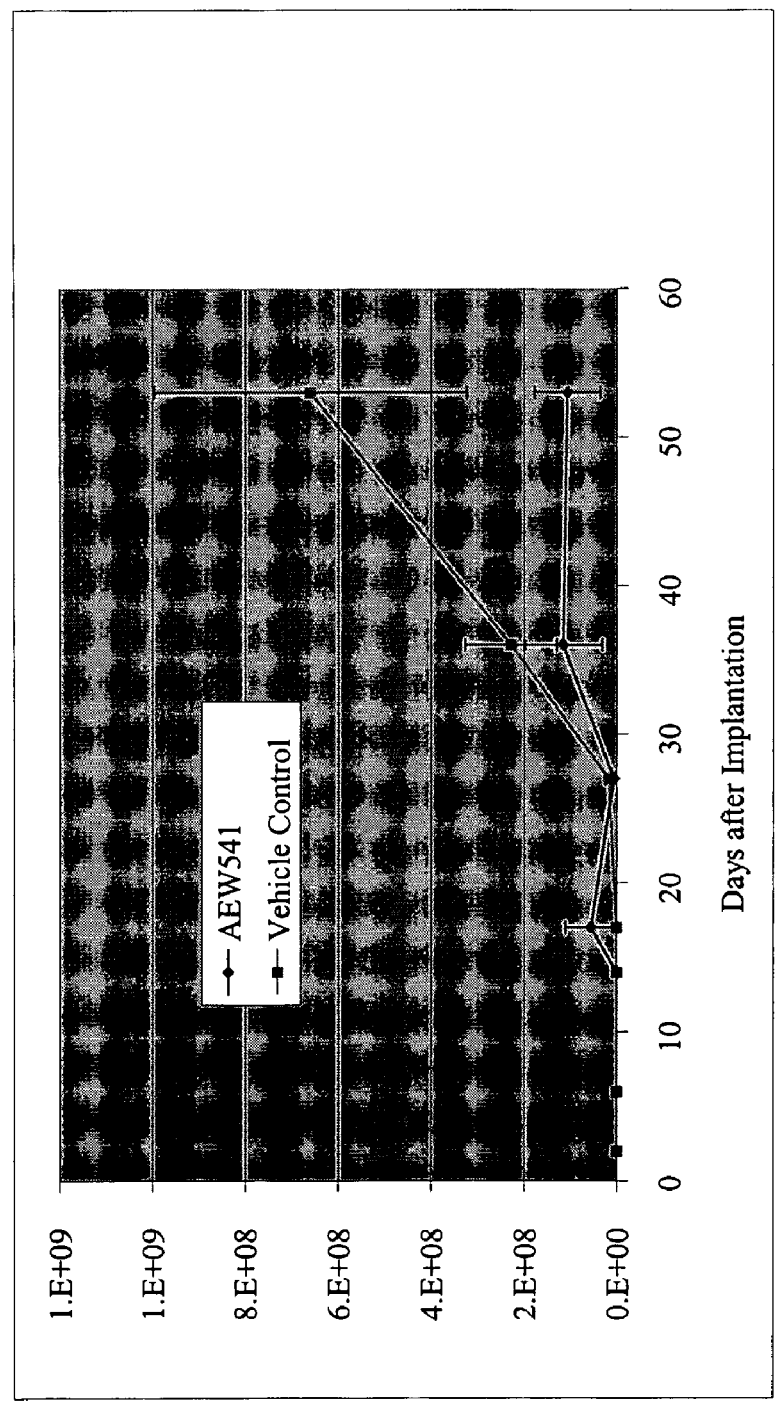
Figure 29:
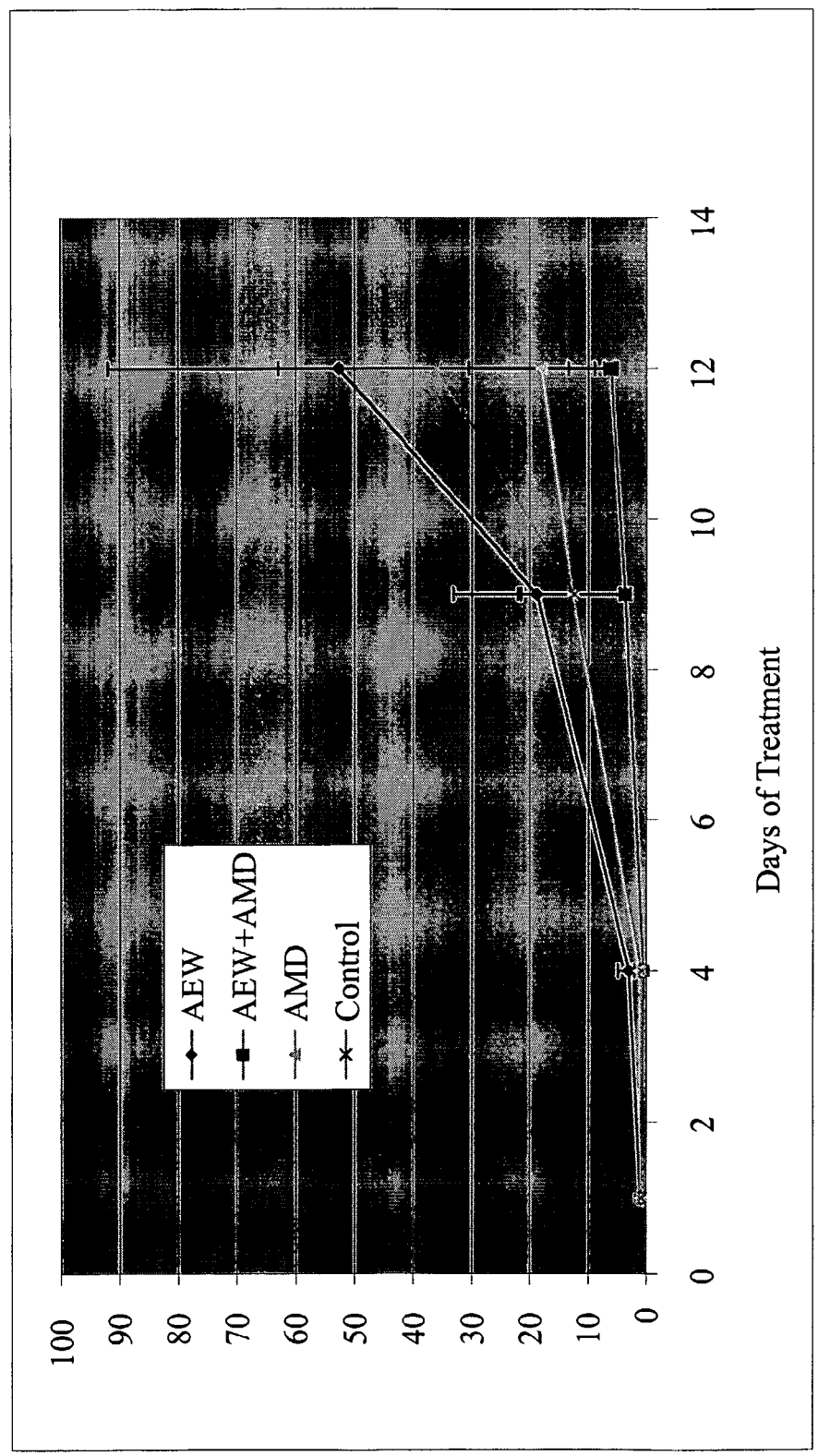

FIG. 28 is a line graph showing the effect of AEW541 on the growth of breast cancer cells FIG. 29 is a line graph showing the effect of AEW541 in combination with AMD3100 on the growth of tumor cells.

Figure 30:
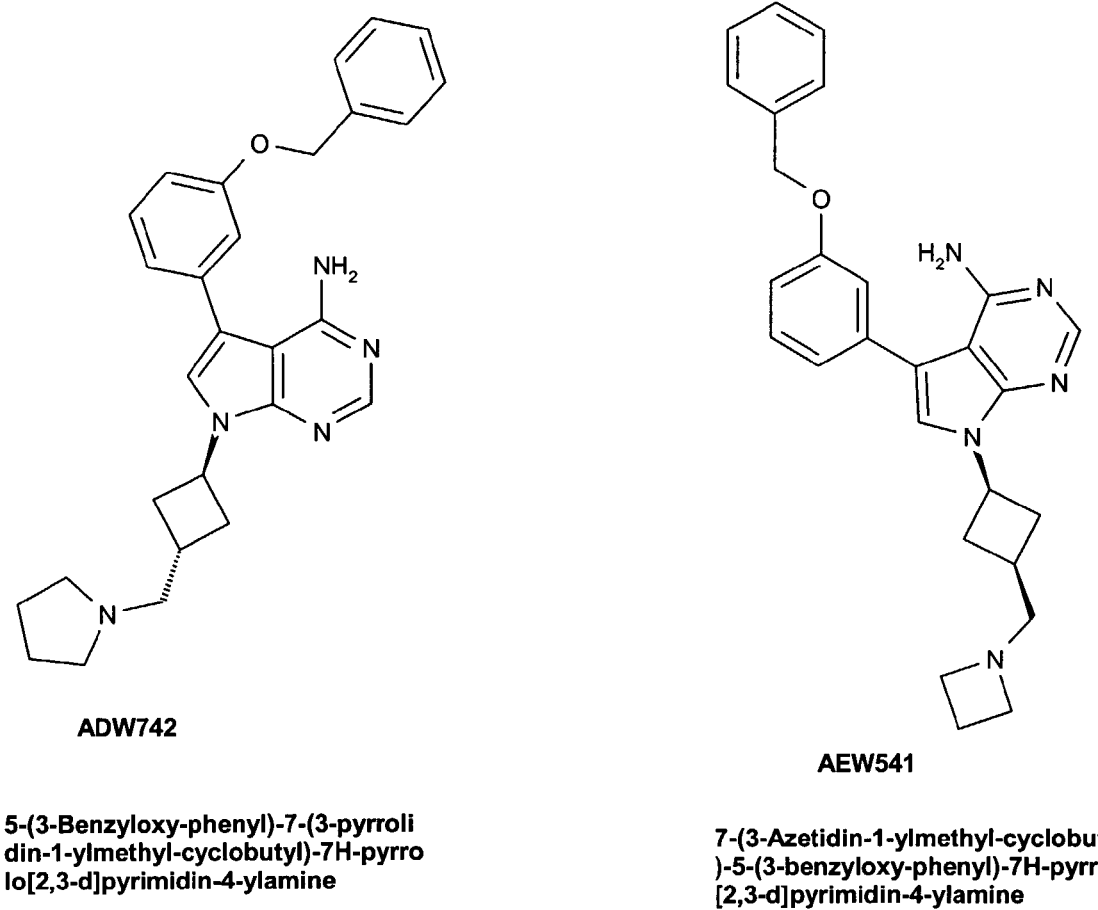

FIG. 30 is a schematic illustrating the structure and chemical formula of ADW742 and NVP-AEW541.

DETAILED DESCRIPTION OF THE INVENTION

This invention is based on the discovery that inhibitors of the insulin growth factor-1 receptor (IGF-1R) have anti-tumor activity against diverse tumor cell types in vitro, even in cells that are highly resistant to conventional or other targeted therapies.

Insulin-like growth factors-1 (IGF-1) and -2 (IGF-2) have been implicated in the pathophysiology of a wide range of human neoplasias due to the mitogenic and anti-apoptotic properties mediated by their type I receptor (IGF-1R or CD221). Expression of functional IGF-1R is required for neoplastic transformation in diverse tumorigenesis models. Until now, however, inhibition of the IGF-1R pathway had not been successfully applied as a major anti-cancer therapeutic strategy. This has been due not only to the lack of clinically-applicable small molecule inhibitors of IGF-1R function, but also to the fact that the relative impact of inhibiting the IGF/IGF-1R pathway, compared to other cytokine/growth factor cascades, in tumor cell proliferation and survival had not been fully elucidated. In addition, inhibition of IGF-1R as a strategy to treat cancer is complicated by the fact that the insulin receptor (IR) is highly homologous to the IGF-1R and most inhibitors have only a narrow differentiation between the two receptors. The present invention overcomes this deficiency in the art by demonstrating the utility of therapeutic targeting of IGF-1R function in cancer therapy and by demonstrating specific approaches to enhance the therapeutic window of IGF-1R inhibition.

Comprehensive transcriptional and proteomic analyses indicate that IGF-1R inhibition confers a pleiotropic constellation of anti-proliferative and pro-apoptotic molecular sequelae, which provides a mechanistic explanation for the ability of IGF-1R inhibitors to sensitize tumor cells to other anti-cancer drugs. IGF-1R inhibition also blunts tumor cell response to other growth factors, overcomes the drug-resistance phenotype conferred by the bone microenvironment, and abrogates the production of pro-angiogenic cytokines. In a clinically-relevant mouse model of diffuse MM, systemic administration of the selective IGF-1R tyrosine kinase inhibitor ADW-742 or NVP-AEW541 suppresses tumor growth, prolongs survival, and enhances the anti-tumor effect of cytotoxic chemotherapy. These results provide the rational for the development of clinical therapeutic strategies targeting IGF-1R.

Demonstrated herein is that IGFs in serum constitute critical promoters of tumor cell proliferation, survival and drug resistance in multiple neoplasias, and that inhibition of IGF-1R significantly suppresses these effects. Further demonstrated is the in vivo efficacy of systemic administration of one or more small molecule IGF-1R kinase inhibitors, showing that selective IGF-1R inhibition achieves in vivo anti-tumor activity with a favorable therapeutic window.

Accordingly, the invention provides methods of inhibiting tumor cell growth using IGF-1R inhibitors in combination with other therapies, such combination overcomes the previous limitation of the sole use of IGF-1R inhibitors. These methods are applicable to all therapeutic targeting of IGF-1R.

Inhibiting tumor cell growth is meant to include a decrease of the number of tumor cells entering the cell cycle, tumor cell death or the decrease of tumor cell metastasis. The tumor is a solid tumor. Alternatively, the tumor is a hematologic tumor. Tumors suitable for treatment with the methods of the invention include, but are not limited to, carcinomas, sarcomas, adenocarcinomas, lymphomas, leukemias, or multiple myeloma (MM). For example, the methods of the invention are useful for treating bone cancer, brain cancer, breast cancer, colorectal cancer, skin cancer, liver cancer, thyroid cancer, adrenal cancer, stomach cancer, kidney cancer, pancreatic cancer, lung cancer, prostate cancer, retinoblastoma.

In various aspects the invention includes administering to a subject a compound that inhibits IGF-1R expression or activity (referred to herein as IGF-1R inhibitors). A decrease of IGF-1R expression or activity is defined by a decrease of the numbers of IGF-1R molecules produced by the cell or a decrease in the tyrosine kinase activity of the IGF-1R molecule, respectively. For example, activity of an IGF-1R is measured by detecting tyrosine phosphorylation. The compound is for example: (i) small molecules such as small molecule kinase inhibitors (e.g., IGF-1R tyrosine kinase inhibitors(ii) anti-IGF1R neutralizing antibodies(e.g., anti-1R3 or JB-1), or (iii) IGF-1R receptor antagonists.

Small molecule kinase inhibitors include 4-amino-5-phenyl-7-cyclobutyl-pyrrolo[2,3-d]pyrimidine derivatives such as ADW-742, NVP-AEW541 (also referred to herein as AEW541) or analogs or isomers thereof.

Exemplary IGF-1R inhibitors include IGF-1R tyrosine kinase inhibitor and compounds falling within Formula I.

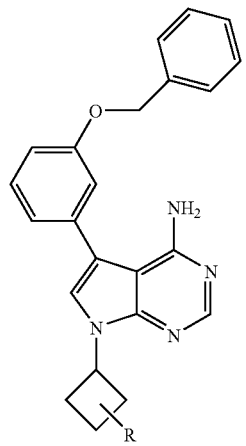

(I)

wherein

R is lower alkyl substituted by hydroxyl, unsubstituted, mono- or disubstituted amino or by a heterocyclic radical; a radical $R_1$—(C=Y)-Z-, wherein $R_1$ is unsubstituted or substituted lower alkyl, unsubstituted, mono- or disubstituted amino, a heterocyclic radical, or free or etherified hydroxy, Y is oxygen, sulfur or imino, and Z is either not present, lower alkyl or amino-lower alkyl; or a radical $R_2$-sulfonylamino-lower alkyl, wherein $R_2$ is unsubstituted or substituted lower alkyl, unsubstituted, mono- or disubstituted amino or phenyl optionally substituted by lower alkyl, lower alkoxy or nitro.

The general terms used hereinbefore and hereinafter preferably have within the context of this disclosure the following meanings, unless otherwise indicated. Where compounds of the formula I are mentioned, this is meant to include also the tautomers and N-oxides of the compounds of formula I. Where the plural form is used for compounds, salts, and the like, this is taken to mean also a single compound, salt, or the like.

Asymmetric carbon atoms of a compound of formula I that are optionally present may exist in the (R), (S) or (R,S) configuration, preferably in the (R) or (S) configuration. Substituents at a double bond or a ring may be present in cis- (=Z-) or trans (=E-) form. The compounds may thus be present as mixtures of isomers or as pure isomers, preferably as enantiomerpure diastereomers.

The prefix "lower" denotes a radical having up to and including a maximum of 7, especially up to and including a maximum of 4 carbon atoms, the radicals in question being either unbranched or branched with single or multiple branching.

Lower alkyl is for example, methyl, ethyl, n-propyl, isopropyl, n-butyl, isobutyl, sec-butyl, tert-butyl, n-pentyl, isopentyl, neopentyl, n-hexyl or n-heptyl. In R being lower alkyl substituted by unsubstituted, mono- or disubstituted amino or by a heterocyclic radical, lower alkyl is preferably methyl. Lower alkyl R is preferably methyl, isopropyl or tert-butyl.

Substituted lower alkyl is lower alkyl as defined above where one or more, preferably one, substituents may be present, such as amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidine, ureido, mercapto, lower alkylthio, halogen or a heterocyclic radical. Substituted lower alkyl R is preferably lower alkyl substituted by lower alkoxy, lower alkoxy-lower alkoxy or most preferably by a heterocyclic radical.

Halogen is primarily fluorine, chlorine, bromine, or iodine, especially fluorine, chlorine, or bromine.

Mono- or disubstituted amino is amino substituted by one or two radicals selected independently of one another from e.g. unsubstituted or substituted lower alkyl; phenyl or phenyl-lower alkyl wherein the phenyl radical is optionally substituted by e.g. unsubstituted or substituted lower alkyl, amino, N-lower alkylamino, N,N-di-lower alkylamino, N-lower alkanoylamino, N,N-di-lower alkanoylamino, hydroxyl, lower alkoxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio or halogen; adamantanyl; and a heterocyclic radical.

In R being lower alkyl substituted by mono- or disubstituted amino, mono- or disubstituted amino preferably represents N-lower alkylamino or N,N-di-lower alkylamino, respectively.

Mono- or disubstituted amino R is preferably N-lower alkylamino or N,N-di-lower alkylamino, respectively, wherein the lower alkyl moiety is optionally substituted by phenyl, lower alkyl-phenyl, lower alkoxy-phenyl, morpholinyl or N,N-di-lower alkylamino.

A heterocyclic radical contains especially up to 20 carbon atoms and is preferably a saturated or unsaturated monocyclic radical having from 4 or 8 ring members and from 1 to 3 heteroatoms which are preferably selected from nitrogen, oxygen, and sulfur, or a bi- or tri-cyclic radical wherein, for example, one or two benzene radicals are annellated (fused) to the mentioned monocyclic radical. Preferred above all, the heterocyclic radical contains at least one nitrogen ring atom whereby the binding of the heterocyclic radical to the radical of the molecule of formula I occurs via a nitrogen ring atom. The heterocyclic radical is optionally substituted by one or more, preferably by one or two, radicals such as e.g., unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio, halogen, phenyl or pyridyl. Most preferably a heterocyclic radical is azetidinyl, pyrrolidinyl, piperidyl, azepanyl, piperazinyl, tetrahydropyranyl, morpholinyl or thiomorpholinyl, wherein said radicals are optionally substituted by one or more, preferably one or two, radicals selected independently of one another from the group consisting or lower alkyl, hydroxy-lower alkyl, free or etherfied hydroxy, lower alkoxycarbonyl, carbamoyl, phenyl and pyridyl and the binding of the heterocyclic radical to the radical of the molecule of formula I occurs via a nitrogen ring atom.

In R being lower alkyl substituted by a heterocyclic radical, the heterocyclic radical preferably represents azetidinyl, pyrrolidinyl, di-lower alkyl-pyrrolidinyl, aminocarbonyl-pyrrolidinyl, piperidyl, hydroxyl-piperidyl, aminocarbonyl-piperidyl, azepanyl, lower alkyl-piperazinyl, lower alkoxylcarbonyl-piperazinyl, phenyl-piperazinyl, pyridyl-piperazinyl, morpholinyl, di-lower alkyl-morpholinyl or thiomorpholinyl.

In R being lower alkyl substituted by a heterocyclic radical, the heterocyclic radical preferably represents piperidyl, lower alkyl-piperazinyl or morpholinyl.

A heterocyclic radical $R_1$ is preferably pyrrolidinyl, piperidyl, lower alkyl-piperazinyl or morpholinyl.

Salts are especially the pharmaceutically acceptable salts of compounds of formula I (or an N-oxide thereof). Such salts are formed, for example, as acid addition salts, preferably with organic or inorganic acids, from compounds of formula I (or an N-oxide thereof) with a basic nitrogen atom, especially the pharmaceutically acceptable salts. In the presence of negatively charged radicals, such as carboxy or sulfo, salts may also be formed with bases, e.g. metal or ammonium salts, such as alkali metal or alkaline earth metal salts, or ammonium salts with ammonia or suitable organic amines, such as tertiary monoamines. In the presence of a basic group and an acid group in the same molecule, a compound of formula I (or an N-oxide thereof) may also form internal salts. For isolation or purification purposes it is also possible to use the pharmaceutically unacceptable salts, for example picrates or perchlorates. Only the pharmaceutically acceptable salts of free compounds (if the occasion arises, in the form of pharmaceutical compositions) attain therapeutic use, and these are therefore preferred.

Additional small molecule inhibitor include tyrphostin and other small molecules described by Blum et al (Biochemistry 2000, 39, 157050-15712; hereby incorporated by reference in its entirety).

Preferred IGF1 receptor inhibitors to be used in accordance with the present invention are those described in WO 02/092599 (which is hereby incorporated by reference in its entirety) and include in particular the following compounds or salts thereof.

cis-7-(3-aminomethyl-cyclobutyl)-5-(3-benzyloxy-phenyl)-7H-pyrrolo[2,3-d]pyrimidin-4-ylamine; trans-7-(3-aminomethyl-cyclobutyl)-5-(3-benzyloxy-phenyl)-7H-pyrrolo[2,3-d]pyrimidin-4-ylamine; cis-3-[4-amino-5-(3-benzyloxy-phenyl)-pyrrolo[2,3-d]pyrimidin-7-yl]-cyclobutanecarboxylic acid dimethylamide; trans-3-[4-amino-5-(3-benzyloxy-phenyl)-pyrrolo[2,3-d]pyrimidin-7-yl]-cyclobutanecarboxylic acid dimethylamide; cis-3-[4-amino-5-(3-benzyloxy-phenyl)-pyrrolo[2,3-d]pyrimidin-7-yl]-cyclobutanecarboxylic acid methylamide; trans-3-[4-amino-5-(3-benzyloxy-phenyl)-pyrrolo[2,3-d]pyrimidin-7-yl]-cyclobutanecarboxylic acid methylamide; cis-5-(3-benzyloxy-phenyl)-7-(3-dimethylaminomethyl-cyclobutyl)-7H-pyrrolo[2,3-d]pyrimidin-4-ylamine; trans-5-(3-benzyloxy-phenyl)-7-(3-dimethylaminomethyl-cyclobutyl)-7H-pyrrolo[2,3-d]pyrimidin-4-ylamine; cis-5-(3-benzyloxy-phenyl)-7-(3-methylaminomethyl-cyclobutyl)-7H-pyrrolo[2,3-d]pyrimidin-4-ylamine; trans-5-(3-benzyloxy-phenyl)-7-(3-methylaminomethyl-cyclobutyl)-7H-pyrrolo[2,3-d]pyrimidin-4-ylamine; trans-N-{3-[4-amino-5-(3-benzyloxy-phenyl)-pyrrolo[2,3-d]pyrimidin-7-yl]-cyclobutylmethyl}-guanidine; cis-N-{3-[4-amino-5-(3-benzyloxy-phenyl)-pyrrolo[2,3-d]pyrimidin-7-yl]-cyclobutylmethyl}-guanidine; trans-N-{3-[4-amino-5-(3-benzyloxy-phenyl)-pyrrolo[2,3-d]pyrimidin-7-yl]-cyclobutylmethyl}-methanesulfonamide; cis-N-{3-[4-amino-5-(3-benzyloxy-phenyl)-pyrrolo[2,3-d]pyrimidin-7-yl]-cyclobutylmethyl}-methanesulfonamide; trans-N-{3-[4-amino-5-(3-benzyloxy-phenyl)-pyrrolo[2,3-d]pyrimidin-7-yl]-cyclobutylmethyl}-4-methoxy-benzenesulfonamide; trans-N-{3-[4-amino-5-(3-benzyloxy-phenyl)-pyrrolo[2,3-d]pyrimidin-7-yl]-cyclobutylmethyl}-4-methyl-benzenesulfonamide; trans-N-{3-[4-amino-5-(3-benzyloxy-phenyl)-pyrrolo[2,3-d]pyrimidin-7-yl]-cyclobutylmethyl}-4-nitrobenzenesulfonamide; propane-2-sulfonic acid trans-{3-[4-amino-5-(3-benzyloxy-phenyl)-pyrrolo[2,3-d]pyrimidin-7-yl]-cyclobutylmethyl}-amide; ethanesulfonic acid trans-{3-[4-amino-5-(3-benzyloxy-phenyl)-pyrrolo[2,3-d]pyrimidin-7-yl]-cyclobutylmethyl}-amide; N-dimethyl-sulfamide trans-{3-[4-amino-5-(3-benzyloxy-phenyl)-pyrrolo[2,3-d]pyrimidin-7-yl]-cyclobutylmethyl}-amide; N-dimethyl-sulfamide cis-{3-[4-amino-5-(3-benzyloxy-phenyl)-pyrrolo[2,3-d]pyrimidin-7-yl]-cyclobutylmethyl}-amide; trans-{3-[4-amino-5-(3-benzyloxy-phenyl)-pyrrolo[2,3-d]pyrimidin-7-yl]-cyclobutylmethyl}-carbamic acid methyl ester; cis-{3-[4-amino-5-(3-benzyloxy-phenyl)-pyrrolo[2,3-d]pyrimidin-7-yl]-cyclobutylmethyl}-carbamic acid methyl ester; trans-{3-[4-amino-5-(3-benzyloxy-phenyl)-pyrrolo[2,3-d]pyrimidin-7-yl]-cyclobutylmethyl}-carbamic acid 2-methoxy-ethyl ester; cis-{3-[4-amino-5-(3-benzyloxy-phenyl)-pyrrolo[2,3-d]pyrimidin-7-yl]-cyclobutylmethyl}-carbamic acid 2-methoxy-ethyl ester; trans-1-{3-[4-amino-5-(3-benzyloxy-phenyl)-pyrrolo[2,3-d]pyrimidin-7-yl]-cyclobutylmethyl}-3-ethyl-urea; cis-{3-[4-amino-5-(3-benzyloxy-phenyl)-pyrrolo[2,3-d]pyrimidin-7-yl]-cyclobutylmethyl}-3-ethyl-urea; trans-1-{3-[4-amino-5-(3-benzyloxy-phenyl)-pyrrolo[2,3-d]pyrimidin-7-yl]-cyclobutylmethyl}-3-propyl-urea; cis-1-{3-[4-amino-5-(3-benzyloxy-phenyl)-pyrrolo[2,3-d]pyrimidin-7-yl]-cyclobutylmethyl}-3-propyl-urea; trans-1-{3-[4-amino-5-(3-benzyloxy-phenyl)-pyrrolo[2,3-d]pyrimidin-7-yl]-cyclobutylmethyl}-3-isopropyl-urea; cis-1-{3-[4-amino-5-(3-benzyloxy-phenyl)-pyrrolo[2,3-d]pyrimidin-7-yl]-cyclobutylmethyl}-3-isopropyl-urea; trans-1-{3-[4-amino-5-(3-benzyloxy-phenyl)-pyrrolo[2,3-d]pyrimidin-7-yl]-cyclobutylmethyl}-3-butyl-urea; cis-1-{3-[4-amino-5-(3-benzyloxy-phenyl)-pyrrolo[2,3-d]pyrimidin-7-yl]-cyclobutylmethyl}-3-butyl-urea; trans-1-{3-[4-amino-5-(3-benzyloxy-phenyl)-pyrrolo[2,3-d]pyrimidin-7-yl]-cyclobutylmethyl}-3-tert-butyl-urea; cis-1-{3-[4-amino-5-(3-benzyloxy-phenyl)-pyrrolo[2,3-d]pyrimidin-7-yl]-cyclobutylmethyl}-3-tert-butyl-urea; trans-1-{3-[4-amino-5-(3-benzyloxy-phenyl)-pyrrolo[2,3-d]pyrimidin-7-yl]-cyclobutylmethyl}-3-benzyl-urea; trans-1-{3-[4-amino-5-(3-benzyloxy-phenyl)-pyrrolo[2,3-d]pyrimidin-7-yl]-cyclobutylmethyl}-3-(3-methyl-benzyl)-urea; cis-1-{3-[4-amino-5-(3-benzyloxy-phenyl)-pyrrolo[2,3-d]pyrimidin-7-yl]-cyclobutylmethyl}-3-(3-methyl-benzyl)-urea; cis-1-{3-[4-amino-5-(3-benzyloxy-phenyl)-pyrrolo[2,3-d]pyrimidin-7-yl]-cyclobutylmethyl}-3-(4-methoxy-benzyl)-urea; trans-1-{3-[4-amino-5-(3-benzyloxy-phenyl)-pyrrolo[2,3-d]pyrimidin-7-yl]-cyclobutylmethyl}-3-(2-morpholin-4-yl-ethyl)-urea; cis-1-{3-[4-amino-5-(3-benzyloxy-phenyl)-pyrrolo[2,3-d]pyrimidin-7-yl]-cyclobutylmethyl}-3-(2-morpholin-4-yl-ethyl)-urea; trans-1-{3-[4-amino-5-(3-benzyloxy-phenyl)-pyrrolo[2,3-d]pyrimidin-7-yl]-cyclobutylmethyl}-3-(2-dimethylamino-ethyl)-urea; cis-1-{3-[4-amino-5-(3-benzyloxy-phenyl)-pyrrolo[2,3-d]pyrimidin-7-yl]-cyclobutylmethyl}-3-(2-dimethylamino-ethyl)-urea; trans-1-{3-[4-amino-5-(3-benzyloxy-phenyl)-pyrrolo[2,3-d]pyrimidin-7-yl]-cyclobutylmethyl}-3-(3-morpholin-4-yl-propyl)-urea; cis-1-{3-[4-amino-5-(3-benzyloxy-phenyl)-pyrrolo[2,3-d]pyrimidin-7-yl]-cyclobutylmethyl}-3-(3-morpholin-4-yl-propyl)-urea; trans-1-{3-[4-amino-5-(3-benzyloxy-phenyl)-pyrrolo[2,3-d]pyrimidin-7-yl]-cyclobutylmethyl}-3-(3-dimethylamino-propyl)-urea; cis-1-{3-[4-amino-5-(3-benzyloxy-phenyl)-pyrrolo[2,3-d]pyrimidin-7-yl]-cyclobutylmethyl}-3-(3-dimethylamino-propyl)-urea; trans-{3-[4-amino-5-(3-benzyloxy-phenyl)-pyrrolo[2,3-d]pyrimidin-7-yl]-cyclobutylmethyl}-urea; cis-{3-[4-amino-5-(3-benzyloxy-phenyl)-pyrrolo[2,3-d]pyrimidin-7-yl]-cyclobutylmethyl}-urea; trans-N-{3-[4-amino-5-(3-benzyloxy-phenyl)-pyrrolo[2,3-d]pyrimidin-7-yl]-cyclobutylmethyl}-acetamide; cis-N-{3-[4-amino-5-(3-benzyloxy-phenyl)-pyrrolo[2,3-d]pyrimidin-7-yl]-cyclobutylmethyl}-acetamide; trans-N-{3-[4-amino-5-(3-benzyloxy-phenyl)-pyrrolo[2,3-d]pyrimidin-7-yl]-cyclobutylmethyl}-isobutyramide; cis-N-{3-[4-amino-5-(3-benzyloxy-phenyl)-pyrrolo[2,3-d]pyrimidin-7-yl]-cyclobutylmethyl}-isobutyramide; trans-N-{3-[4-amino-5-(3-benzyloxy-phenyl)-pyrrolo[2,3-d]pyrimidin-7-yl]-cyclobutylmethyl}-2,2-dimethyl-propionamide; cis-N-{3-[4-amino-5-(3-benzyloxy-phenyl)-pyrrolo[2,3-d]pyrimidin-7-yl]-cyclobutylmethyl}-2,2-dimethyl-propionamide; trans-N-{3-[4-amino-5-(3-benzyloxy-phenyl)-pyrrolo[2,3-d]pyrimidin-7-yl]-cyclobutylmethyl}-2-piperidin-1-yl-acetamide; cis-N-{3-[4-amino-5-(3-benzyloxy-phenyl)-pyrrolo[2,3-d]pyrimidin-7-yl]-cyclobutylmethyl}-2-piperidin-1-yl-acetamide; trans-N-{3-[4-amino-5-(3-benzyloxy-phenyl)-pyrrolo[2,3-d]pyrimidin-7-yl]-cyclobutylmethyl}-2-morpholin-4-yl-acetamide; cis-N-{3-[4-amino-5-(3-benzyloxy-phenyl)-pyrrolo[2,3-d]pyrimidin-7-yl]-cyclobutylmethyl}-2-morpholin-4-yl-acetamide; trans-N-{3-[4-amino-5-(3-benzyloxy-phenyl)-pyrrolo[2,3-d]pyrimidin-7-yl]-cyclobutylmethyl}-2-(4-methyl-piperazin-1-yl)-acetamide; cis-N-{3-[4-amino-5-(3-benzyloxy-phenyl)-pyrrolo[2,3-d]pyrimidin-7-yl]-cyclobutylmethyl}-2-(4-methyl-piperazin-1-yl)-acetamide; trans-5-(3-benzyloxy-phenyl)-7-(3-morpholin-4-ylmethyl-cyclobutyl)-7H-pyrrolo[2,3-d]pyrimidin-4-ylamine; trans-5-(3-benzyloxy-phenyl)-7-(3-piperidin-1-ylmethyl-cyclobutyl)-7H-pyrrolo[2,3-d]pyrimidin-4-ylamine; trans-5-(3-benzyloxy-phenyl)-7-(3-pyrrolidin-1-ylmethyl-cyclobutyl)-7H-pyrrolo[2,3-d]pyrimidin-4-ylamine (ADW); trans-5-(3-benzyloxy-phenyl)-7-[3-(4-methyl-piperazin-1-ylmethyl)-cyclobutyl]-7H-pyrrolo[2,3-d]pyrimidin-4-ylamine; trans-7-[3-(adamantan-1-ylaminomethyl)-cyclobutyl]-5-(3-benzyloxy-phenyl)-7H-pyrrolo[2,3-d]pyrimidin-4-ylamine; trans-1-{3-[4-amino-5-(3-benzyloxy-phenyl)-pyrrolo[2,3-d]pyrimidin-7-yl]-cyclobutylmethyl}-piperidin-4-ol; trans-7-(3-azepan-1-ylmethyl-cyclobutyl)-5-(3-benzyloxy-phenyl)-7H-pyrrolo[2,3-d]pyrimidin-4-ylamine; trans-5-(3-benzyloxy-phenyl)-7-[3-(2,5-dimethyl-pyrrolidin-1-ylmethyl)-cyclobutyl]-7H-pyrrolo[2,3-d]pyrimidin-4-ylamine; trans-7-(3-azetidin-1-ylmethyl-cyclobutyl)-5-(3-benzyloxy-phenyl)-7H-pyrrolo[2,3-d]pyrimidin-4-ylamine; trans-1-{3-[4-amino-5-(3-benzyloxy-phenyl)-pyrrolo[2,3-d]pyrimidin-7-yl]-cyclobutylmethyl}-piperidine-3-carboxylic acid amide; trans-5-(3-benzyloxy-phenyl)-7-[3-(4-pyridin-2-yl-piperazin-1-ylmethyl)-cyclobutyl]-7H-pyrrolo[2,3-d]pyrimidin-4-ylamine; trans-5-(3-benzyloxy-phenyl)-7-(3-thiomorpholin-4-ylmethyl-cyclobutyl)-7H-pyrrolo[2,3-d]pyrimidin-4-ylamine; trans-5-(3-benzyloxy-phenyl)-7-[3-(2,6-dimethyl-morpholin-4-ylmethyl)-cyclobutyl]-7H-pyrrolo[2,3-d]pyrimidin-4-ylamine; trans-(S)-1-{3-[4-amino-5-(3-benzyloxy-phenyl)-pyrrolo[2,3-d]pyrimidin-7-yl]-cyclobutylmethyl}-pyrrolidine-2-carboxylic acid amide; cis-7-(3-azepan-1-ylmethyl-cyclobutyl)-5-(3-benzyloxy-phenyl)-7H-pyrrolo[2,3-d]pyrimidin-4-ylamine; cis-1-{3-[4-amino-5-(3-benzyloxy-phenyl)-pyrrolo[2,3-d]pyrimidin-7-yl]-cyclobutylmethyl}-piperidin-4-ol; cis-4-{3-[4-amino-5-(3-benzyloxy-phenyl)-pyrrolo[2,3-d]pyrimidin-7-yl]-cyclobutylmethyl}-piperazine-1-carboxylic acid ethyl ester; cis-5-(3-benzyloxy-phenyl)-7-[3-(4-phenyl-piperazin-1-ylmethyl)-cyclobutyl]-7H-pyrrolo[2,3-d]pyrimidin-4-ylamine; cis-5-(3-benzyloxy-phenyl)-7-[3-(4-methyl-piperazin-1-ylmethyl)-cyclobutyl]-7H-pyrrolo[2,3-d]pyrimidin-4-ylamine; cis-5-(3-benzyloxy-phenyl)-7-(3-thiomorpholin- 4-ylmethyl-cyclobutyl)-7H-pyrrolo[2,3-d]pyrimidin-4-ylamine; cis-5-(3-benzyloxy-phenyl)-7-[3-(2,6-dimethyl-morpholin-4-ylmethyl)-cyclobutyl]-7H-pyrrolo[2,3-d]pyrimidin-4-ylamine; cis-(R)-1-{3-[4-amino-5-(3-benzyloxy-phenyl)-pyrrolo[2,3-d]pyrimidin-7-yl]-cyclobutylmethyl}-pyrrolidine-2-carboxylic acid amide; cis-1-{3-[4-amino-5-(3-benzyloxy-phenyl)-pyrrolo[2,3-d]pyrimidin-7-yl]-cyclobutylmethyl}-piperidine-3-carboxylic acid amide; trans-N-{3-[4-amino-5-(3-benzyloxy-phenyl)-pyrrolo[2,3-d]pyrimidin-7-yl]-cyclobutylmethyl}-2-ethoxy-acetamide; trans-N-{3-[4-amino-5-(3-benzyloxy-phenyl)-pyrrolo[2,3-d]pyrimidin-7-yl]-cyclobutylmethyl}-2-(2-methoxy-ethoxy)-acetamide; trans-1-{3-[4-amino-5-(3-benzyloxy-phenyl)-pyrrolo[2,3-d]pyrimidin-7-yl]-cyclobutylmethyl}-3-methyl-urea; cis-1-{3-[4-amino-5-(3-benzyloxy-phenyl)-pyrrolo[2,3-d]pyrimidin-7-yl]-cyclobutylmethyl}-3-methyl-urea; trans-pyrrolidine-1-carboxylic acid {3-[4-amino-5-(3-benzyloxy-phenyl)-pyrrolo[2,3-d]pyrimidin-7-yl]-cyclobutylmethyl}-amide; trans-piperidine-1-carboxylic acid {3-[4-amino-5-(3-benzyloxy-phenyl)-pyrrolo[2,3-d]pyrimidin-7-yl]-cyclobutylmethyl}-amide; trans-morpholine-4-carboxylic acid {3-[4-amino-5-(3-benzyloxy-phenyl)-pyrrolo[2,3-d]pyrimidin-7-yl]-cyclobutylmethyl}-amide; trans-3-{3-[4-amino-5-(3-benzyloxy-phenyl)-pyrrolo[2,3-d]pyrimidin-7-yl]-cyclobutylmethyl}-1,1-dimethyl-urea; trans-4-methyl-piperazine-1-carboxylic acid {3-[4-amino-5-(3-benzyloxy-phenyl)-pyrrolo[2,3-d]pyrimidin-7-yl]-cyclobutylmethyl}-amide; trans-3-{3-[4-amino-5-(3-benzyloxy-phenyl)-pyrrolo[2,3-d]pyrimidin-7-yl]-cyclobutylmethyl}-1,1-diethyl-urea; trans-{3-[4-amino-5-(3-benzyloxy-phenyl)-pyrrolo[2,3-d]pyrimidin-7-yl]-cyclobutylmethyl}-carbamic acid 2-diethylamino-ethyl ester; trans-{3-[4-amino-5-(3-benzyloxy-phenyl)-pyrrolo[2,3-d]pyrimidin-7-yl]-cyclobutylmethyl}-carbamic acid 2-morpholin-4-yl-ethyl ester; trans-{3-[4-amino-5-(3-benzyloxy-phenyl)-pyrrolo[2,3-d]pyrimidin-7-yl]-cyclobutylmethyl}-carbamic acid 2-(4-methyl-piperazin-1-yl)-ethyl ester; trans-{3-[4-amino-5-(3-benzyloxy-phenyl)-pyrrolo[2,3-d]pyrimidin-7-yl]-cyclobutylmethyl}-carbamic acid 2-dimethylamino-ethyl ester; trans-{3-[4-amino-5-(3-benzyloxy-phenyl)-pyrrolo[2,3-d]pyrimidin-7-yl]-cyclobutylmethyl}-carbamic acid ethyl ester; trans-4-{3-[4-amino-5-(3-benzyloxy-phenyl)-pyrrolo[2,3-d]pyrimidin-7-yl]-cyclobutylmethyl}-piperazine-1-carboxylic acid ethyl ester; cis-5-(3-benzyloxy-phenyl)-7-(3-pyrrolidin-1-ylmethyl-cyclobutyl)-7H-pyrrolo[2,3-d]pyrimidin-4-ylamine; cis-7-(3-azetidin-1-ylmethyl-cyclobutyl)-5-(3-benzyloxy-phenyl)-7H-pyrrolo[2,3-d]pyrimidin-4-ylamine; trans-3-[4-Amino-5-(3-benzyloxy-phenyl)-6-bromo-pyrrolo[2,3-d]pyrimidin-7-yl]-cyclobutanecarboxylic acid methylester; trans-3-[4-Amino-5-(3-benzyloxy-phenyl)-6-methyl-pyrrolo[2,3-d]pyrimidin-7-yl]-cyclobutanecarboxylic acid methyl ester; trans-{3-[4-Amino-5-(3-benzyloxy-phenyl)-6-methyl-pyrrolo[2,3-d]pyrimidin-7-yl]-cyclobutyl}-methanol; cis-3-[4-Amino-5-(3-benzyloxy-phenyl)-6-bromo-pyrrolo[2,3-d]pyrimidin-7-yl]-cyclobutanecarboxylic acid methyl ester; cis-3-[4-Amino-5-(3-benzyloxy-phenyl)-6-methyl-pyrrolo[2,3-d]pyrimidin-7-yl]-cyclobutanecarboxylic acid methyl ester; cis-{3-[4-Amino-5-(3-benzyloxy-phenyl)-6-methyl-pyrrolo[2,3-d]pyrimidin-7-yl]-cyclobutyl}-methanol; cis-3-[4-Amino-5-(3-benzyloxy-phenyl)-6-ethyl-pyrrolo[2,3-d]pyrimidin-7-yl]-cyclobutanecarboxylic acid methyl ester; trans-3-[4-Amino-5-(3-benzyloxy-phenyl)-6-ethyl-pyrrolo[2,3-d]pyrimidin-7-yl]-cyclobutanecarboxylic acid methyl ester; cis-{3-[4-Amino-5-(3-benzyloxy-phenyl)-6-ethyl-pyrrolo[2,3-d]pyrimidin-7-yl]-cyclobutyl}-methanol; trans-{3-[4-Amino-5-(3-benzyloxy-phenyl)-6-ethyl-pyrrolo[2,3-d]pyrimidin-7-yl]-cyclobutyl}-methanol; trans-5-(3-Benzyloxy-phenyl)-6-methyl-7-(3-pyrrolidin-1-ylmethyl-cyclobutyl)-7H-pyrrolo[2,3-d]pyrimidin-4-ylamine; trans-5-(3-Benzyloxy-phenyl)-6-methyl-7-[3-(4-methyl-piperazin-1-ylmethyl)-cyclobutyl]-7H-pyrrolo[2,3-d]pyrimidin-4-ylamine; trans-1-{3-[4-Amino-5-(3-benzyloxy-phenyl)-6-methyl-pyrrolo[2,3-d]pyrimidin-7-yl]-cyclobutylmethyl}-piperidin-4-ol; trans-7-(3-Azetidin-1-ylmethyl-cyclobutyl)-5-(3-benzyloxy-phenyl)-6-methyl-7H-pyrrolo[2,3-d]pyrimidin-4-ylamine; trans-5-(3-Benzyloxy-phenyl)-1-methyl-7-{3-[(tetrahydro-pyran-4-ylamino)-methyl]-cyclobutyl}-7H-pyrrolo[2,3-d]pyrimidin-4-ylamine; trans-((R)-1-{3-[4-Amino-5-(3-benzyloxy-phenyl)-6-methyl-pyrrolo[2,3-d]pyrimidin-7-yl]-cyclobutylmethyl}-pyrrolidin-2-yl)-methanol; cis-5-(3-Benzyloxy-phenyl)-6-methyl-7-(3-pyrrolidin-1-ylmethyl-cyclobutyl)-7H-pyrrolo[2,3-d]pyrimidin-4-ylamine; cis-5-(3-Benzyloxy-phenyl)-6-methyl-7-[3-(4-methyl-piperazin-1-ylmethyl)-cyclobutyl]-7H-pyrrolo[2,3-d]pyrimidin-4-ylamine; cis-7-(3-Azetidin-1-ylmethyl-cyclobutyl)-5-(3-benzyloxy-phenyl)-6-methyl-7H-pyrrolo[2,3-d]pyrimidin-4-ylamine; cis-1-{3-[4-Amino-5-(3-benzyloxy-phenyl)-6-methyl-pyrrolo[2,3-d]pyrimidin-7-yl]-cyclobutylmethyl}-piperidin-4-ol; cis-((R)-1-{3-[4-Amino-5-(3-benzyloxy-phenyl)-1-methyl-pyrrolo[2,3-d]pyrimidin-7-yl]-cyclobutylmethyl}-pyrrolidin-2-yl)-methanol; cis-5-(3-Benzyloxy-phenyl)-6-ethyl-7-(3-pyrrolidin-1-ylmethyl-cyclobutyl)-7H-pyrrolo[2,3-d]pyrimidin-4-ylamine; cis-5-(3-Benzyloxy-phenyl)-6-ethyl-7-[3-(4-methyl-piperazin-1-ylmethyl)-cyclobutyl]-7H-pyrrolo[2,3-d]pyrimidin-4-ylamine; cis-7-(3-Azetidin-1-ylmethyl-cyclobutyl)-6-ethyl-5-{3-[(Z)-2-eth-(E)-ylidene-hexa-3,5-dienyloxy]-phenyl}-7H-pyrrolo[2,3-d]pyrimidin-4-ylamine; cis-1-{3-[4-Amino-5-(3-benzyloxy-phenyl)-6-ethyl-pyrrolo[2,3-d]pyrimidin-7-yl]-cyclobutylmethyl}-piperidin-4-ol; cis-((R)-1-{3-[4-Amino-5-(3-benzyloxy-phenyl)-6-ethyl-pyrrolo[2,3-d]pyrimidin-7-yl]-cyclobutylmethyl}-pyrrolidin-2-yl)-methanol; and cis-5-(3-Benzyloxy-phenyl)-6-ethyl-7-{3-[(tetrahydro-pyran-4-ylamino)-methyl]-cyclobutyl}-7H-pyrrolo[2,3-d]pyrimidin-4-ylamine. Among these compounds trans-5-(3-benzyloxy-phenyl)-7-(3-pyrrolidin-1-ylmethyl-cyclobutyl)-7H-pyrrolo[2,3-d]pyrimidin-4-ylamine (ADW-742) is most especially preferred. The preparation of these compounds is described in WO 02/092599.

The subject is a mammal such as human, a primate, mouse, rat, dog, cat, cow, horse, pig. The subject is suffering from or at risk of developing a tumor.

Methods of Inhibiting Tumor Growth

IGF-1R Inhibition in Combination with Cytotoxic or Chemotherapeutic Therapy

Tumor cell growth is inhibited by administering to a subject a cytotoxic or chemotherapeutic agent and a composition containing an IGF-1R inhibitor. The IGF-1R inhibitor is administered after the cytotoxic agent or the chemotherapeutic agent. Alternatively, the IGF-1R inhibitor is administered before the cytotoxic agent or the chemotherapeutic agent. The IGF-1R inhibitor is administered within 1 week after the cytotoxic agent or the chemotherapeutic agent. For example, the IGF-1R inhibitor is administered less than 72, 48, 24 or 12 hours after the cytotoxic agent or the chemotherapeutic agent. Preferably, the IGF-1R inhibitor is administered within 3-12 hours after the cytotoxic agent or the chemotherapeutic agent. Optionally, the IGF-1R inhibitor is administered concomitantly with the cytotoxic agent or the chemotherapeutic agent.

Administration of the IGF-1R inhibitor is in a single dose. Alternatively, administration is in multiple doses, e.g. 1, 2, 3, 4 or 5 or more doses. Optionally, the inhibitor is administered over a preselected period of time. For example, the inhibitor is administered over about 1-2 days.

A cytotoxic agent is any agent that is harmful to cell structure and function, and which may ultimately cause cell death. For example a cytotoxic agent is a chemotherapeutic agent or radiation therapy. A chemotherapeutic agent is any agent that is used to treat cancer. A chemotherapeutic agent includes alkylating agents (e.g., chlorambucil, cyclophosphamide, thiotepa, and busulfan); anti-metabolites agents (e.g., purine antagonists, pyrimidine antagonists, and folate antagonists); mitoic inhibitor such as plant alkaloids (e.g., actinomycin D, doxorubicin, mitomycin, paclitaxel, docetaxel, etoposide (VP-16), vinblastine, vincristine, and vinorelbine); anti-tumor antibiotics (e.g., bleomycin, dactinomycin, daunorubicin, doxorubicin (Adriamycin®), idarubicin, and mitoxantrone); proteasome inhibitors (e.g. bortezomib), corticosteroids hormones (e.g., prednisone and dexamethasone); sex hormones (e.g., anti-estrogens (tamoxifen, fulvestrant), aromatase inhibitors (anastrozole, letrozole), progestins (megestrol acetate), anti-androgens (bicalutamide, flutamide), and LHRH agonists (leuprolide, goserelin). Other chemotherapuetic agents include L-asparaginase and tretinoin, cyclophosphamide, or Cytoxan® (C) methotrexate (M)), 5-flourouracil, or 5-FU (F), Adriamycin® (A) and Taxol® (T), prednisone 5-fluorouracil, capecitabine, methotrexate, gemcitabine, cytarabine (ara-C), and fludarabine.

Cytotoxic/chemotherapeutic therapy is administered using standard protocols for a particular tumor type. Standard protocols are known in the art. For example, the cytotoxic or chemotherapeutic agent is administered orally; intravenously, intramuscularly, subcutaneously or intrathecally. Two or more methods of administration may be used at the same time under certain circumstances.

The IGF-1R inhibitor and the cytotoxic/chemotherapeutic agents are administered at standard therapeutic doses. Alternatively, IGF-1R inhibitor and the cytotoxic/chemotherapeutic agents are administered at sub-therapeutic doses. By "standard therapeutic doses" is meant the dose at which a therapeutic effect of the compound is detected when the particular compound is administered singularly. For example, a standard therapeutic dose of an IGF-1R inhibitor is a dose which can potentially achieve clinical benefit as a single agent and/or modulate glucose homeostasis resulting in, for example, hyperglycemia, ketosis or glucosuria in the patient to which the inhibitor is administered. Similarly, a standard therapeutic dose of a cytotoxic/chemotherapeutic compound is the dose at which the compound confers a clinical benefit. A clinical benefit is alleviation of one or more symptoms of the particular cancer, such as tumor size or metastasis.

A "sub-therapeutic dose" includes doses at which a therapeutic effect of the compound is not detected when the particular compound is administered singularly.

Optionally, the IGF-1R inhibitor is administered in an amount sufficient to cause perturbations of glucose metabolism, clinical manifestations of which include hyperglycemia, ketosis, and glucosuria.

Enhancing IGF-1R Inhibition by Lowering IGF Levels

In another aspect, tumor growth is inhibited by administering to a subject an IGF-1R inhibitor in combination with a compound that lowers the concentration of IGFs, e.g., IGF-1 or IGF-2. IGFs are produced by many different tissue types such as the liver, the bone marrow or the tumor. The majority of IGF-1 in the serum is produced by the liver and is growth hormone-dependent.

The compound lowers the concentration of IGF systemically (i.e, serum concentration). Alternatively, IGF concentration is lowered locally (i.e., specific microenvironment of the tumor) By decreasing the systemic or local concentration of ligands of the IGF-1R, inhibition of the IGF-1R is enhanced, thus lowering the amount or IGF-1R inhibitor required, in turn decreasing the associated side effects of IGF-1R inhibition.

Measurement of IGF levels in, e.g., serum or the tumor microenvironment, is accomplished by assays known to one of ordinary skill in the art, including radioimmunoassays (RIA), ELISA, RT-PCR, immunohistochemical localization of IGF-1 in tissue (e.g., biopsy material).

Reduction of IGF levels in a subject is performed by methods known in the art, including administration of small molecules, and inhibition of IGF transcription and/or translation. For example, IGF-1 levels are reduced by somatostatin and analogs thereof, by inhibitors of growth hormone production, by agents which decrease growth hormone bioavailability, by inhibitors of the growth hormone receptor and/or by inhibitors of signaling cascades downstream of the growth hormone receptor. Somatostatin analogs include octreotide (SMS 201-995), lanreotide, depreotide, vapreotide (RC-160), somatuline (BIM 23014), TT-232, AN-238. Other suitable somatostatin analogs are those disclosed in U.S. Pat. No. 6,465,613 the contents of which are hereby incorporated by reference. Inhibitors of growth hormone production include antisense oligodeoxynucleotides (ODNs) or small inhibitory RNA (siRNA) against the mRNA transcript for the growth hormone molecule. Agents which decrease growth hormone bioavailability include neutralizing antibodies against growth hormone, soluble growth hormone receptors or other proteins which can be engineered to bind growth hormone with higher affinity than its receptor in target tissues. Inhibitors of the growth hormone receptor include neutralizing antibodies, inhibitory peptides or small molecule inhibitors which prevent growth hormone from binding to its receptor and/or activating its downstream signaling pathways in target tissues. Inhibitors of growth hormone receptor downstream signaling cascade include antisense ODNs, siRNA constructs, peptides, small molecule inhibitors or other strategies that can block the signaling pathways which are stimulated by growth hormone receptor and which can lead to increased production of IGFs.

IGF-1 transcription is inhibited, for example, by targeting nucleotide sequences complementary to the regulatory region of the IGF nucleic acid (e.g., the IGF-1 promoter and/or enhancers) to form triple helical structures that prevent transcription of the IGF-1 gene in target cells. See, e.g., Helene, 1991. *Anticancer Drug Des.* 6: 569-84; Helene, et al. 1992. *Ann. N.Y. Acad. Sci.* 660: 27-36; Maher, 1992. *Bioassays* 14: 807-15 (the contents of which are incorporated by reference in their entireties.

Alternatively, IGF translation is inhibited by an antisense nucleic acid, such as a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585-591) can be used to catalytically cleave IGF-1 mRNA transcripts to thereby inhibit translation of IGF-1 mRNA. A ribozyme having specificity for an IGF-1-encoding nucleic acid can be designed based upon the nucleotide sequence of an IGF-1 cDNA. For example, a derivative of a *Tetrahymena* L-19 IVS RNA can be constructed in which the nucleotide sequence of the active site is complementary to the nucleotide sequence to be cleaved in an IGF-1-encoding mRNA. See, e.g., U.S. Pat. No. 4,987,071 to Cech, et al. and U.S. Pat. No. 5,116,742 to Cech, et al. IGF-1 mRNA can also be used to select a catalytic RNA having a specific ribonuclease activity from a pool of RNA molecules. See, e.g., Bartel et al., (1993) *Science* 261:1411-1418.

Exemplary nucleic acids encoding IGFs include for example human IGF-1 available as GENBANK™ Accession Nos. AY790940; CR541861; X05113; AY260957; or E02872 or human IGF-2 available as GENBANK™ Accession Nos. S62621; T29467; T27620; L15440; AH002704; M22373; or M22372.

The order of administration of the IGF-1R inhibitor and the compound that lowers the concentration of IGF, and the duration of the administration, will determine the efficacy of the anti-tumor treatment. In some aspects of the invention, it is advantageous to administer an IGF-1R inhibitor and a compound that lowers the concentration of IGF concomitantly. Alternatively, in other aspects of the invention, it is advantageous to administer the IGF1-R inhibitor after the compound that lowers the concentration of IGF, i.e., 3-12 hours, about 12 hours, about 24 hours, or about 48 hours after administration of the compound that lowers the concentration of IGF.

IGF-1R Inhibition in Combination with Anti-Diabetic Therapy

Administration of compounds that inhibit IGF-1R may also potentially inhibit the insulin receptor, resulting in aberrant glucose homeostasis, hyperglycemia and diabetes. Increased efficacy of inhibition of IGF-1R activity can be achieved by preventing or reducing the diabetic complications. Accordingly, in another aspect of the invention tumor growth is inhibited by administering to a subject an IGF-1R inhibitor in combination with an anti-diabetic agent.

As used herein, an "anti-diabetic agent" includes any agent that, when provided in an effective dose, reduces, inhibits, or prevents one or more clinically-relevant symptoms of diabetes. Symptoms of diabetes include aberrant glucose homeostasis, increased thirst and urination, weight loss, wasting of muscles, blurred vision, hunger, fatigue, frequent infections, numbness or tingling in the hands and feet, dry skin, headache, slow healing of wounds.

Anti-diabetic agents include but are not limited to: (i) exogenously-administered insulin; (ii) agents that enhance insulin sensitivity (e.g., thiazolidinediones (e.g., rosiglitazone (AVANDIA®), pioglitazone (ACTOS®), troglitazone, and ciglitazone); and biguanides (e.g., metformin (GLUCOPHAGE®; GLUCOPHAGE® XR))); (iii) agents that enhance secretion of insulin (insulin secretagogues; e.g., sulphonylureas, such as gliclazide, tolbutamide, glimepiride, glibenclamide, tolazamide, and repaglinide; meglitinides; imidazolines such as efaroxan; and rapid-acting insulin secretagogues (e.g., nateglinide and repaglinide); and alpha-glucosidase inhibitors (e.g., acarbose (PRECOSE®), miglitol (GLYSET®)).

The anti-diabetic agent is administered concomitantly, before, or after administration of the IGF-1R inhibitor. Optionally, the anti-diabetic agent is administered for a preselected period of time before or after the administration of the IGF-1R inhibitor. Alternatively, the anti-diabetic agent is administered when evidence of glucose intolerance becomes apparent, and titrated to ameliorate signs and symptoms of hyperglycemia.

Enhancing IGF-1R Inhibition Decreasing Expression or Activity of the IGF-1R

IGFs (i.e., IGF-1 or IGF-2) mediate tumor cell proliferation and resistance to apoptosis through signaling of IGF-1R. The responsiveness of tumor cells to IGFs is significantly influenced by the expression of signaling-competent IGF-1R on the surface of tumor cells, thus tumor cell growth is inhibited by interference with tumor cell expression or activity of the IGF-1R.

Accordingly, in another aspect of the invention tumor cell growth is inhibited by administering to a subject a composition that includes a compound that decreases the expression (i.e., on the cell surface) or activity of the IGF-1R. Optionally, the composition further includes an IGF-1R inhibitor.

IGF-1R expression or activity is decreased by suppressing IGF-1R gene transcription. Inhibition of IGF-1R transcription is accomplished, for example, by targeting nucleotide sequences complementary to the regulatory region of the IGF-1R nucleic acid (e.g., the IGF-1R promoter and/or enhancers) to form triple helical structures that prevent transcription of the IGF-1R gene in target cells. See, e.g., Helene, 1991. *Anticancer Drug Des.* 6: 569-84; Helene, et al. 1992. *Ann. N. Y Acad. Sci.* 660: 27-36; Maher, 1992. *Bioassays* 14: 807-15. Alternatively, IGF-1R gene transcription is decreased by increasing the activity of negative regulators of the IGF-1R gene promoter.

Inhibition of IGF-1R translation is accomplished for example by an antisense IGF-1R nucleic acid, an IGF-1R-specific small-interfering RNA, or an IGF-1R-specific ribozyme IGF-1R gene expression can be attenuated by RNA interference. One approach well-known in the art is small interfering RNA (siRNA) mediated gene silencing where expression products of an IGF-1R gene are targeted by specific double stranded IGF-1R-derived siRNA nucleotide sequences that are complementary to at least a 19-25 nt long segment of the IGF-1R gene transcript, including the 5' untranslated (UT) region, the ORF, or the 3' UT region. See, e.g., PCT applications WO00/44895, WO99/32619, WO01/75164, WO01/92513, WO 01/29058, WO01/89304, WO02/16620, and WO02/29858, each incorporated by reference herein in their entirety. Targeted genes are an IGF-1R gene, or an upstream or downstream modulator of an IGF-1R gene. Nonlimiting examples of upstream or downstream modulators of an IGF-1R gene include, e.g. a transcription factor that binds the IGF-1R gene promoter, a kinase or phosphatase that interacts with an IGF-1R polypeptide, and polypeptides involved in a IGF-1R signaling pathway.

Ribozymes are used to catalytically cleave IGF-1R mRNA transcripts to thereby inhibit translation of IGF-1R mRNA. A ribozyme having specificity for an IGF-1R-encoding nucleic acid is designed based upon the nucleotide sequence of an IGF-1R cDNA by methods known in the art. Alternately, IGF-1R mRNA is be used to select a catalytic RNA having a specific ribonuclease activity from a pool of RNA molecules. See, e.g., Bartel et al., (1993) *Science* 261:1411-1418.

Exemplary nucleic acids encoding IGFRs include for example human IGFRs available as GENBANK™ Accession Nos. NM000875, NM00876, NM04215 or AF064078.

Additionally, compound that inhibit IGF-1R expression or activity include compounds that (i) inhibit the proteolytic processing of precursor IGF-1R; (ii) prevent intracellular trafficking of newly synthesized IGF-1R from the endoplasmic reticulum to the cell surface; (iii) interfere with post-translational covalent modification (e.g., glycosylation or lipid conjugation) of the IGF-1R protein; (iv) disrupt the proper three-dimensional confirmation of the IGF-1R; (v) prevent the docking of adapter proteins to the intracellular domains of the IGF-1R; (vi) enhance internalization,, ubiquination or degradation of IGF-1R.

Methods of Reducing Angiogenesis

Angiogenesis is inhibited by administering to tissue an IGF-1R inhibitor. Tissues to be treated include an intestinal tissue, a cardiac tissue, a pulmonary tissue, a dermal tissue, or a hepatic tissue. The tissue is a tumor tissue.

Inhibition of angiogenesis is characterized by a reduction of blood vessel formation in the treated tissue compared to a tissue that has not been contacted with a IGF-1R. Tissues are directly contacted with an inhibitor. Alternatively, the inhibitor is administered systemically. Angiogenesis evaluated by methods known in the art such as the Matrigel plug assay.

Methods of Modulating Apoptosis

Also included in the invention are methods of inducing apoptosis or sensitizing a cell to apoptosis. By "inducing apoptosis" is meant that that the program cell death is initiated. Apoptosis is measured by methods known in the art, for example apoptosis is measured by annexin V staining.

In one aspect, apoptosis is achieved by contacting cell with an IGF-1R inhibitor. The cell is for example a tumor cell. The cell population that is exposed to, i.e., contacted with, IGF-1R inhibitor can be any number of cells, i.e., one or more cells, and can be provided in vitro, in vivo, or ex vivo.

Some disease conditions are related to the development of a defective down-regulation of apoptosis in the affected cells. For example, neoplasias result, at least in part, from an apoptosis-resistant state in which cell proliferation signals inappropriately exceed cell death signals. Moreover, certain disease conditions such as lymphoproliferative conditions, cancer including drug resistant cancer, arthritis, inflammation, autoimmune diseases and the like may result from a down regulation of cell death regulation. In such disease conditions, it would be desirable to promote apoptotic mechanisms.

Tumor cells have upregulation of anti-apoptotic mechanisms that protect them from physiological inducers of apoptosis as well as therapeutics that induce apoptosis, such as cytotoxics and chemotherapeutics. The pleiotropic pro-apoptotic changes resulting from inhibiting IGF-1R function in a tumor cell restores susceptibility to apoptotic signals.

Therapeutic Administration

The invention includes administering to a subject a composition comprising a compound that decreases IGF-1R expression or activity (referred to herein as an "IGF-1R inhibitor" or "therapeutic compound").

An effective amount of a therapeutic compound is preferably from about 0.1 mg/kg to about 150 mg/kg. For example, 1, 10, 25, 50, 75, 100, 125 mg/kg of an IGF-1R inhibitor is administered. Effective doses vary, as recognized by those skilled in the art, depending on route of administration, excipient usage, and coadministration with other therapeutic treatments (as described above) including the use of other anti-cancer agents or therapeutic agents for treating, preventing or alleviating a symptom of a particular cancer. A therapeutic regimen is carried out by identifying a mammal, e.g. a human patient suffering from (or at risk of developing) cancer, using standard methods.

The therapeutic compound (including other therapeutic treatments, e.g., cytotoxic agents, chemotherapeutic agents and anti-diabetic agents) is administered to such an individual using methods known in the art. Preferably, the compound is administered orally, rectally, nasally, topically or parenterally, e.g. subcutaneously, intraperitoneally, intramuscularly, and intravenously. The compound is optionally formulated as a component of a cocktail of therapeutic drugs to treat cancer. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, IGF-1R inhibitor is formulated in a capsule or a tablet for oral administration. Capsules may contain any standard pharmaceutically acceptable materials such as gelatin or cellulose, Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art.

IGF-1R inhibitor compounds are effective upon direct contact of the compound with the affected tissue. Accordingly, the compound is administered topically. For example, to treat myeloma the compound is applied to the area of skin affected. Alternatively, IGF-1R inhibitors are administered systemically. Additionally, compounds are administered by implanting (either directly into tumor or subcutaneously) a solid or resorbable matrix which slowly releases the compound into adjacent and surrounding tissues of the subject.

For example, for the treatment of gastrointestinal cancers, the compound is systemically administered or locally administered directly into gastric tissue. The systemic administration compound is administered intravenously, rectally or orally. For local administration, a compound-impregnated wafer or resorbable sponge is placed in direct contact with gastric tissue. The compound or mixture of compounds is slowly released in vivo by diffusion of the drug from the wafer and erosion of the polymer matrix.

Liver cancer is treated for example by infusing into the liver vasculature a solution containing the compound. For the treatment of a cancer of the neurological system the compound is administered intravenously or intrathecally (i.e., by direct infusion into the cerebrospinal fluid). For local administration, a compound-impregnated wafer or resorbable sponge is placed in direct contact with CNS tissue. The compound or mixture of compounds is slowly released in vivo by diffusion of the drug from the wafer and erosion of the polymer matrix. Alternatively, the compound is infused into the brain or cerebrospinal fluid using known methods. For example, a burr hole ring with a catheter for use as an injection port is positioned to engage the skull at a burr hole drilled into the skull. A fluid reservoir connected to the catheter is accessed by a needle or stylet inserted through a septum positioned over the top of the burr hole ring. A catheter assembly (e.g., an assembly described in U.S. Pat. No. 5,954, 687) provides a fluid flow path suitable for the transfer of fluids to or from selected location at, near or within the brain to allow administration of the drug over a period of time.

Pulmonary cancers are treated for example by administering the compound by inhalation. The compounds are delivered in the form of an aerosol spray from pressured container or dispenser which contains a suitable propellant, e.g., a gas such as carbon dioxide, or a nebulizer.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

EXAMPLES

The invention will be further illustrated in the following non-limiting examples.

Example 1

General Methods

Cell Lines and Primary Tumor Specimens

All cell lines studied are listed in Table 1. The dexamethasone (Dex)-sensitive parental line MM-1S and its Dex-resistant subline MM-1R cells were kindly provided by Dr Steven Rosen (Northwestern University, Chicago, Ill.); the chemosensitive parental MM cell line RPMI-8226/S, and its chemoresistant sublines RPMI-8226/Dox40 (doxorubicin-resistant), RPMI-8226/MR20 (mitoxantrone-resistant), RPMI-8226/LR5 (melphalan-resistant) cells were kindly provided by Dr William Dalton (lee Moffitt Cancer Center, Tampa, Fla.); the OCI-My5 cells were provided by Dr Meissner (University of Ontario, Toronto, Canada); the EJM, LP-1, KMM1, K620, OPM-1, and OPM-2 cells were provided by Dr Leif Bergsagel; INA-6 cells were provided by Renate Burger (University of Erlangen-Nuernberg, Germany); XG-1 cells were obtained from Dr Pierfrancesco Tassone (University of Magna Grecia, Italy); NCI-H929 and U266 cells were purchased from American Type Cell Culture (ATCC); MM-1S-myrAkt and MM-1S-Bcl-2 cells were established by stable transfection of MM-1S cells with constructs encoding for constitutively active myristoylated form of Akt and for Bcl-2, respectively. MM-1S-TR13 is a TRAIL/Apo2L-resistant subline established after 13 successive cycles of treatment of TRAIL/Apo2L-sensitive MM-1S parental cells with human recombinant form of TRAIL/Apo2L (N. Mitsiades, unpublished observation). MM-SAR-1 cells were established from primary MM tumor cells from a patient resistant to the proteasome inhibitor PS-341. We also studied the B-lymphoblastoid cell lines ARH-77, IM-9, HS Sultan and the leukemic cell lines REH and NALM-6 (purchased from ATCC), as well as a panel of human lymphoma cell lines, including the diffuse large B-cell lymphoma cell lines DHL-4, DHL-6, DHL-7, DHL-8 and DHL-10 (kindly provided by Dr Margaret Shipp, Dana-Farber Cancer Institute Boston, Mass.), the Burkitt's lymphoma lines Namalwa and the lymphoplasmacytic lymphoma (Waldenstrom's Macroglobulinemia) cell line WM-WSU (kind gift of Dr Ayad Al-Katib, Wayne State University, Detroit Cancer Center). All cells were cultured in RPMI 1640 medium (Life Technologies, Grand Island, N.Y.) supplemented with 10% charcoal dextran-treated fetal bovine serum (FBS; Hyclone, Logan, Utah) as well as L-glutamine, penicillin, and streptomycin (Life Technologies), except for INA-6 and XG-1 cells which were cultured in media supplemented with 20% FBS and 2.5 ng/mL of human recombinant IL-6. Primary MM tumor cells from 35 MM patients refractory to conventional or high-dose chemotherapy, thalidomide (and/or its immunomodulatory analogs), proteasome inhibitor PS-341 or other investigational agents were obtained (following informed consent) from bone marrow (BM) aspirate samples. After red blood cell lysis with 0.86% ammonium chloride, MM cells were selected by immunomagnetic separation-based positive selection with microbead-conjugated human anti-CD138 mAb (MACS, Miltenyi Biotech), or flow cytometric-based positive selection with phycoerythrin-conjugated anti-CD138 mAb, and as in prior studies. Purity (>95%) was assessed by both morphology and flow cytometry (Becton-Dickinson FACSort, Franklin Lakes, N.J.).

Primary MM patient samples were freshly isolated from bone marrow aspirates from patients undergoing diagnostic or restaging bone marrow aspirates under an IRB-approved protocol. MM cells were purified using custom-made RosetteSep cocktail of monoclonal antibodies (mAb's) (StemCell Technologies Inc, Vancouver, Canada) for negative selection of $CD138^+$ MM cells. The $CD138^-$ fraction of the MM cell purification process was cultured in 20% FBS-supplemented media for isolation of the adherent bone marrow stromal cells. Peripheral blood B cells were isolated by ficoll-density centrifugation of peripheral blood samples from MM patients.

Antibodies and Reagents

PS-341 (bortezomib) was provided by Millennium Pharmaceuticals (Cambridge, Mass.). Other reagents were obtained as follows: the mouse anti-human IGF-1R neutralizing monoclonal antibody aIR3 and Apo2L/TRAIL from Calbiochem; mouse monoclonal antibodies for Bcl-2, Bcl-$X_L$, Al/Bfl-1, FKHRL-1 and its phosphorylated forms, Bax, Raf, phosphorylated and total MEK½, IKK-a, Bcl-2, Bcl-$X_L$, GAPDH from Santa Cruz Biotechnology (Santa Cruz, Calif.); monoclonal antibody for FLIP from Upstate Biotechnologies (Lake Placid, N.Y.); rabbit polyclonal antibody against RANKL from Chemicon; monoclonal antibodies against hsp90, Akt, phospho-Akt, Bmx, IKK-a, Raf-1, RhoA, src, and $p70^{S6K}$ from Cell Signaling Technologies (Beverly, Mass.); human recombinant IGF-1, and IL-6, polyclonal antisera against cIAP-1, cIAP-2, and XIAP, as well as PE-conjugated monoclonal antibodies against IGF-1R, IL-6R, CD138, CD38, and CD45RA or MsIgG1 control antibodies (unconjugated or conjugated with FITC or PE) from R&D Systems, Inc. (Minneapolis, Minn.); MTT, dexamethasone, doxorubicin and melphalan from Sigma Chemical Co. (St Louis, Mo.); the JB-1 antagonistic peptide from Bachem Bioscience (King of Prussia, Pa.); the PE-conjugated anti-IGF-2R monoclonal antibody from Novus Biologicals (Littleton, Colo.); Fix&Perm permeabilization kit for intracellular flow cytometric analyses (Caltag Technologies); and the Enhanced Chemiluminescence (ECL) kit, which includes the peroxidase-labeled anti-mouse and anti-rabbit secondary antibodies, from Amersham (Arlington Heights, Ill.).

Transfections and Retroviral Transductions

Stable transfections of MM-1S cells with vectors encoding myristoylated (constitutively active) Akt or Bcl-2 (Upstate Biotechnologies, Lake Placid, N.Y.), or with empty (neo) vectors, were performed using Lipofectamine 2000 (Life Technologies) and G418-containing selection media, as previously described. Retroviral transduction of MM-1S and MM-1R cells with a pGC-gfp/luc vector (kind gift of C. G. Fathman, Stanford University) or pMMP-LucNeo was performed as previously described.

Ex Vivo Drug Sensitivity Assays

Cell survival of IGF-1R inhibitor-treated cells was examined using the 3-(4,5-Dimethylthiazol-2-yl)-2,5-Diphenyltetrazolium Bromide (MTT) calorimetric assay. Cells were plated in 48-well plates at 70-80% confluence (~50,000 cells/mL, 200 µL per well) and then incubated for 18 h with the indicated treatment. At the end of each treatment, cells were incubated with 1 mg/ml MTT for 4 hours at 37° C.; a mixture of isopropanol and 1N HCl (23:2, v/v) was then added under vigorous pipetting to dissolve the formazan crystals. Dye absorbance (A) in viable cells was measured at 570 nm, with 630 nm as a reference wavelength. Cell survival was estimated as a percentage of the value of untreated controls. All experiments were repeated at least three times, and each experimental condition was repeated at least in quadruplicate wells in each experiment.

In Vivo Anti-Tumor Activity of IGF-1R Inhibition

The in vivo anti-MM activity of ADW-742 was evaluated in a model of diffuse skeletal lesions of luciferase-expressing MM cells in SCID/NOD mice, serially monitored with whole-body bioluminescence imaging, as previously described. Briefly, male (6 to 8-week old) SCIDI/NOD mice (Jackson Laboratories, Bar Harbor, Me.) were sublethally irradiated (300 rads) using $^{137}CS$ γ-irradiator source. After 3-6 hours, $5 \times 10^6$ MM-1S-luc$^+$ cells in 100 µL of phosphate-buffered saline (PBS) was injected via the tail vein into each mouse. Mice were monitored daily for changes in their body weight, signs of infection, and paralysis, and weekly by whole-body bioluminescence imaging utilizing the In Vivo Imaging System (IVIS, Xenogen Corp, Alameda, Calif.) with total imaging time of 2 min, bin 2. Total body bioluminescence was quantified by integrating the photonic flux (photons/sec) through a standardized region of interest encompassing each mouse (Living Images, Xenogen). ADW-742 (Novartis Pharna AG, Basel, Switzerland) was formulated in 25 mM tartaric acid and administered by i.p. injection or by oral gavage. Melphalan (Alkeran, GlaxoSmithKline, Research Triangle Park, N.C.) was formulated according to manufacturer's instructions, and was administered by i.p. injection. All animal studies were approved by the Dana-Farber Cancer Institute Animal Care and Use Committee.

Flow Cytometry, Immunoblotting and Functional Assays

Flow cytometric analyses for IGF-1R, and IGF-2R were performed as previously described on a EPICS-XL-MCL flow cytometer (Beckman Coulter). Previously described protocols were applied for immunoblotting analyses; TRAP telomerase activity assay; 20S proteasome chymotryptic activity assay; DNA binding activity ELISAs for quantitative assessments of NF-κB and HIF-1a transcriptional activities. VEGF and IGF-1 ELISAs were performed according to manufacturer's instructions (R&D Systems, Minneapolis, Minn.).

Molecular Profiling of IGF-1R Inhibition

The gene expression profile of MM cells treated with IGF-1R inhibitors (ADW-742, α-IR3), in the presence or absence of serum were analyzed using U133A olignucleotide microarrays (Affymetrix Inc, Santa Clara, Calif.), using previously described protocols for total RNA extraction and purification, synthesis of cDNA and biotinylated cRNA, hybridization with human U133A Affymetrix chips, and scanning in HP ChipScanner to detect hybridization signals. Subsequent analysis of scanned image output files were analyzed with Affymetrix GeneChip Microarray Analysis Suite 5.0 software (Affymetrix), normalized and analyzed by hierarchical clustering, functional clustering and relevance network algorithms, as in previous studies. High-throughput global proteomic analysis of the signaling state of IGF-1R-inhibitor-treated MM cells was performed by multiplex-immunoblotting arrays using the KPKS-1.0 and KPSS-1.0 platforms, as previously described (Mitsiades C S et al. Semin Oncol. April 2003; 30(2): 156-60 and Mitsiades N et al. Blood. Mar. 15, 2003; 101(6): 2377-80).

Statistical Analysis

Statistical significance for in vitro assay results was examined by 2-way analysis of variance, followed by Duncan's post-hoc test. Statistical significance for bioluminescence imaging studies was determined by two-tailed student's t-test. In all analyses, P<0.05 was considered statistically significant. For assessment of in vivo anti-tumor activity, the overall survival of mice was defined as the time between i.v. injection of tumor cells and sacrifice or, death and was compared across different treatment groups with Kaplan-Meier survival analysis.

Gene Expression and Proteomic Profiling of IGF-1R Inhibition

Total RNA was extracted and purified with the Qiagen RNeasy kit (Qiagen, San Diego, Calif.). Five micrograms of total RNA was used in the first-strand cDNA synthesis with T7-d(T)$_{24}$ primer (GGCCAGTGAATTGTAATACGACT-CACTATAGGGAGGCGG-(dT)$_{24}$) (SEQ ID NO: 1) and Superscript II (GIBCO-BRL, Rockville, Md.). The second-strand cDNA synthesis was carried out at 16° C. by adding *Escherichia coli* DNA ligase, *E. coli* DNA polymerase I, and RNase H to the reaction, followed by T4 DNA polymerase to blunt the ends of newly synthesized cDNA. The cDNA was purified through phenol/chloroform and ethanol precipitation. Using the BioArray High Yield RNA Transcript Labeling Kit (Enzo Diagnostics, Farmingdale, N.Y.), the purified cDNA was incubated at 37° C. for 5 h in an in vitro transcription reaction to produce cRNA labeled with biotin. cRNA (20 µg) was fragmented by incubating in a buffer containing 200 mM Tris-acetate (pH 8.1), 500 mM KOAc, and 150 mM MgOAc at 94° C. for 35 min. The hybridization cocktail containing 15 µg adjusted fragmented cRNA mixed with Eukaryotic Hybridization controls (contains control cRNA and oligonucleotide B2) was hybridized with a pre-equilibrated human U133A Affymetrix chip at 45° C. for 16 h. After the hybridization cocktails were removed, the chips were washed in a fluidic station with low-stringency buffer (6× standard saline phosphate with EDTA, 0.01% Tween 20™ (Polysorbate), and 0.005% antifoam) for 10 cycles (two mixes/cycle) and high stringency buffer (100 mM N-morpholino-ethanesulfonic acid (MES), 0.1 M NaCl, and 0.01% Tween 20™ (Polysorbate)) for four cycles (15 mixes/cycle) and stained with SAPE (streptavidin phycoerythrin). This process was followed by incubation with normal goat IgG and biotinylated mouse anti-streptavidin antibody and restaining with SAPE. The chips were scanned in an HP ChipScanner (Affymetrix Inc, Santa Clara, Calif.) to detect hybridization signals. Scanned image output files were visually examined for major chip defects and hybridization artifacts and then analyzed with Affymetrix GeneChip® (array) Microarray Analysis Suite 5.0 software (Affymetrix). The image from each GeneChip® (array) was scaled such that the average intensity value for all arrays was adjusted to a target intensity of 150. The expression analysis files created by GeneChip® (array) Microarray Analysis Suite 5.0 software were exported as flat text files to Microsoft Excel and used for further analysis. Data analysis was performed to identify signals that were at least two-fold different between IGF-1R inhibitor-treated samples and their respective controls. These results were screened for p-values less than 0.0025 in Student's t test, to identify transcripts that were induced or repressed. For hierarchical clustering analysis, data were imported into the Gene Cluster and TreeView software (Stanford University, Stanford, Calif.). Additional softwares used for data mining include GeneSpring 5.0 (Silicon Genetics). Data were visualized using the Rainbow program (developed by Charles Bailey and Towia Libermann) that enables representation of data in color format according to their values on a logarithmic scale and with DNA-Chip Analyzer (dChip)3. Annotations and informations for all genes were retrieved using the NetAfix website (Affymetrix) and UnChip (Alberto Riva, Atul Butte, and Isaac Kohane; Childrens Hospital, Boston) and added to the data file. Annotated data were sorted according to functional relationships.

Proteomic Analyses of Signaling State of MM Cells

High-throughput global proteomic analysis of the signaling state of PS-341-treated MM cells was performed by multiplex-immunoblotting arrays using the KPKS-1.0 and KPSS-1.0 platforms, as previously described (Mitsiades C S et al. Semin Oncol. April 2003; 30(2): 156-60 and Mitsiades N et al. Blood. Mar. 15, 2003; 101(6): 2377-80).

Proteasome Chymotryptic Activity, NFkB and HIF-1α DNA Binding Activity 20S proteasome chymotryptic activity assay was performed as described [Shringarpure 2003]. The transcriptional activity of DNA binding activity of NF-κB and HIF-1α was measured as previously reported. Libermann T A, et al., . Proc Natl Acad Sci USA; 2002 99: 14374-14379; Mitsiades N. et al., 2002, 99: 4079-4086; Mitsiades N. et al., 2002; Blood 99: 4525-4530 and Mitsiades N., et al 2003 Blood; 101: 2377-2380.

Evaluation of IGF-1R Phosphorylation in MM Cells Treated with AEW541

To evaluate the degree of suppression of IGF-1R phosphorylation upon treatment with AEW-541, samples of NVP-AEW541-treated MM cells were processed by phospho-IGF-1R capture ELISA. Briefly, unpurified bone marrow aspirates from 11 MM patients were treated ex vivo with either NVP-AEW541 (250 nM for 15 min) or equal volume of DMSO control. Subsequently, each drug-treated and control sample from each patients was purified by negative selection using a custom-made RosetteSep cocktail of monoclonal antibodies (mAb's) for negative purification of CD138+ MM cells (the cocktail includes antibodies against CD2, CD14, CD33, CD41, CD45RA and CD66b). (Concomitant runs of BM aspirate samples from additional patients confirmed that this process leads to isolation of a population of >95% CD138+ CD38+ MM cells). The purified cells were then pelleted, frozen at −80° C. and stored until completion of collection of respective drug-treated and control samples from all patients (samples from different patients were treated and processed for MM cell purification at different times). Upon collection of samples from all patients, the respective cell pellets were lysed and then processed for IGF-1R capture ELISA. Briefly, Nunc-Immuno™ 96 MicroWell™ plates were coated with mouse anti-human IGF-1R antibody (Santa Cruz, sc-462) followed by incubation with rabbit anti-human Phospho-IGF-1R (Tyr1131)/phospho-1R (Tyr1146) Ab (3021 L, Cell Signaling Technologies, Beverly Mass.) and subsequent incubation with biotinylated 2° Ab (Jackson ImmunoResearch Laboratories Inc, #711-066-152), followed by incubation with streptavidin-HRP conjugate and detection using ABTS/$H_2O_2$ substrate.

Evaluation of Akt Phosphorylation in MM Cells Treated with AEW541

To evaluate the degree of suppression of Akt phosphorylation upon treatment with NVP-AEW-541, unpurified bone marrow aspirates from 9 MM patients (different from those of the IGF-1R phosphorylation capture ELISA) were treated ex vivo with either AEW541 (250 nM for 15 min) or equal volume of DMSO control. Subsequently, each drug-treated and control sample from each patients was purified by negative selection using a custom-made RosetteSep cocktail of monoclonal antibodies (mAb's) for negative purification of CD138+ MM cells (as described in the previous assay). The purified cells were then pelleted, frozen at −80° C. and stored until completion of collection of respective drug-treated and control samples from all patients (samples from different patients were treated, processed and purified at different times). Upon collection of samples from all patients, the respective cell pellets were lysed and then processed for phospho-Akt sandwich ELISA with the use of commercially available kit (Pathscan® Phospho-Akt1 (Ser473) Sandwich ELISA Kit, Cell Signaling, Beverly, Mass.). Briefly, cell pellets from the aforementioned experiments were lysed by 1× Cell Lysis Buffer (Cell Signaling Technologies, Beverly Mass., #9803) supplemented with 1 mM phenylmethylsulfonyl fluoride (PMSF) to each plate, sonicated and microcentrifuged for 10 minutes at 4° C. The supernatants were transferred to a new tube, aliquoted for equal protein content, diluted 1:1 with lysis buffer, and then added in duplicates in the wells of a 96-well plate coated with anti-phospho-Ser473-Akt-specific antibody. After an overnight incubation at 4° C., wells were incubated with an Akt1 (2H10) detection mAb, washed and then exposed to HRP-conjugated secondary antibody, followed by addition of TMB Substrate for 30 minutes at 25° C. and addition of 100 µl of STOP Solution, prior to measurement of absorbance at 450 nm within 30 minutes after adding STOP Solution.

Example 2

Characterization of Expression of IGF-1R in Hematologic Malignancies and Solid Tumors Flow cytometry was used to study a panel of 75 hematologic and solid tumor cell lines (Table 1) for expression of IGF-1R using 2 different anti-human IGF-1R monoclonal antibodies. Universal cell surface expression of IGF-1R was found in all cell lines tested, including hematologic malignancies (multiple myeloma, various subtypes of leukemias and lymphomas), as well as solid tumors (prostate, breast, lung, colon, thyroid, ovarian, renal, adrenal cancer, sarcomas, and retinoblastoma). To preclude the possibility that IGF-1R expression is an artifact induced by in vitro propagation, 35 freshly isolated primary multiple myeloma (MM) tumor specimens were examined, including samples from patients with resistance to conventional or high-dose chemotherapy, as well as classes of anti-tumor agents recently added to the therapeutic armamentarium against MM, including thalidomide, its immunomodulatory analogs (CC-5013), and the proteasome inhibitor bortezomib (PS-341). Cell surface expression of IGF-1R was also universally present in these primary patient samples (FIG. 7). Interestingly, there was no discernible pattern of association between the degree of surface IGF-1R expression and tumor type, histologic subtype or resistance to anti-cancer drugs (e.g. alkylating agents, anthracyclines, dexamethasone, thalidomide, CC-5013, TRAIL/Apo2L, or PS-341).

TABLE 1

| Tumor type | Cell lines |
|---|---|
| Multiple Myeloma | MM-1S, MM-1R, MM-1S-Akt, MM-1S-Bcl-2, MM-1S-TR13, RPMI-8226/S, RPMI-8226/Dox40, RPMI-8226/LR5, RPMI-8226/MR20, OPM-1, OPM-2, OPM-6, OCI-My5, OCI-My7, SKMM2, |

TABLE 1-continued

| Tumor type | Cell lines |
|---|---|
| | KMS-12-BM, KMS-12-PE, Brown, XG-1, L363, S6B45, U266, EJM, LP-1, S6B45, INA-6, NCI-H929, ARD, ARK, ARP-1, K620, KMM1, MM-AS, MM-SV and MM-SAR-1. |
| Leukemias | REH (acute lymphocytic leukemia, non-T, non-B) NALM-6 (acute pre-B-cell lymphocytic leukemia) KG-1a (acute erythroleukemia) GDM-1 (acute myelomonoblastic leukemia) HL-60 (acute promyelocytic leukemia) K562 (chronic myelogenous leukemia, blastic crisis) |
| Lymphomas | DHL-4, -6, -7, -8, -10 (diffuse large B-cell lymphomas) Namalwa (Burkitt's lymphoma) WM-WSU (Waldenstrom's Macroglobulinemia) |
| Breast Ca | MCF-7, MDA-MB-231, ZR-75-1 |
| Prostate Ca | PC-3, LNCaP, DU-145 |
| Lung Ca | NCI-H526 |
| Colon Ca | SW480 |
| Adrenal Ca | SW13, NCI-H295 |
| Thyroid Ca | FRO, ARO, NPA (anaplastic), WRO (follicular) TT (medullary), BHP-2, BHP-10, BHP-17, SW579 (papillary) |
| Renal Ca | ACHN, CAKI-1, 786-O |
| Ovarian Ca | 36M, SKOV-3 |
| Retinoblastoma | Y79, WERI |
| Sarcomas | SK-N-MC, TC71, TC106, TC248, TC268 |

Example 3

Analysis in Vitro Anti-Tumor Activity of IGF-1R Inhibitors

The functional impact of specific inhibition of IGF-1R activation in tumor cells was quantified in vitro by MTT colorimetric survival assays, to evaluate the degree to which inhibition of IGF-1R function can suppress the ability of serum (which contains IGFs) to stimulate an increase in the population of viable tumor cells. These assays involved use of 10% or 20% fetal bovine serum and/or pooled sera from healthy donors or sera from multiple myeloma (MM) patients, in comparison with serum-free conditions. Specific inhibition of IGF-1R function was achieved through use of a neutralizing monoclonal antibody α-IR3; the IGF-1-like competitive peptide antagonist JB1, or the selective IGF-1R kinase inhibitor ADW-742 (Novartis Pharma AG, Basel, Switzerland). Cellular kinase activity assays have demonstrated that ADW-742 has >16-fold more potent inhibitory effect against IGF-1R than insulin receptor (IR), the kinase with the highest homology to IGF-1R ($IC_{50}$ 0.17 and 2.8 μM, respectively, in cellular auto-phosphorylation assays). All three anti-IGF-1R inhibitory strategies significantly suppress serum-stimulated increase of the total population of viable tumor cells in all cell lines tested (FIGS. 1a, b, e). These results indicate that IGFs are key mediators of the ability of serum to stimulate the proliferation of tumor cells in vitro, and that specific inhibition of IGF-1R function supersedes the ability of other serum growth factors to stimulate proliferation/growth.

To determine the cell type-specific differences in response to IGF-1R inhibition, the effect of ADW-742 on the viability of 58 hematologic and solid tumor cell lines was assayed. Dose-dependent inhibition of serum-induced cell growth is observed in all cell lines (FIG. 1e). As a group, MM cell lines appear to be more sensitive to the effects of ADW-742, with $IC_{50}$ values generally in the 0.1-0.5 μM range, in comparison to the relatively higher $IC_{50}$ values observed in most other hematologic and solid tumor cell lines.

Further, the effect of IGF-1R inhibition on the viability of MM cells purified from primary patient samples in short-term culture assays immediately after isolation was validated. In all primary patient samples tested, inhibition of IGF-1R with a neutralizing antibody or ADW-742 completely suppresses serum-induced growth (FIGS. 1c, d). As a specificity control, an anti-IL-6 receptor (IL-6R) neutralizing antibody has no discernable effects on the viability of serum-cultured MM cells (FIGS. 1a, c, d). This finding may appear counterintuitive to the widely accepted role of IL-6 in tumor cell proliferation, survival and drug resistance in MM and other diseases, e.g. prostate cancer, raising the possibility that serum concentrations of IL-6 are not sufficient to stimulate tumor cells. However, it was determined that the response of MM and prostate cancer cells to exogenous administration of IL-6 (at levels in the 1-10 ng/mL range, which are 2-3 logs higher than serum IL-6 levels) is also abrogated by inhibition of IGF-1R (FIG. 8). These findings underscore the role for IGF-1R function in the hierarchy of growth factor receptor systems in tumor cells.

Figure 1:
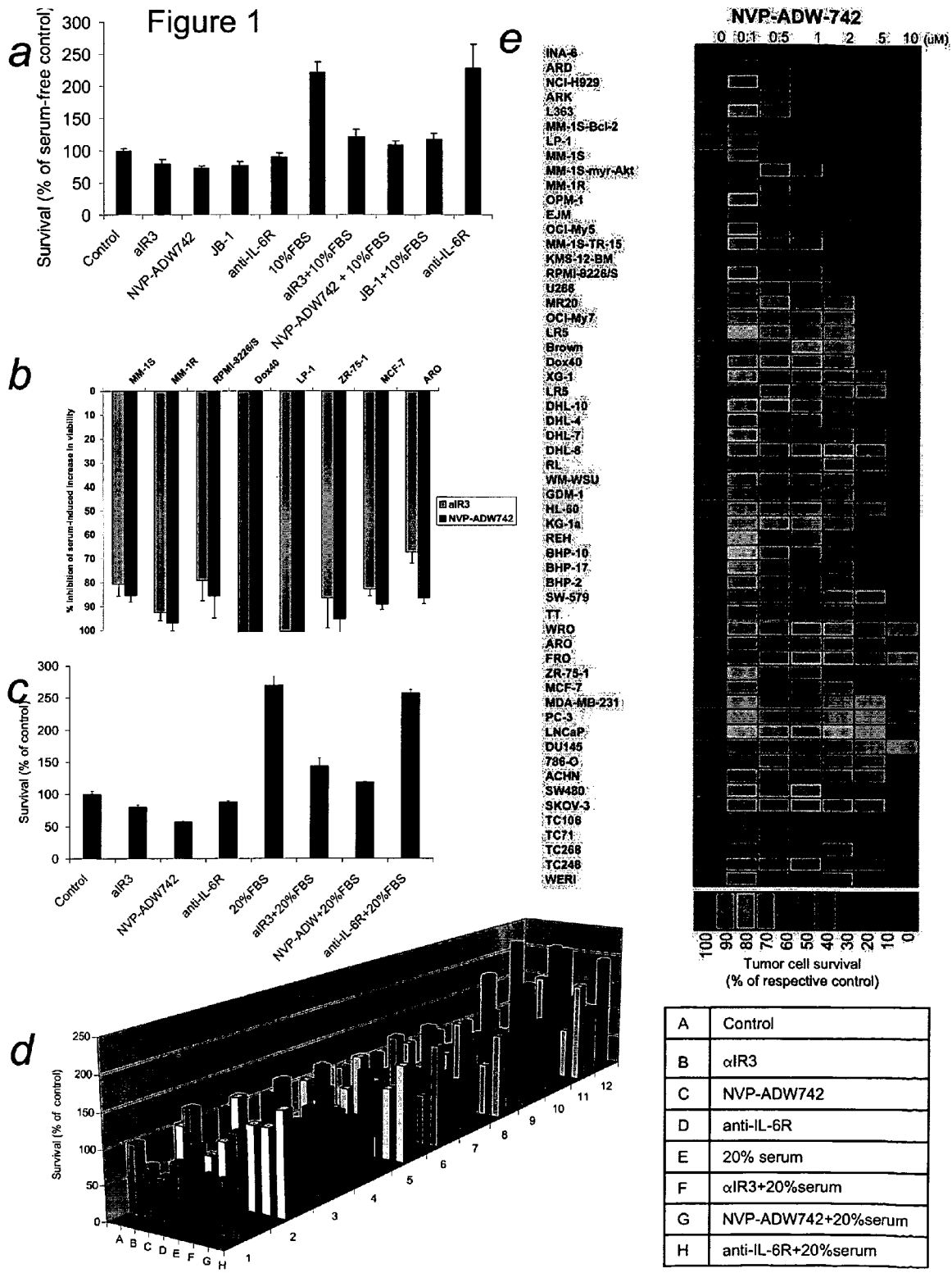
FIG. 1a is a bar chart demonstrating the in vitro anti-tumor activity of the IGF-1R inhibitors ADW-742 (0.5 µM), α-IR3 (2 µg/ml) and JB-1 (2 µg/ml) against the dexamethasone-resistant MM-1R cell line. Cells were incubated with IGF-1R inhibitors (or their respective controls, DMSO, MsIgG1 antibody or scrambled peptide) or an IL-6R neutralizing antibody (10 µg/ml) for 2 days in the presence or absence of serum. Results are expressed relative to respective vehicle-control.
FIG. 1b is a bar chart demonstrating the results of the effect of α-IR3 2 µg/mL or ADW-742 0.5 µM for 72 hours on a panel of drug-sensitive and resistant MM cell lines, as well prostate, breast and thyroid carcinoma cell lines. Results are presented as the % suppression of serum-induced increased in total population of viable tumor cells.
FIG. 1c is a bar chart demonstrating the in vitro activity of α-IR3, ADW-742, and anti-IL-6R (concentrations as specified in 1a) against primary MM tumor cells isolated from a patient resistant to conventional and high-dose chemotherapy, thalidomide, the immunomodulatory thalidomide derivative CC-5013, and PS-341.
FIG. 1d is a chart demonstrating the in vitro activity of α-IR3 and ADW-742 against a panel of primary MM tumor cells isolated from patients resistant to conventional and investigational therapies.
FIG. 1e is a chart showing the dose-response matrix of a panel of cell lines from MM (black letters), other hematologic malignancies (red letters) and solid tumors (blue letters) to ADW-742 at 0-10 μM for 72 hours. Relative survival is visualized in an assigned color scale.

Moreover, ADW-742, α-IR3 or JB-1 are active even against MM cell lines with known resistance to conventional (cytotoxic chemotherapy, dexamethasone) or investigational (thalidomide, CC-5013, TRAIL/Apo2L, PS-341) anti-cancer agents (FIG. 1), as well as primary tumor cells from MM patients with multi-drug resistant disease (FIG. 1d). Furthermore, the degree of sensitivity of MM or other neoplasias to IGF-1R inhibitors is not associated with the level of surface expression of IGF-1R (FIG. 7). Because the IGF/IGF-1R cascade can be counteracted by the expression of IGF-receptor 2 (IGF-2R, IGF-IIR, CD222 or CIMPR), the expression of IGF-2R in the panel of tumor cells disclosed in Table I was analyzed. IGF-2R is expressed on the surface of a minority of tumor cell lines, but is found intracellularly in the entire tumor cell panel tested (FIG. 9). No discernible association was observed between the degree of either surface or intracellular IGF-2R expression and tumor type, histologic subtype or resistance to the aforementioned panel of conventional and investigational anti-cancer drugs. Also, there is no apparent association between IGF-2R levels and sensitivity to IGF-1R inhibition.

Example 4

Determination of the In Vivo Anti-Tumor Activity of the Selective IGF-1R Kinase Inhibitor ADW-742

The in vivo anti-tumor activity of IGF-1R inhibition in a mouse xenograft model of MM was examined. The MM cell line MM-1S was engineered to stably express firefly luciferase fused to a selectable marker (neomycin phosphotransferase or enhanced GFP). Sub-lethally irradiated NOD/SCID mice were injected intravenously with MM-1S-Luc cells and tumor distribution was followed by serial whole-body non-invasive imaging of visible light emitted by luciferase-expressing tumor cells upon injection of mice with luciferin. Given the importance of the tumor microenvironment to the biology of MM, a model system of diffuse MM skeletal lesions was established. Intravenous injections of MM-1S-Luc cells lead to their engraftment to bone marrow and bone and consistent establishment of diffuse bone lesions in the axial skeleton (vertebrae, skull, pelvis) and long bones (FIG. 2a). The anatomic distribution of these MM lesions is consistent with the presentation of disease in human MM patients, and progression to diffuse visceral invasion recapitulates the disseminated skeletal and extraskeletal involvement of malignant plasma cells in clinically aggressive MM (e.g., plasma cell leukemia).

The in vivo anti-tumor efficacy of IGF-1R inhibition with ADW-742 was analyzed in the orthotopic MM model described supra. Sublethally irradiated NOD/SCID mice were injected with MM1S-Luc cells, and serially imaged to monitor tumor burden. After 2-3 weeks, cohorts of mice with similarly increasing tumor burden were divided into control and treatment groups. In this model of MM, ADW-742 monotherapy (10 mg/kg i.p. twice daily) significantly suppresses tumor growth (FIG. 2b) and prolongs the survival of mice (FIG. 2c). There is no difference in body weight between treatment groups (P=0.82) and no other significant treatment-related toxicity. Consistent results were obtained with a second study with the same i.p. dosing, as well as a third study utilizing ADW-742 dosed orally at 50 mg/kg twice daily.

Example 5

Molecular Sequelae of IGF-1R Inhibition

To investigate the molecular pathways implicated in IGF-1R activation and, conversely, its inhibition, the molecular sequelae triggered in MM cells upon their exposure to IGF-1R inhibitors (in the presence or absence of serum) were characterized using gene expression profiling (with U133A Affymetrix oligonucleotide microarrays) and signal transduction proteomic profiling (using multiplex immunoblotting analyses). The functional significance of findings detected in the global molecular profiling assays is confirmed by specific mechanistic assays.

Global expression profiling reveals distinct transcriptional profiles distinguishing serum-free from serum-stimulated cells (FIG. 3a). Cells treated solely with physiological levels of IGF-1 (but otherwise serum-free) have expression profiles consistent with those of cells exposed to serum. Conversely, when serum-exposed cells are treated with either $\alpha$-IR3 or ADW-742, the expression profiles cluster with those of cells grown in serum-free conditions as shown by unsupervised hierarchical clustering (FIG. 3a). Therefore, activation of IGF-1R by the IGFs contained in serum constitutes a major part of the transcriptional effects of serum. Furthermore, the global effects of inhibiting IGF-1R by ADW-742 or a specific neutralizing antibody are concordant, thus further supporting the specificity of ADW-742 activity. Of note, unsupervised hierarchical clustering analyses show that the gene expression profiles of MM cells treated with IGF-1R inhibitor (ADW-742 and $\alpha$-IR3) correspond to a distinct cluster, separate from other clusters corresponding to profiles of MM cells treated with other potent anti-MM agents (including bortezomib, hsp90 inhibitors and histone deactylase inhibitor). This indicates that the distinct molecular sequelae of IGF-1R inhibition do not reflect a non-specific cytotoxic or anti-proliferative effect.

Figure 3:
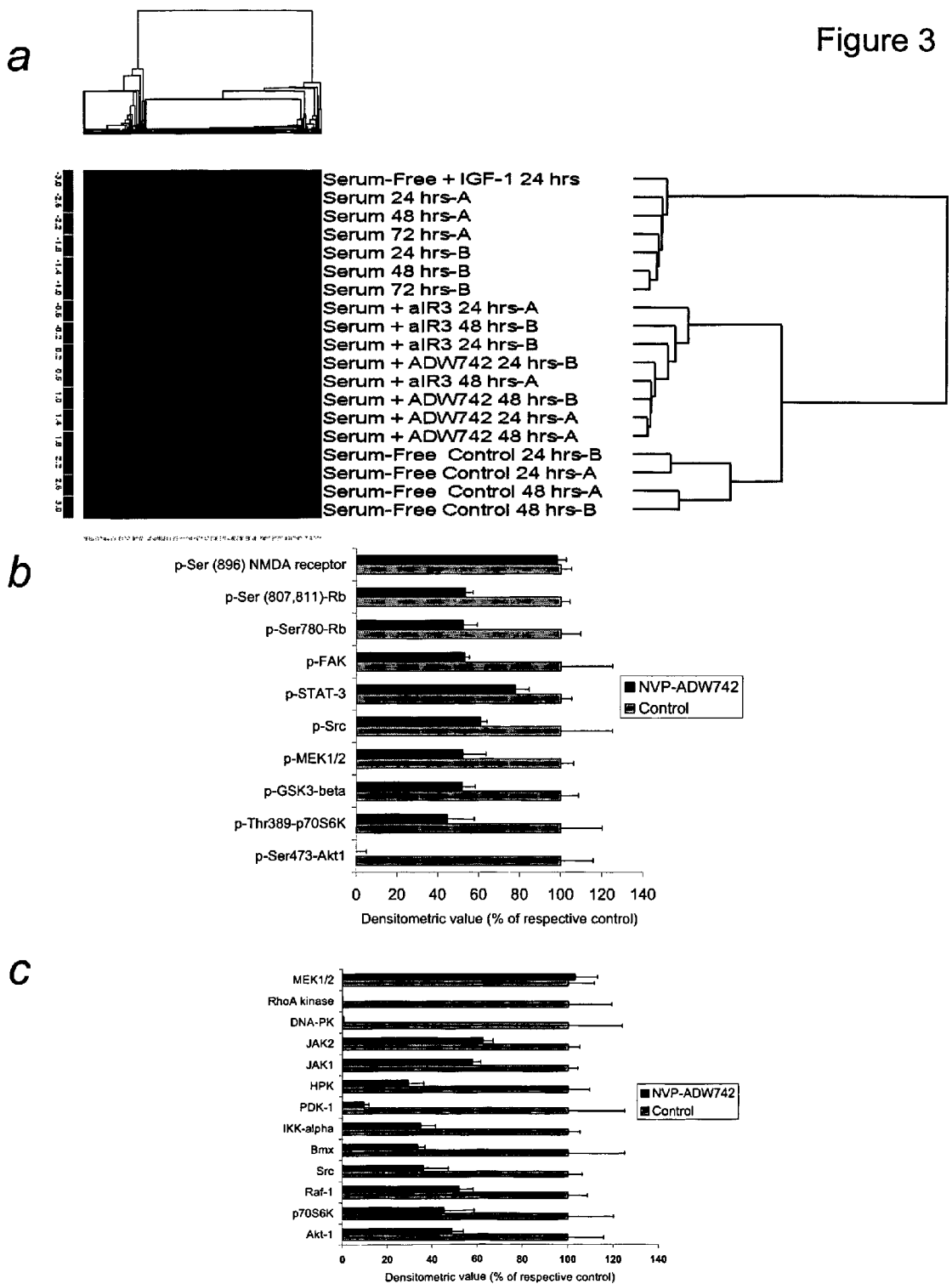
FIG. 3a is a chart demonstrating the unsupervised hierarchical clustering of transcriptional profiles of MM-1S cells cultured for the indicated times in the presence or absence of 10% fetal bovine serum, ADW-742 0.5 μM, α-IR3 2 μg/ml, or IGF-1 200 ng/mL.
FIG. 3b is a bar chart demonstrating densitometric results of proteomic analyses of the signaling state of MM-1S cells cultured in serum-containing medium in the presence or absence of ADW-742 at 0.5 μM. Results of phosphorylation state and total levels (FIG. 3c) of signaling mediators in the setting of ADW-742 treatment are represented as % of the respective controls (mean of 2 independent replicates ±SD). The specificity of the aforementioned sequelae of IGF-1R inhibition is indicated by the lack of significant effect (NS) on respective negative controls, including total levels of kinases such as MEK½ or phosphorylation status of targets such as the NMDA receptor. All other differences were significant with p<0.05.
FIG. 3c is a bar chart demonstrating densitometric results of proteomic analyses of the signaling state of MM-1S cells cultured in serum-containing medium in the presence or absence of ADW-742 at 0.5 μM. Results measuring total levels of signaling mediators in the setting of ADW-742 treatment are represented as % of the respective controls (mean of 2 independent Replicates ±SD). The specificity of the aforementioned sequelae of IGF-1R inhibition is indicated by the lack of significant effect (NS) on respective negative controls, including total levels of kinases such as MEK½ or phosphorylation status of targets such as the NMDA receptor. All other differences were significant with p<0.05.
Figure 4:
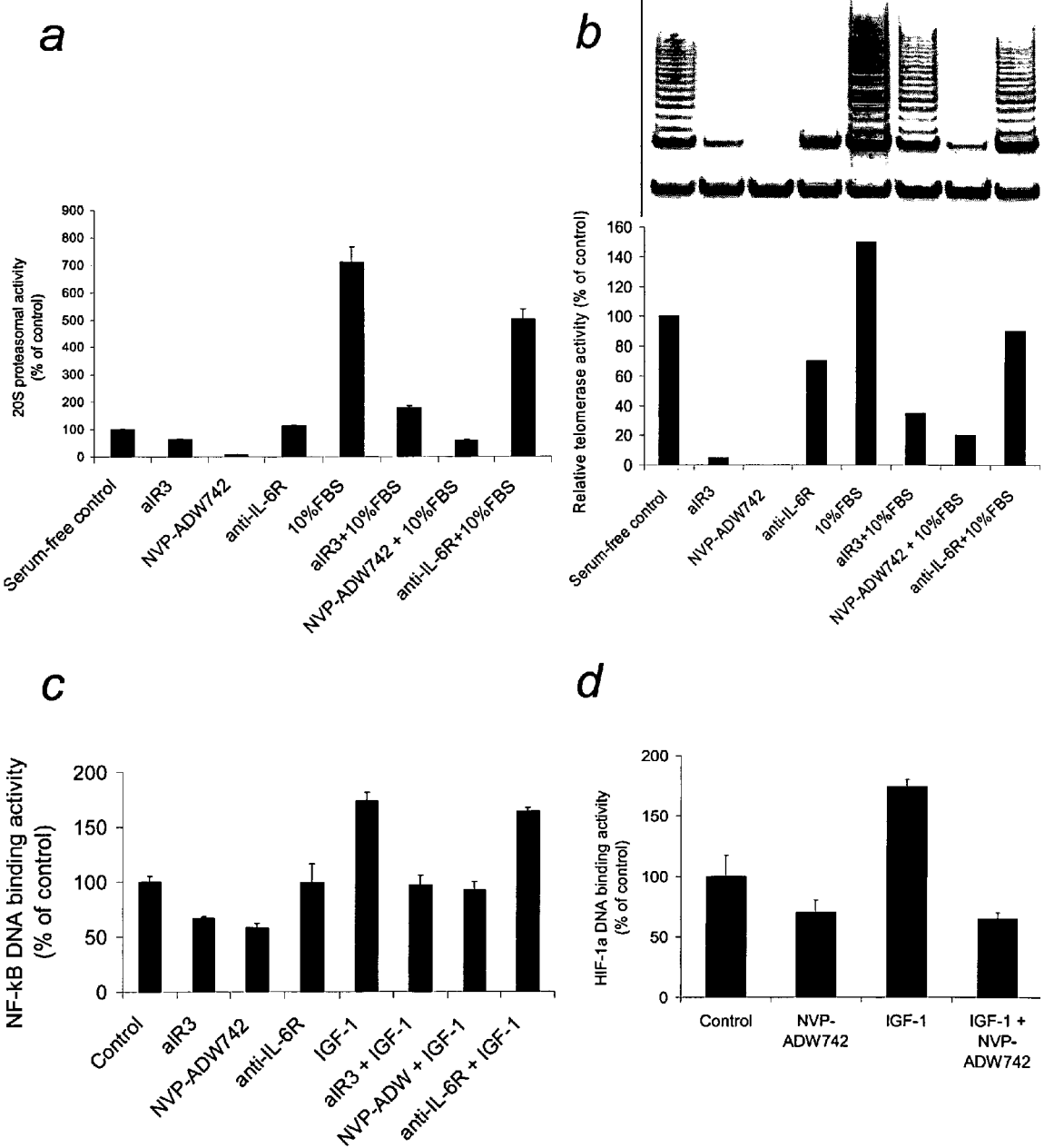
FIG. 4a is a bar chart showing the effect of IGF-1R inhibition on 20S proteasome activity. MM1S cells were grown for 24 hours in the presence or absence of 10% fetal bovine serum, a-IR3 2 μg/ml, ADW-742 0.5 μM, or anti-IL-6R antibody 2 μg/ml.
FIG. 4b is a photograph and a bar chart demonstrating the effect of IGF-1R inhibition on telomerase activity.
FIG. 4c is a bar chart demonstrating the effect of IGF-1R inhibition on NF-κB DNA-binding activity.
FIG. 4d is a bar chart demonstrating the effect of IGF-1R inhibition on HIF-1α DNA-binding activity.
Figure 5:
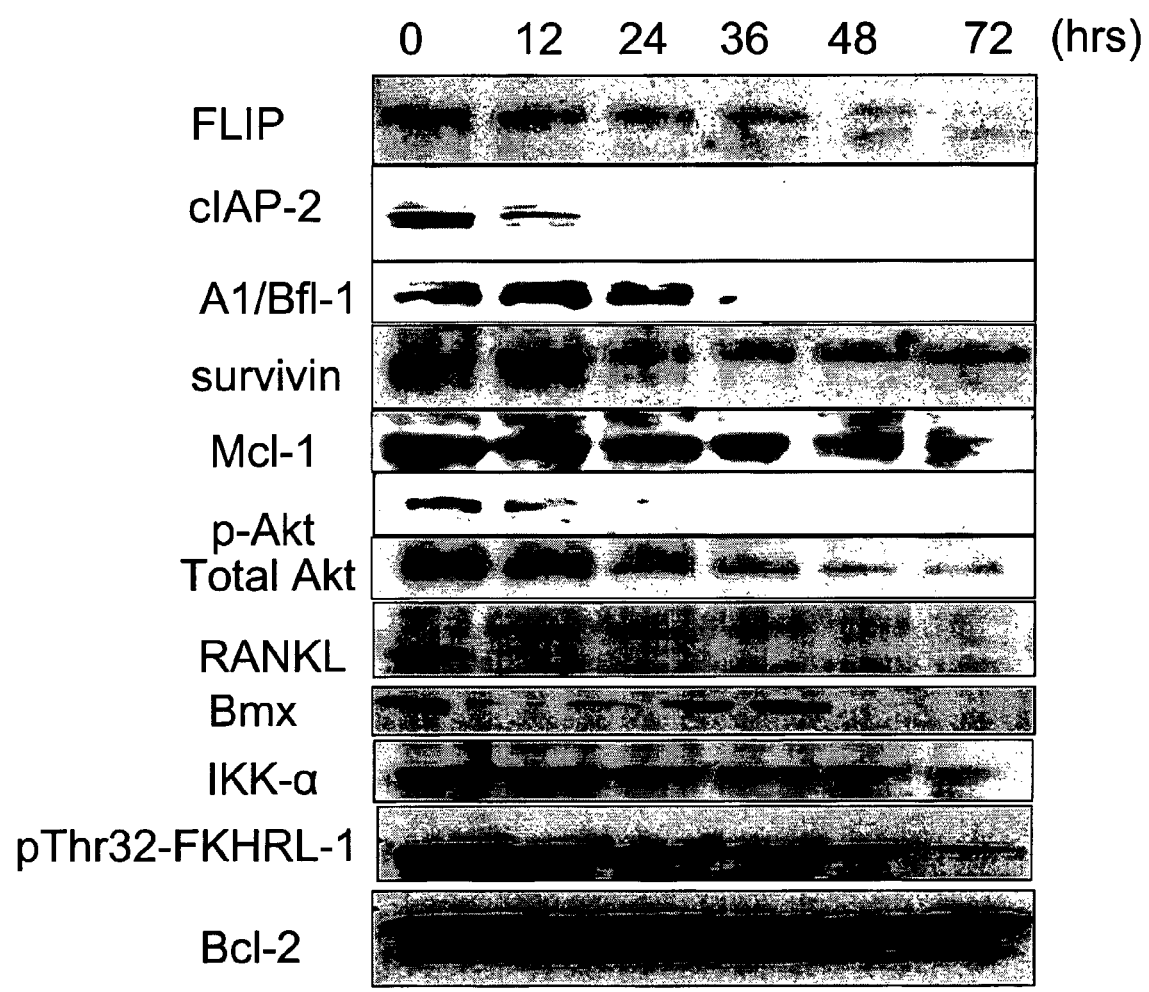
FIG. 5 is a collection of photographic images of Western blots demonstrating the effects of IGF-1R inhibition on anti-apoptotic signaling cascades. These confirmatory immunoblotting analyses indicate that ADW-742 treatment (500 nM) of MM-1S cells in serum-containing medium induced pleiotropic anti-proliferative/pro-apoptotic molecular events, such as early suppression of Akt, MEK½ and FKRHL-1 phosphorylation, as well as decrease in intracellular levels of Akt, Bmx, IKK-α and the osteoclastogenic stimulator (and mediator of bone resorption in osteolytic MM lesions) RANKL.

Expression profiling studies, proteomic analyses, and subsequent confirmatory assays show that tumor cell exposure to IGF-1 or serum is associated with highly pleiotropic constellation of proliferative/anti-apoptotic molecular events, which are suppressed by IGF-1R inhibition with ADW-742 or $\alpha$-IR3 (FIGS. 3-5 and S4). IGF-1R inhibition leads to decreased expression of genes implicated in cell cycle progression/proliferation and decreased Rb phosphorylation; decreased levels of caspase inhibitors (e.g. FLIP, XIAP, cIAP-2, survivin) and other anti-apoptotic regulators (e.g. A1/Bfl-1); suppression of multiple genes involved in DNA synthesis and DNA damage repair; significant decrease in constitutive and serum-stimulation of telomerase activity; suppression of genes implicated in oncogenic transformation (e.g. c-myb, DEK) and decreased phosphorylation (and total levels) of the Aurora family of kinases; decreased expression of transcripts encoding the 26S proteasome subunits, modulation of other genes regulating proteasome function (e.g. ubiquitin-specific proteases and ubiquitin conjugating enzymes) and suppression of constitutive and serum-induced activation of proteasome activity; decreased expression of genes for nucleocytoplasmic transport and other solute carrier proteins regulating uptake of glucose and other metabolites; suppression of heat shock proteins (e.g. hsp90); decreased phosphorylation of critical kinases and kinase targets in the PI-3K/Akt pathway (including Akt, p70S6K, GSK3beta, FKHRL-1), Raf/ERK½ pathway (MEK½), Src, STAT3, and FAK (focal adhesion kinase); suppression of total intracellular levels of kinases implicated in proliferative/anti-apoptotic responses, including Akt, p70S6K, Raf, Src, Bmx, IKK, and PDK1 (PI-3K-dependent kinase); and suppression of transcriptional activity of NF-κB and HIF-1α, 2 downstream targets of IKK and Akt respectively.

The highly pleiotropic constellation of proliferative/anti-apoptotic pathways which are stimulated by serum and conversely inhibited by ADW-742 explains the potent growth/survival signal mediated by IGF-1R, and the major impact of IGF-1R inhibitors on a wide range of tumor types in this study. Several molecular sequelae of IGF-1R inhibition elucidated by these studies are consistent with previously reported findings (e.g. pertaining to Akt, FKHRL-1, NF-κB and HIF-1α function or caspase inhibitor expression), while previously unidentified findings also emerged. For example, the IGF-1R inhibition modulates the signaling state of tumor cells not only by changes in phosphorylation of the components of PI-3K/Akt, Ras/Raf/ERK½, IKK/NF-κB or other signaling cascades, but also by modulating the intracellular concentration of components of these pathways, including key kinases such as Akt, Raf, and IKK. IGF/IGF-1R signaling activates/upregulates several signaling effectors (e.g. Akt, Raf, IKK), and participates in signal transduction cascades triggered by other cytokines/growth factors and their receptors. The transcriptional profiles of IGF-1R inhibitor treatment of serum-cultured MM cells are comparable to the profiles in serum-free conditions (FIG. 3a), highlight a critical role of IGF-1R function for the transcriptional responses of tumor cells to the entire spectrum of growth factors present in serum.

Example 6

IGF-1R Inhibition Sensitizes Tumor Cells to Other Anti-Cancer Agents

Several pathways abrogated by IGF-1R inhibition are critical for tumor cell resistance to pro-apoptotic therapies and/or constitute known targets for anti-cancer therapies. By way of non-limiting example, Akt, NF-κB and caspase inhibitors confer resistance to multiple caspase-dependent pro-apoptotic anti-cancer therapies (including dexamethasone, TRAIL/Apo2L, proteasome inhibitors, thalidomide analogs), while NF-κB activity and DNA damage repair genes play critical roles in tumor cell resistance to cytotoxic chemotherapy. In addition, proteasome function is a target of the recently emerging small molecule inhibitor PS-341.

The ability of IGF-1R inhibitors to sensitize tumor cells to other anti-cancer therapies in vitro was determined. ADW-742 or α-IR3 increases the sensitivity of MM cells to various cytotoxic chemotherapeutic agents (doxorubicin, melphalan), dexamethasone, TRAIL/Apo2L, or PS-341 (FIGS. 6a-c and 12), the sensitivity of prostate cancer cells to doxorubicion, or the response of SK-N-MC sarcoma cells to Fas ligation. These data indicate a broader role of IGFs/IGF-1R signaling in attenuating anti-cancer drug responsiveness in multiple neoplasias and the potential usefulness of IGF-1R inhibitors in enhancing the anti-tumor activity of a broad spectrum of anti-cancer therapeutic strategies.

Furthermore, the suppression of proteasome function by IGF-1R inhibition provides first evidence of growth factor-mediated regulation of proteasome function. This finding offers a non-limiting mechanistic explanation for the demonstrated synergy between IGF-1R inhibition and PS-341 (FIG. 6b), is consistent with observations that IGF-1-induced signaling attenuates MM cell sensitivity to PS-341, and bears major implications for the potential clinical applications of IGF-1R inhibitors to enhance the anti-tumor activity of proteasome inhibitors.

Example 7

Effect of IGF-1R Inhibition on Interactions of Tumor Cells with the BM Microenvironment and VEGF Production The importance of stromal elements in supporting tumor growth is well known, particularly in osteotropic malignancies, such as MM, where stromal elements of the BM microenvironment confer protective effects to tumor cells against various anti-tumor therapies. This protective effect may be particularly relevant for strategies targeting IGF-1R, since IGFs are locally produced in the BM milieu by BM stromal cells (BMSCs) and osteoblasts and because co-culture of MM cells with BMSCs significantly enhances production of IGF-1 in vitro (FIG. 12c). However, in co-culture assays of MM cells and BMSCs, this interaction does not overcome the anti-tumor effects of ADW-742 on MM cells (FIG. 12a), even at concentrations which did not affect the viability of BMSCs (FIG. 12c). Furthermore, consistent with its ability to suppress IGF-1-induced HIF-1α activity, ADW-742 decreases the production of VEGF by tumor cells and bone marrow stromal cells (FIG. 12d), and suppresses the IGF-1-induced secretion of VEGF by various tumor types such as thyroid cancer cells (FIG. 12e) or MM cells, suggesting putative anti-angiogenic effects of IGF-1R inhibition (FIG. 12d). These results indicate that IGF/IGF-1R signaling plays important roles in the interactions of tumor cells with their local microenvironment, including stromal protection of tumor cells or tumor-associated angiogenesis, and propose an additional mechanistic rationale for use of IGF-1R kinase inhibitors in order to maximize the in vivo efficacy of other anti-tumor therapies.

Example 8

In Vivo Chemosensitizing Effect of IGF-1R Inhibition with ADW-742

Figure 6:
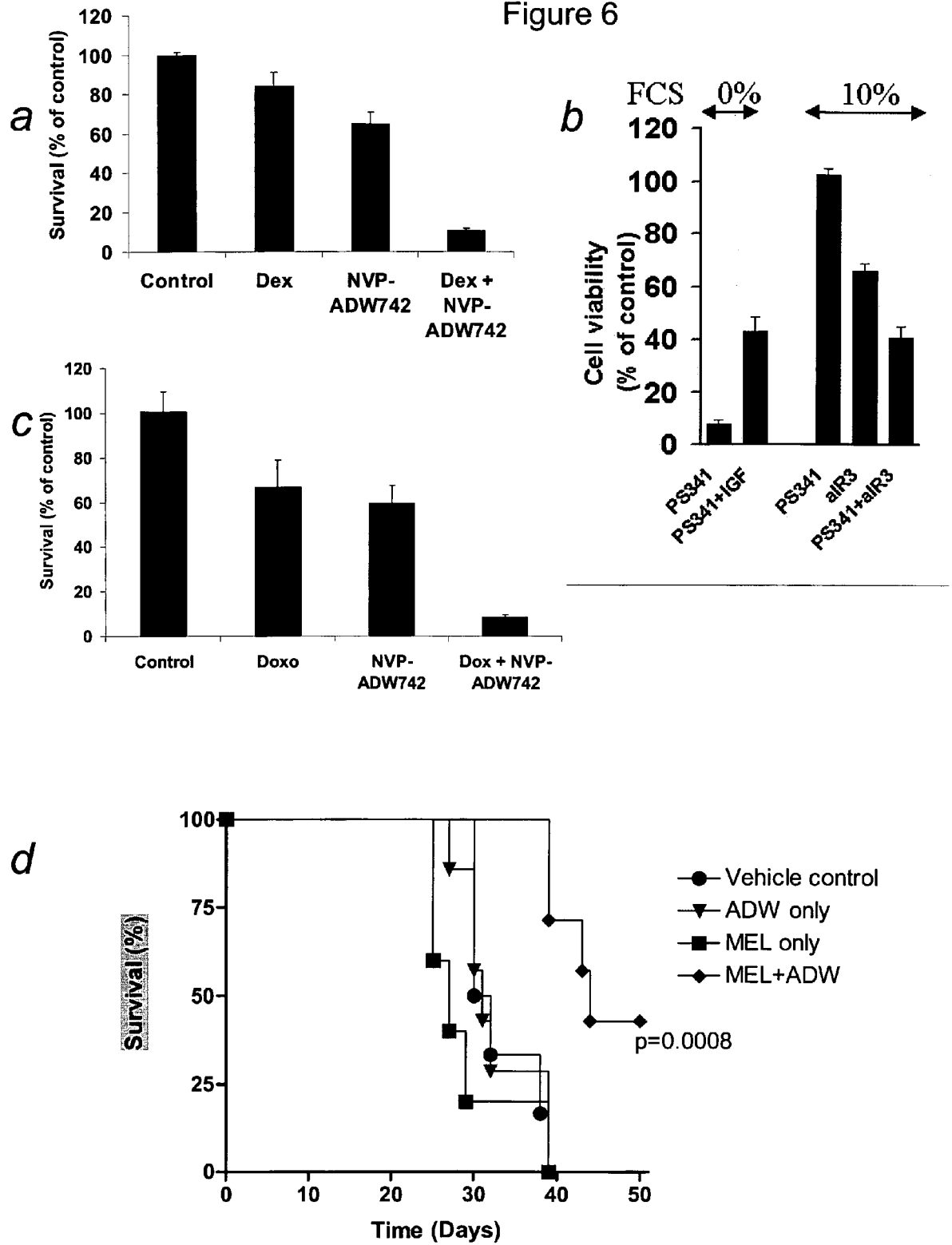
FIG. 6a is a bar chart showing that the in vitro anti-MM activities of dexamethasone (Dex, 0.1 μM, 72 hours) are enhanced by ADW-742 treatment (750 nM for the final 24 hours of incubation) in MM-1S cells.
FIG. 6b is a bar chart showing that the in vitro anti-MM activities of doxorubicin (Doxo, 50 ng/mL, 48 hours) are enhanced by ADW-742 treatment (750 nM for the final 24 hours of incubation) in MM-1S cells.
FIG. 6c is a bar chart demonstrating that IGF-1R inhibition (by α-IR3 2 μg/mL) enhances the activity of PS-341 (2 nM, overnight incubation) against MM-1S cells. Cells were cultured in the presence of 10% FBS, and results are expressed as mean ±SD of 3 independent experiments.
FIG. 6d is a line graph showing the results of studies in which, two weeks after i.v. injection with MM-1S-Luc cells, a group of NOD-SCID mice with established diffuse MM lesions was divided into 4 cohorts, with statistically equivalent tumor burden as assessed by bioluminescence imaging. Cohorts were treated with melphalan alone (2.5 mg/kg i.p. once a week), ADW-742 alone (10 mg/kg i.p. twice daily, four days per week), melphalan followed 18 hours later by ADW-742, or vehicle control. ADW-742 enhanced the in vivo anti-tumor effect of melphalan, as shown by the prolongation of overall survival of mice receiving the combination of the 2 agents (log-rank test, P=0.0008).

Based on the in vitro chemosensitizing effect of ADW-742 on tumor cells, a clinically-relevant, SCID/NOD model of diffuse skeletal MM-1S-luc lesions was evaluated for the in vivo activity of a pulse of ADW-742 (10 mg/kg i.p. twice daily, 4 days per week) administered after low dose melphalan (2.5 mg i.p once a week). In contrast to continuous administration of ADW-742, pulsatile administration of ADW-742 has no significant anti-tumor activity (FIG. 6d, and data not shown). However, consistent with the in vitro data, the combination of sub-therapeutic melpahalan followed by sub-therapeutic ADW-742 has a synergistic effect in prolonging the survival of mice (FIG. 6d). Taken together, these results demonstrate that abrogation of IGF-1/IG-1R signaling after cytotoxic therapy enhances the efficacy of conventional therapies by removing key anti-apoptotic signals.

Example 9

In Vitro Anti-Proliferative Activity of NVP-AEW541 Against a Panel of Multiple Myeloma Cell Lines To evaluate the degree to which inhibition of IGF-1R function can suppress the ability of serum (which contains IGFs) to stimulate proliferation of MM cell lines, an MTT calorimetric survival assay was applied to cells exposed to increasing concentrations of NVP-AEW541 (FIG. 13).

Example 10

Effect of NVP-AEW541 on the Viability of Primary Multiple Myeloma Tumor Samples In Vitro The effect of IGF-1R inhibition was then tested on the viability of MM cells purified from primary patient samples, in short-term culture assays performed immediately after isolation. NVP-AEW541 at 0.5 µM significantly inhibited the basal, as well as the serum stimulated survival, of primary MM cells (FIG. 14).

Example 11

Effect of IGF-1R Kinase Inhibition on IL-6 Response

When the effect of NVP-AEW541 (at 0.5 µM) on the survival of primary MM cells was compared to that of an anti-IL-6 strategy (at 2 µg/mL), the latter was surprisingly found to have little or no effect, while the NVP-AEW541 suppressed serum stimulated survival as previously observed (FIG. 15). This finding may appear counterintuitive to the widely accepted role of IL-6 in tumor cell proliferation, survival and drug resistance in raising the possibility that serum concentrations of IL-6 are not sufficient to stimulate tumor cells. MM. Hallek M, et al 1998 Blood; 91: 3-21 and Anderson K C, and Lust J A 1999 Semin Hematol; 36: 14-20. However, we further found that the response of MM cells to exogenous administration of IL-6 (at levels in the 1-10 ng/mL range, which are 2-3 logs higher than serum IL-6 levels. Nakashima J. et al 2000 Clin Cancer Res; 6: 2702-2706 was also abrogated by inhibition of IGF-1R (FIG. 16). These findings underscore an apparent pivotal role for IGF-1R function in the hierarchy of growth factor receptor systems in tumor cells.

Example 12

NVP-AEW541 Selectively Impairs the Survival of Primary MM Cells, as Opposed to Bone Marrow Stromal Cells To assess whether MM cells are more susceptible to inhibition of IGF-1R signaling, than normal cells in their immediate environment, primary MM cells, normal bone marrow stromal cells and peripheral blood B-cells, were exposed to 0.5 µM NVP-AEW541. Inhibition of IGF-1R kinase activity by the compound was shown to significantly impair the survival of primary MM cells obtained from three patients, but had no effect on the viability of bone marrow stromal cells or peripheral blood B-cells (FIG. 17).

Example 13

Combination Studies with NVP-AEW541 and Standard Chemotherapeutic Agents for the Treatment of Multiple Myeloma In consideration of the fact the IGF-1R signaling provide a cell survival signal and that this seems to play a major role in sustaining the viability of MM cells in vitro, combination experiments with chemotherapeutic agents used in the clinic for the treatment of Multiple Myeloma patients were assessed using primary MM samples. NVP-AEW541 was found to synergistically sensitize primary MM cells to the action of Dexamethasone (FIG. 18), Doxorubicine (FIG. 19) and Melphalan (FIG. 20). In addition, NVP-AEW541 sensitized primary MM cells to the proteasome inhibitor bortezomib (PS-341) (FIG. 21).

Example 14

NVP-AEW541 Inhibits the Chemotryptic Activity of the Proteasome

Previous studies showed that IGF-I signaling promotes the expression of selected proteasome subunits (Mitsiades C S, et al. 2004 Cancer Cell; 5: 221-230) and renders MM cells less sensitive to proteasome inhibitors, such as PS-341. Mitsiades N. et al., 2002 Proc Natl Acad Sci USA; 99: 14374-14379. NVP-AEW541 at 0.5 µM was found to inhibit proteasome function, measured as chemotryptic activity, in primary MM samples (FIG. 22).

Example 15

NVP-AEW541 Inhibits the DNA Binding Activity of NFkB

Based on the observation that IGF-I signaling in MM cells triggers multiple downstream events, such as the activation of IKK (Mitsiades C S, et al. 2004 Cancer Cell; 5: 221-230)), the effect of NVP-AEW541 on the activation of NFkB, measured as a function of its DNA binding activity, was tested. At 0.5 µM, NVP-AEW541 was found to significantly impair NFkB DNA binding activity (FIG. 23).

Example 16

NVP-AEW541 Inhibits the DNA Binding Activity of HIF-1α

IGF-I signaling has been reported to have pro-angiogenic function by inducing HIF-1α transcriptional activity and VEGF expression. Fukuda R., et al. 2002 J Biol Chem; 277: 38205-38211.

Consistently, NVP-AEW541 at 0.5 µM was found to inhibit HIF-1α DNA binding activity in primary multiple myeloma cells (FIG. 24).

Example 17

Monitoring of Phospho-IGF-1R and Phospho-Akt Level in Primary Multiple Myeloma Samples Upon Ex Vivo Exposure to NVP-AEW541

To assess the possibility to develop a methodology suitable for the detection of pharmacodynamic changes at the level of IGF-1R phosphorylation or downstream Akt phosphorylation, primary patient derived multiple myeloma samples were treated ex vivo with 0.25 µM NVP-AEW541 or its solvent DMSO. CD138+ multiple myeloma cells were then enriched by negative selection and used to monitor the level of phospho-IGF-1R and phospho-Akt by capture ELISA. Samples exposed to NVP-AEW541 consistently showed a marked reduction in the level of phospho-IGF-1R (FIG. 25) and phospho-Akt (FIG. 26), compared to vehicle treated controls.

Example 18

Efficacy of NVP-AEW541 in an Orthotopic Mouse Model of Multiple Myeloma

MM1S-LucNeo cells were created by transducing MM1S cells with a retrovirus encoding the firefly luciferase coding region fused to neomycin phosphotransferase (pMMP-Luc-Neo). Transduced cells were selected by growth in medium (RPMI, 10% FBS, penicillin/streptomycin) containing G418 at an effective concentration of 1 mg/ml.

NOD-SCID mice (Jackson Laboratory) were sublethally irradiated with 300 rads from a $^{137}$CS source. Three hours after irradiation, a total of $5 \times 10^6$ MM1S-LucNeo cells in mid-logarithmic growth phase were injected via tail vein into each mouse in a volume of 300 µL of PBS. Mice were maintained under sterile conditions.

Bioluminescence imaging was performed with a Xenogen In Vivo Imaging System (IVIS 100). Mice were anesthetized by IP injection of ketamine 150 mg/kg and xylazine 12 mg/kg, and simultaneously D-luciferin 50 mg/kg was administered by IP injection. Imaging was performed 15 minutes after D-luciferin injection with a setting of 2 minutes, and a bin setting of 2. Mice were allowed to recover under isothermic conditions. Mice were imaged weekly beginning 2 weeks after tumor inoculation. Mice with increasing tumor burden were divided into 2 statistically equivalent cohorts, and treatment was started 4 weeks after tumor inoculation. NVP-AEW541 was dissolved in 25 mM tartaric acid at a concentration of 5 mg/ml, and 10 µL/gm body weight was administered by oral gavage twice-a-day, for a final dose of 50 mg/kg PO BID. Vehicle was 25 mM tartaric acid alone, again administered at 10 µL/gm body weight.

The effect of AEW541 administration on orthotopic multiple myeloma tumor growth was assessed by in vivo bioluminescence imaging. Tumor burden was significantly reduced after 15 days of treatment (p=0.04, student t-test). Of note, 4/8 vehicle treated animals died between imaging at day 8 and imaging at day 15 of treatment. Since animals that die from disease have the highest tumor burden, the significant difference in tumor burden in treatment groups was likely an underestimation of the true difference in anti-tumor efficacy. There was no difference in body weight after 8 days of treatment (p=0.58).

These results are an extension of more comprehensive studies demonstrating in vivo efficacy of NVP-ADW742 in an orthotopic xenograft mouse model of multiple myeloma (Mitsiades et al. 2004 Cancer Cell; 5: 221-230). The degree of tumor suppression is similar in comparing the efficacy of NVP-AEW541 (FIG. 27) and NVP-ADW742 (Mitsiades et al. 2004 Cancer Cell; 5: 221-230; FIG. 3), and are concordant with the similarity in in vitro efficacy of these two compounds.

Example 19

Evaluation of the Effect if AEW541 on Breast Cancer Growth

The effect of AEW541 on the growth of breast cancer cells in a bone metastasis model was studied. Human bone chips were inoculated with a breast cancer cell line (MDA-MB231-LucNeo), and implanted into nude mice. Bone chips and tumor cells were allowed to "take root" for 2 weeks, and then treatment with AEW541 was initiated. The growth of tumor cells was followed by imaging over the subsequent 4 weeks, demonstrating a clear anti-tumor effect in this mouse model of breast cancer metastases to the bone. (FIG. 28).

Example 20

Combination Anti-Tumor Therapies Using AEW541

The potential use of AEW541 in combination with other targeted therapeutics was evaluated. A glioma cell line (U87-LucNeo) was stereotactically implanted into the brains of nude mice. 10 days after implantation, mice were divided into groups treated with AEW541 alone, AMD3100 alone (a CXCR4 inhibitor), both in combination, or vehicle control. The growth of tumors was monitored by imaging, revealing additive antitumor efficacy of AEW541 in combination with AMD3100. FIG. 29.

What is claimed is:

1. A method of inhibiting multiple myeloma cell growth in a subject comprising administering to said subject a cytotoxic or a chemotherapeutic agent and a composition comprising an insulin-like growth factor receptor-1 (IGF-1R) inhibitor, wherein said IGF-1R inhibitor is ADW-742 or NVP-AEW541.

2. The method of claim 1, wherein said composition is administered concomitantly with said agent.

3. The method of claim 1, wherein said composition is administered within 48 hours after said agent.

4. The method of claim 1, wherein said composition is administered within 24 hours after said agent.

5. The method of claim 1, wherein said composition is administered within 12 hours after said agent.

6. The method of claim 1, wherein said composition is administered within 3-12 hours after said agent.

7. The method of claim 1, wherein said composition is administered over a preselected period of time.

8. The method of claim 7, wherein said preselected period of time is about 1 to 2 days.

9. The method of claim 1, wherein the dose of said agent is sub-therapeutic.

10. The method of claim 1, wherein the dose of said IGF-1R inhibitor is sub-therapeutic.

11. The method of claim 1, wherein the dose of said IGF-1 R inhibitor is in an amount sufficient to cause hyperglycemia, ketosis or glucosurioa.

12. The method of claim 1, wherein said chemotherapeutic agent is doxorubicin, melphalan or dexamethasone.

13. The method of claim 1, wherein said IGF-1R inhibitor is ADW-742.

14. The method of claim 1, wherein said IGF-1R inhibitor is NVP-AEW541.

* * * * *